US012793812B2

(12) United States Patent
Barbacioru et al.

(10) Patent No.: US 12,793,812 B2
(45) Date of Patent: Nov. 10, 2026

(54) DETECTING THE PRESENCE OF A TUMOR BASED ON OFF-TARGET POLYNUCLEOTIDE SEQUENCING DATA

(71) Applicant: GUARDANT HEALTH, INC., Redwood City, CA (US)

(72) Inventors: Catalin Barbacioru, Redwood City, CA (US); Darya Chudova, San Jose, CA (US); Aliaksandr Artsiomenka, Mountain View, CA (US); Daniel Gaile, Redwood City, CA (US); Hao Wang, Redwood City, CA (US)

(73) Assignee: GUARDANT HEALTH, INC., Palo Alto, CA (US)

( * ) Notice: Subject to any disclaimer, the term of this patent is extended or adjusted under 35 U.S.C. 154(b) by 1033 days.

(21) Appl. No.: 17/691,049

(22) Filed: Mar. 9, 2022

(65) Prior Publication Data

US 2022/0344004 A1 Oct. 27, 2022

Related U.S. Application Data

(60) Provisional application No. 63/173,273, filed on Apr. 9, 2021, provisional application No. 63/158,824, filed on Mar. 9, 2021.

(51) Int. Cl.
*G16B 30/10* (2019.01)
*G16B 20/10* (2019.01)
*G16B 20/20* (2019.01)

(52) U.S. Cl.
CPC ............ *G16B 30/10* (2019.02); *G16B 20/10* (2019.02); *G16B 20/20* (2019.02)

(58) Field of Classification Search
None
See application file for complete search history.

(56) References Cited

U.S. PATENT DOCUMENTS

| | | | |
|---|---|---|---|
| 5,912,148 | A | 6/1999 | Eggerding |
| 6,130,073 | A | 10/2000 | Eggerding |
| 6,210,891 | B1 | 4/2001 | Nyren et al. |
| 6,258,568 | B1 | 7/2001 | Nyren |
| 6,582,908 | B2 | 6/2003 | Fodor et al. |
| 6,818,395 | B1 | 11/2004 | Quake et al. |
| 6,833,246 | B2 | 12/2004 | Balasubramanian |
| 6,911,345 | B2 | 6/2005 | Quake et al. |
| 6,969,488 | B2 | 11/2005 | Bridgham et al. |
| 7,115,400 | B1 | 10/2006 | Adessi et al. |
| 7,169,560 | B2 | 1/2007 | Lapidus et al. |
| 7,170,050 | B2 | 1/2007 | Turner et al. |
| 7,282,337 | B1 | 10/2007 | Harris |
| 7,302,146 | B2 | 11/2007 | Turner et al. |
| 7,313,308 | B2 | 12/2007 | Turner et al. |
| 7,329,492 | B2 | 2/2008 | Hardin et al. |
| 7,476,503 | B2 | 1/2009 | Turner et al. |
| 7,482,120 | B2 | 1/2009 | Buzby |
| 7,501,245 | B2 | 3/2009 | Quake et al. |
| 7,537,898 | B2 | 5/2009 | Bost et al. |
| 9,598,731 | B2 | 3/2017 | Talasaz et al. |
| 2001/0053519 | A1 | 12/2001 | Fodor et al. |
| 2003/0152490 | A1 | 8/2003 | Trulson et al. |
| 2011/0160078 | A1 | 6/2011 | Fodor et al. |
| 2020/0248272 | A1 | 8/2020 | Kennedy et al. |

FOREIGN PATENT DOCUMENTS

| | | | |
|---|---|---|---|
| WO | 2017009372 | A2 | 1/2017 |
| WO | 2017106768 | A1 | 6/2017 |
| WO | 2018119452 | A2 | 6/2018 |
| WO | 2018192967 | A1 | 10/2018 |
| WO | 2021168146 | A1 | 8/2021 |

OTHER PUBLICATIONS

Talevich E. CNVkit: genome-wide copy No. detection and visualization from targeted DNA sequencing. Plos Computational Biology 12(4): 1-18. (Year: 2016).*
Kuilman T. CopywriteR: DNA copy number detection from off-target sequence data. Genome Biology 16(49): 1-15. (Year: 2015).*
Altschul, S.F et al. "Basic local alignment search tool" J Mol Biol (1990) 215(3):403-410.
Astier, Y. et al. "Toward Single Molecule DNA Sequencing: Direct Identification of Ribonucleoside and Deoxyribonucleoside 5'-Monophosphates by Using an Engineered Protein Nanopore Equipped with a Molecular Adapter" J Am Chem Soc (2006) 128(5):1705-1710.
Barbacioru, C. et al. "Abstract 571: Detection of somatic copy No. alterations from on-target and off-target sequencing data" Cancer Research, American Association for Cancer Research, AACR Annual Meeting 2021, Apr. 10-15, 2021 and May 17-21, 2021; Philadelphia, PA Jul. 1, 2021 XP55922127.
Chen, G.K. et al. "Precise inference of copy number alterations in tumor samples from SNP arrays" Bioinformatics (2013) 29(23):2964-2970.
International search report and written opinion for International Patent Application No. PCT/US2022/071059 dated May 31, 2022.
Kuilman, T. et al. "CopywriteR: DNA copy No. detection from off-target sequence data" Genome Biology, (2015) 16(1):49.
Levy, S.E. et al. "Advancements in Next-Generation Sequencing" Ann Rev Genomics & Hum Genetics (2016) 17:95-115.
Li et al. "Fast and accurate short read alignment with Burrows-Wheeler transform" Bioinformatics, 2009; vol. 25, pp. 1754-1760.
Li, J. et al. "CONTRA: copy number analysis for targeted resequencing" Bioinformatics (2012) 28(10):1307-1313.

(Continued)

*Primary Examiner* — Olivia M. Wise
*Assistant Examiner* — Robert J. Kallal
(74) *Attorney, Agent, or Firm* — Stephen W. Chen

(57) ABSTRACT

In implementations described herein, information derived from a sample that is derived from off-target sequences can be used to determine estimates for the copy number of tumor cells and/or the tumor fraction of a sample. Additionally, information derived from the presence of germline SNPs can be used to determine estimates for at least one of the copy number of tumor cells or the tumor fraction of a sample.

25 Claims, 20 Drawing Sheets

(56) References Cited

OTHER PUBLICATIONS

Liu, L. et al. "Comparison of Next-Generation Sequencing Systems" J Biomed & Biotech (2012) Article ID251364:1-11.
Maclean, D. et al. "Application of 'next-generation' sequencing technologies to microbial genetics" Nature Rev Microbiol (2009) 7:287-296.
Needleman, S.B. et al. "A general method applicable to the search for similarities in the amino acid sequence of two proteins" J. Mol. Biol. (1970) 48:443-453.
Olshen, A.B. et al. "Circular binary segmentation for the analysis of array-based DNA copy number data" Biostatistics (2004) 5(4):557-572.
Pardoll, D.M. "The blockade of immune checkpoints in cancer immunotherapy" Nature Rev Cancer (2012) 12:252-264.
Talevich, E et al. "CNVkit: Genome-Wide Copy Number Detection and Visualization from Targeted DNA Sequencing" PLoS Comput Biol (2016) 12(4): e1004873. https://doi.org/10.1371/journal.pcbi.1004873.
Voelkerding, K.V. et al. "Next-generation sequencing: from basic research to diagnostics" Clin Chem (2009) 55:641-658.
Zhang, J. et al. "PowerBLAST: A New Network BLAST Application for Interactive or Automated Sequence Analysis and Annotation" Genome Res. (1997) 7:649-656.
Siravegna, G. et al. "Integrating liquid biopsies into the management of cancer" Nature Reviews Clinical Oncology (2017) 14:531-548.
Exam Report for European Patent Application No. 22713247.9 dated Aug. 13, 2025.

* cited by examiner

| sample_id | gene | chrom_before | cnv_type_before | copy_number_before | estimated_cn_before | segment_size_before | cnv_type_after | copy_number_after |
|---|---|---|---|---|---|---|---|---|
| C0019861 | CDH1 | 16 | homdel | 1.56656 | 1.64 | 21296686.0 | loh | 1.56514 |
| C0019861 | FANCA | 16 | homdel | 1.56656 | 1.64 | 21296686.0 | loh | 1.56514 |
| C0019868 | ARID1A | 1 | amplification | 2.13290 | 2.13 | 249100001.0 | no_cnv | 2.03105 |
| C0019860 | ARID1A | 1 | amplification | 2.12179 | 2.16 | 241076709.0 | no_cnv | 2.00775 |
| C0019860 | ATR | 3 | no_cnv | 1.98213 | 2.00 | 197556663.0 | loh | 1.88654 |
| C0021564 | SETD2 | 3 | amplification | 2.10556 | 2.25 | 187679053.0 | loh | 1.91938 |
| C0021564 | BAP1 | 3 | amplification | 2.10556 | 2.25 | 187679053.0 | loh | 1.91938 |
| C0021564 | PBRM1 | 3 | amplification | 2.10556 | 2.25 | 187679053.0 | loh | 1.91938 |

Figure 20

DETECTING THE PRESENCE OF A TUMOR BASED ON OFF-TARGET POLYNUCLEOTIDE SEQUENCING DATA

CROSS-REFERENCE TO RELATED APPLICATIONS

This application claims the benefit of priority of U.S. Provisional Patent Application No. 63/158,824, filed Mar. 9, 2021, and U.S. Provisional Patent Application No. 63/173,273, filed Apr. 8, 2021, each of which is incorporated by reference herein in its entirety for all purposes.

BACKGROUND

A tumor is an abnormal growth of cells. A tumor can be benign or malignant. A malignant tumor is often referred to as a cancer. Cancer is a major cause of disease worldwide. Each year, tens of millions of people are diagnosed with cancer around the world, and more than half eventually die from it. In many countries, cancer ranks as the second most common cause of death following cardiovascular diseases. Early detection is associated with improved outcomes for many cancers.

Cancers are often detected by biopsies of tumors followed by analysis of cell pathologies, biomarkers, or DNA extracted from cells. Conventional biopsies can be painful and invasive. Such biopsies also can often only examine a fraction of the tumor cells within a subject based on the sample of tissue extracted from the tumor. Thus, conventional tissue biopsies offer limited information about a tumor in relation to a specific period of time and are not always representative of the population of tumor cells.

More recently it has been proposed that cancers can also be detected from cell-free nucleic acids (e.g., circulating nucleic acid, circulating tumor nucleic acid, exosomes, nucleic acids from apoptotic cells and/or necrotic cells) in body fluids, such as blood or urine (see, e.g., Siravegna et al., *Nature Reviews,* 14:531-548 (2017)). DNA is often released into bodily fluids when, for example, normal and/or cancer cells die, as cell-free DNA and/or circulating tumor DNA. Tests that measure cell-free nucleic acids have the advantage that they are non-invasive, can be performed without identifying suspected cancer cells to biopsy, and sample nucleic acids from all parts of a cancer. Analyzing data obtained in such tests to detect the presence of a tumor can be complicated by the fact that the amount of nucleic acids released into body fluids is low and variable as is recovery of nucleic acids from such fluids in analyzable form.

BRIEF DESCRIPTION OF THE DRAWINGS

The accompanying drawings, which are incorporated in and constitute a part of this specification, illustrate certain implementations, and together with the written description, serve to explain certain principles of the methods, computer readable media, and systems disclosed herein. The description provided herein is better understood when read in conjunction with the accompanying drawings which are included by way of example and not by way of limitation. It will be understood that like reference numerals identify like components throughout the drawings, unless the context indicates otherwise. It will also be understood that some or all of the figures may be schematic representations for purposes of illustration and do not necessarily depict the actual relative sizes or locations of the elements shown.

FIG. 20 includes a table showing actual copy number of various genes and differences between the copy number of the genes estimated using segmentation according to an implementation of a CBS process based on coverage data only and the copy number of the genes estimated using the refinement process shown in FIGS. 18 and 19.

SUMMARY OF THE DISCLOSURE

Figure 1:
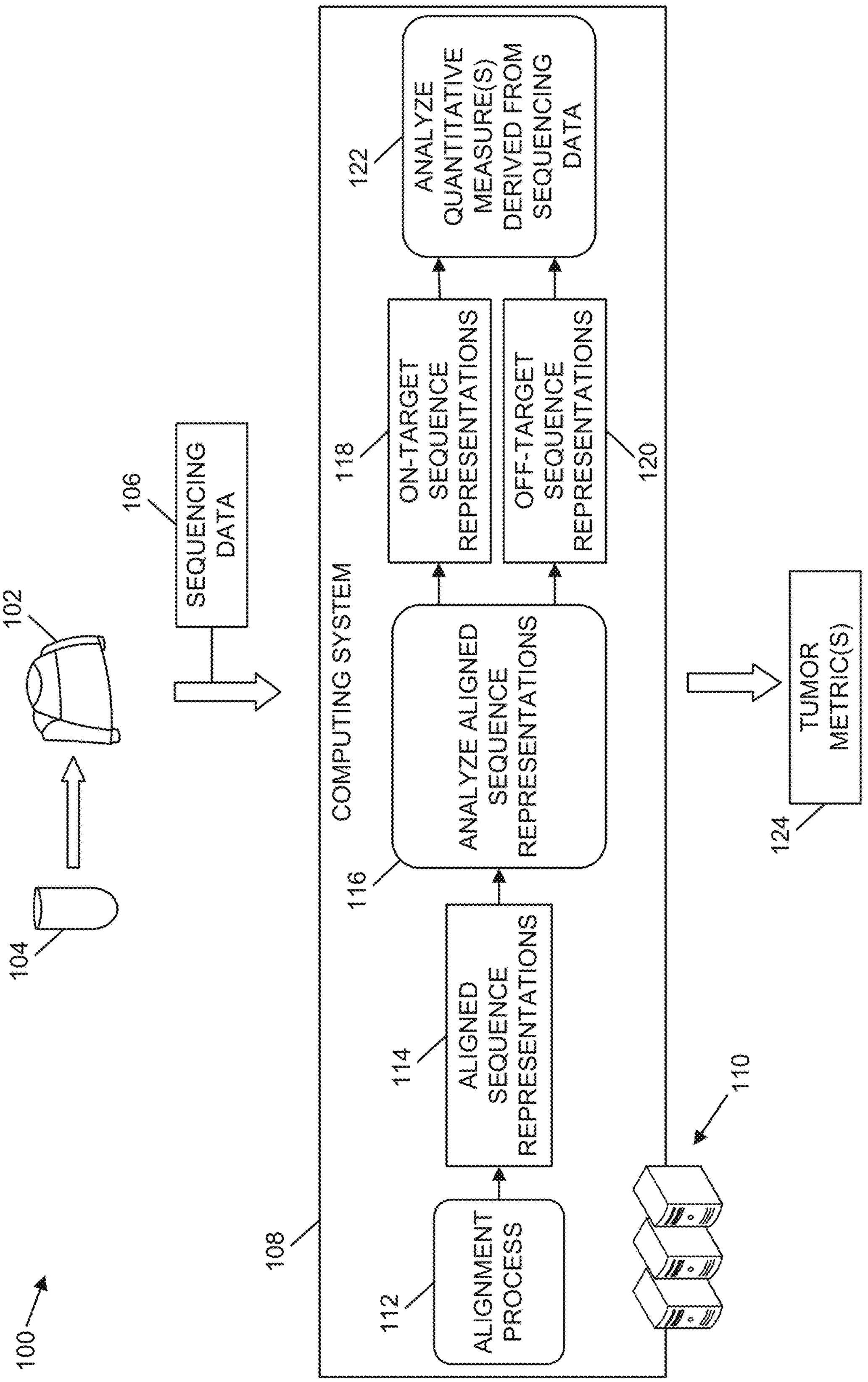
FIG. 1 is a diagrammatic representation of an example architecture that determines tumor metrics related to a subject based on off-target polynucleotides, according to one or more implementations.

In some aspects, a method comprising: obtaining, by a computing system including one or more computing devices each having one or more processors and memory, sequence data indicating sequence representations related to polynucleotide molecules included in a sample; generating, by the computing system, a set of aligned sequence representations by performing an alignment process that determines one or more of the sequence representations that have at least a threshold amount of homology with respect to a portion of a reference human genome; determining, by the computing system, a set of off-target sequence representations by identifying a first portion of the number of aligned sequence representations that do not correspond to target regions of the reference human genome; determining, by the computing system, a set of on-target sequence representations by identifying a second portion of the number of aligned sequence representations that correspond to the target regions of the reference human genome; determining, by the computing system, first segments of the reference human genome, wherein the first segments do not include the target regions; determining, by the computing system, first quantitative measures for individual first segments based on a respective subset of the set of off-target sequence representations corresponding to the individual first segments; determining, by the computing system, first normalized quantitative measures for individual first segments with respect to an additional quantitative measure of the individual first segments; determining, by the computing system, second normalized quantitative measures for individual first segments by adjusting individual first normalized quantitative measures with respect to a reference quantitative measure for the individual first segments; determining, by the computing system, second segments of the reference human genome, individual second segments including a greater number of nucleotides than the individual first segments and including a plurality of the individual first segments; determining, by the computing system, second quantitative measures for individual second segments based on the first normalized quantitative measures and the second normalized quantitative measures of the respective plurality of individual first segments included in the individual second segment; and determining, by the computing system, an estimate of a copy number of tumor cells with respect to individual second segments based on individual second quantitative measures that correspond to the individual second segments.

In some aspects, the first quantitative measures are determined based on a respective number of the polynucleotide molecules included in the sample that correspond to the individual first segments.

In some aspects, the first quantitative measures are determined based on a respective number of sequencing reads derived from the sample that correspond to the individual first segments.

In some aspects, the method includes determining, by the computing system, that a sequence representation that corresponds to an individual first segment has at least a threshold amount of homology with a target region; and determining, by the computing system, that a first quantitative measure of the individual first segment is excluded from determining the individual second coverage metrics.

In some aspects, the method includes: prior to determining the second segments: determining, by the computing system, guanine-cytosine (GC) content indicating a number of guanine nucleotides and cytosine nucleotides included in a portion of the set of off-target sequence representations corresponding to an individual first segment; determining, by the computing system, a frequency of sequence representations corresponding to a partition of GC content from a plurality of partitions of GC content in the individual first segment, each partition of GC content of the plurality of partitions of GC content corresponding to a different range of values for GC content; determining, by the computing system, an expected quantitative measure for the individual first segment based on the frequency of sequence representations corresponding to the plurality of partitions of GC content in the individual first segment; and determining, by the computing system, a GC normalized quantitative measure for the individual first segment based on the expected quantitative measure for the individual first segment.

In some aspects, the method includes determining, by the computing system, a mappability score for each sequence representation in an individual first segment, the mappability score indicating an amount of homology between a plurality of portions of the human reference genome, each portion of the human reference genome of the plurality of portions of the human reference genome having at least a threshold amount of homology with an additional portion of the human reference genome of the plurality of portions of the human reference genome; determining, by the computing system, a frequency of sequence representations corresponding to a partition of mappability scores from a plurality of partitions of mappability scores in the individual first segment, each partition of mappability scores of the plurality of partitions of mappability scores corresponding to a different range of values for mappability scores; determining, by the computing system, an expected quantitative measure for the individual first segment based on the frequency of sequence representations corresponding to the plurality of partitions of mappability scores in the individual first segment; and determining, by the computing system, a mappability score-normalized quantitative measure for the individual first segment based on the expected quantitative measure for the individual first segment.

In some aspects, the method includes: obtaining, by the computing system, training sequence data indicating additional sequence representations of additional polynucleotide molecules obtained from training samples, wherein the training samples are obtained from individuals in which no copy number alterations are detected; generating, by the computing system, a number of reference aligned sequence representations by performing an additional alignment process that determines one or more of the additional sequence representations that have at least the threshold amount of homology with respect to a portion of the reference human genome; determining, by the computing system, an additional set of off-target sequence representations by identifying a portion of the number of additional aligned sequence representations that do not correspond to the target regions of the reference human genome; and determining, by the computing system, individual reference quantitative measures for the individual first segments based on a number of the additional set of off-target sequence representations included in the individual first segments.

In some aspects, the method includes: determining, by the computing system, a respective number of the on-target sequence representations included in the set of on-target sequence representations that correspond to individual target regions; and determining, by the computing system, individual further quantitative measures for individual target regions based on the respective number of the on-target sequence representations that correspond to the individual target regions; wherein the estimate of the copy number of tumor cells related to the sample is based on the individual further quantitative measures.

In some aspects, the second segments of the reference human genome are determined based on the individual additional quantitative measures that correspond to the individual target regions.

In some aspects, the first quantitative measures include first size distribution metrics for the individual first segment, at least one of the first normalized quantitative measures or the second normalized quantitative measures correspond to normalized size distribution metrics, the reference quantitative measure is a reference size distribution metric, and the second quantitative measures include second size distribution metrics for the individual second segments.

In some aspects, the method includes determining, by the computing system, a number of nucleotides included in individual sequence representations that correspond to individual first segments to generate individual size distribution metrics for sequence representations of the individual first segments, wherein a size distribution includes a plurality of partitions that each correspond to a respective range of sizes of sequence representations and an individual size distribution metric for an individual first segment indicates a number of the set of off-target sequence representations included in the first segment that correspond to each partition of the plurality of partitions; determining, by the computing system, the normalized size distribution metrics for the individual first segments according to the individual first size distribution metrics with respect to a reference size distribution metric; determining, by the computing system, the second size distribution metrics for the individual second segments based on the normalized size distribution metrics of the respective plurality of individual first segments included in the individual second segment; and determining, by the computing system, an additional estimate of the copy number of tumor cells with respect to individual second segments based on the individual second size distribution metrics that correspond to the individual second segments.

In some aspects, the first quantitative measures include first coverage metrics for individual first segments, the first normalized quantitative measures correspond to first normalized coverage metrics, the second normalized quantitative measures correspond to second normalized coverage metrics, the reference quantitative measure is a reference coverage metric, and the second quantitative measures include second coverage metrics for the individual second segments.

In some aspects, the method includes determining, by the computing system, a number of the sequence representations that correspond to individual first segments to generate the individual first coverage metrics for the individual first segments; determining, by the computing system, the first normalized coverage metrics for the individual first segments according to the individual first coverage metrics; determining, by the computing system, the second normalized coverage metrics for the individual first segments according to the individual first coverage metrics with respect to the reference coverage metric; and determining, by the computing system, the second coverage metrics for the individual second segments based on the first normalized coverage metrics and the second normalized coverage metrics; wherein the estimate of the copy number of tumor cells with respect to individual second segments is based on the individual second coverage metrics that correspond to the individual second segments.

In some aspects, the estimate of the copy number of tumor cells with respect to individual second segments is based on the individual second coverage metrics that correspond to the individual second segments.

In some aspects, the quantitative measures include first size distribution metrics and first coverage metrics for individual first segments; the first normalized quantitative measures and the second normalized quantitative measures correspond to at least one of normalized size distribution metrics or normalized coverage metrics; the reference quantitative measure includes a reference size distribution metric and a reference coverage metric; and the second quantitative measures include second size distribution metrics and second coverage metrics for the individual second segments.

In some aspects, the method includes determining, by the computing system, a size of individual sequence representations by determining a number of nucleotides included in the individual sequence representations that correspond to individual first segments; generating, by the computing system, the first size distribution metrics for the individual first segments based on the respective sizes of the individual sequence representations, wherein a size distribution includes a plurality of partitions that each correspond to a respective range of sizes of sequence representations and an individual size distribution metric for an individual first segment indicates a number of the set of off-target sequence representations included in the first segment that correspond to each partition of the plurality of partitions; determining, by the computing system, the normalized size distribution metrics for the individual first segments according to the individual first size distribution metrics with respect to the reference size distribution metric; and determining, by the computing system, the second size distribution metrics for the individual second segments based on the normalized size distribution metrics of the respective plurality of individual first segments included in the individual second segments.

In some aspects, the method includes determining, by the computing system, a number of the sequence representations that correspond to individual first segments to generate the individual first coverage metrics for the individual first segments; determining, by the computing system, the first normalized coverage metrics for the individual first segments according to the individual first coverage metrics; determining, by the computing system, the second normalized size distribution metrics for the individual first segments according to the individual first coverage metrics with respect to the reference coverage metric; and determining, by the computing system, the second coverage metrics for the individual second segments based on the first normalized coverage metrics and the second normalized coverage metrics.

In some aspects, the estimate of the copy number of tumor cells with respect to individual second segments is an aggregate estimate of the copy number of tumor cells with respect to individual second segments that is generated, by the computing system, by determining a first estimate of the copy number of tumor cells with respect to individual second segments based on the second size distribution metrics and a second estimate of the copy number of tumor cells with respect to individual second segments based on the second coverage metrics.

In some aspects, the method includes: determining, by the computing system, a ratio of a number of wild-type alleles related to the sample with respect to a number of mutated alleles related to the sample; and determining, by the computing system, a heterozygous single nucleotide polymorphism (SNP) metric based on the ratio.

In some aspects, the method includes determining, by the computing system, an additional estimate of the tumor fraction for the sample based on the SNP metric; and determining, by the computing system, an additional estimate of the copy number of tumor cells related to the sample based on the SNP metric.

In some aspects, the method includes determining, by the computing system, parameters of a model that correspond to a likelihood function that generates the estimate of the copy number of tumor cells related to the sample; wherein the parameters of the model correspond to at least a portion of the individual estimates of the copy number of tumor cells with respect to the individual second segments and correspond to the estimate for the tumor fraction of the sample.

In some aspects, the parameters of the model correspond to one or more SNP metrics, individual SNP metrics of the one or more SNP metrics being related to a respective ratio of a number of mutant alleles with respect to a number of wild-type alleles.

In some aspects, at least a portion of the individual first segments include from about 30,000 nucleotides to about 150,000 nucleotides of the reference human genome.

In some aspects, at least a portion of the individual second segments include from at least about 1 million nucleotides to about 10 million nucleotides of the reference human genome; and the second segments are determined by one or more circular binary segmentation processes.

In some aspects, the sample is derived from tissue of the subject.

In some aspects, the sample is derived from a fluid obtained from the subject.

In some aspects, the method includes determining, by the computing system, an estimate for a tumor fraction of the sample based on the individual second quantitative metrics.

In some aspects, the estimate for the tumor fraction of the sample and the estimates of the copy number of tumor cells with respect to individual second segments is determined based on: observed quantitative measures=2*(1−TF)+n*TF, where n is the tumor cell copy number and TF is the tumor fraction of the sample; and wherein the observed quantitative measures include at least a portion of the second quantitative measures.

In some aspects, the method includes determining, by the computing system, a number of the sequence representations that correspond to individual first segments and that correspond to one or more single nucleotide polymorphisms (SNPs); and determining, by the computing system, a mutant allele fraction for an individual SNP based on the number of sequence representations that correspond to the individual SNP.

In some aspects, the second segments of the reference human genome are determined based on the mutant allele fractions for the individual first segments.

In some aspects, the one or more SNPs correspond to heterozygous germline SNPs.

In some aspects, the one or more SNPs correspond to driver mutations for one or more types of cancer.

In some aspects, the method includes performing, by the computing system, a first implementation of a circular binary segmentation process based on the second normalized quantitative measures to determine a first estimate of the second segments of the reference human genome; and performing, by the computing system, a second implementation of the circular binary segmentation process based on the mutant allele fractions of the individual first segments to determine a second estimate of the second segments of the reference human genome.

In some aspects, a computing system includes: one or more hardware processors; and one or more non-transitory computer-readable storage media including computer-readable instructions that, when executed by the one or more hardware processors, cause the one or more hardware processors to perform operations comprising: obtaining sequence data indicating sequence representations related to polynucleotide molecules included in a sample; generating a set of aligned sequence representations by performing an alignment process that determines one or more of the sequence representations that have at least a threshold amount of homology with respect to a portion of a reference human genome; determining a set of off-target sequence representations by identifying a first portion of the number of aligned sequence representations that do not correspond to target regions of the reference human genome; determining a set of on-target sequence representations by identifying a second portion of the number of aligned sequence representations that correspond to the target regions of the reference human genome; determining first segments of the reference human genome, wherein the first segments do not include the target regions; determining first quantitative measures for individual first segments based on a respective subset of the set of off-target sequence representations corresponding to the individual first segments; determining first normalized quantitative measures for individual first segments with respect to an additional quantitative measure of the individual first segments; determining second normalized quantitative measures for individual first segments by adjusting individual first normalized quantitative measures with respect to a reference quantitative measure for the individual first segments; determining second segments of the reference human genome, individual second segments including a greater number of nucleotides than the individual first segments and including a plurality of the individual first segments; determining second quantitative measures for individual second segments based on the first normalized quantitative measures and the second normalized quantitative measures of the respective plurality of individual first segments included in the individual second segment; and determining an estimate of a copy number of tumor cells with respect to individual second segments based on individual second quantitative measures that correspond to the individual second segments.

In some aspects, the first quantitative measures are determined based on a respective number of the polynucleotide molecules included in the sample that correspond to the individual first segments.

In some aspects, the first quantitative measures are determined based on a respective number of sequencing reads derived from the sample that correspond to the individual first segments.

In some aspects, the additional quantitative measure corresponds to a median number of sequence representations for the first segments.

In some aspects, the one or more non-transitory computer-readable storage media of the computing system include additional computer-readable instructions that, when executed by the one or more hardware processors, cause the one or more hardware processors to perform additional operations comprising: prior to determining the second segments: determining a mappability score for each sequence representation in an individual first segment, the mappability score indicating an amount of homology between a plurality of portions of the human reference genome, each portion of the human reference genome of the plurality of portions of the human reference genome having at least a threshold amount of homology with an additional portion of the human reference genome of the plurality of portions of the human reference genome; determining a frequency of sequence representations corresponding to a partition of mappability scores from a plurality of partitions of mappability scores in the individual first segment, each partition of mappability scores of the plurality of partitions of mappability scores corresponding to a different range of values for mappability scores; determining an expected quantitative measure for the individual first segment based on the frequency of sequence representations corresponding to the plurality of partitions of mappability scores in the individual first segment; and determining a mappability score-normalized quantitative measure for the individual first segment based on the expected quantitative measure for the individual first segment.

In some aspects, the one or more non-transitory computer-readable storage media of the computing system include additional computer-readable instructions that, when executed by the one or more hardware processors, cause the one or more hardware processors to perform additional operations comprising: prior to determining the second segments: determining guanine-cytosine (GC) content indicating a number of guanine nucleotides and cytosine nucleotides included in a portion of the set of off-target sequence representations corresponding to an individual first segment; determining a frequency of sequence representations corresponding to a partition of GC content from a plurality of partitions of GC content in the individual first segment, each partition of GC content of the plurality of partitions of GC content corresponding to a different range of values for GC content; determining an expected quantitative measure for the individual first segment based on the frequency of sequence representations corresponding to the plurality of partitions of GC content in the individual first segment; and determining a GC normalized quantitative measure for the individual first segment based on the expected quantitative measure for the individual first segment.

In some aspects, the one or more non-transitory computer-readable storage media of the computing system include additional computer-readable instructions that, when executed by the one or more hardware processors, cause the one or more hardware processors to perform additional operations comprising: determining that a sequence representation that corresponds to an individual first segment has at least a threshold amount of homology with a target region; and determining that a first quantitative measure of the individual first segment is excluded from determining the individual second coverage metrics.

In some aspects, the one or more non-transitory computer-readable storage media of the computing system include additional computer-readable instructions that, when executed by the one or more hardware processors, cause the one or more hardware processors to perform additional operations comprising: obtaining training sequence data indicating additional sequence representations of additional polynucleotide molecules obtained from training samples, wherein the training samples are obtained from individuals in which no copy number alterations are detected; generating a number of reference aligned sequence representations by performing an additional alignment process that determines one or more of the additional sequence representations that have at least the threshold amount of homology with respect to a portion of the reference human genome; determining an additional set of off-target sequence representations by identifying a portion of the number of additional aligned sequence representations that do not correspond to the target regions of the reference human genome; and determining individual reference quantitative measures for the individual first segments based on a number of the additional set of off-target sequence representations included in the individual first segments.

In some aspects, the one or more non-transitory computer-readable storage media of the computing system include additional computer-readable instructions that, when executed by the one or more hardware processors, cause the one or more hardware processors to perform additional operations comprising: determining a respective number of the on-target sequence representations included in the set of on-target sequence representations that correspond to individual target regions; and determining individual further quantitative measures for individual target regions based on the respective number of the on-target sequence representations that correspond to the individual target regions; wherein the estimate of the copy number of tumor cells related to the sample is based on the individual further quantitative measures.

In some aspects, the second segments of the reference human genome are determined based on the individual additional quantitative measures that correspond to the individual target regions.

In some aspects, the first quantitative measures include first size distribution metrics for the individual first segment, at least one of the first normalized quantitative measures or the second normalized quantitative measures correspond to normalized size distribution metrics, the reference quantitative measure is a reference size distribution metric, and the second quantitative measures include second size distribution metrics for the individual second segments.

In some aspects, the one or more non-transitory computer-readable storage media of the computing system include additional computer-readable instructions that, when executed by the one or more hardware processors, cause the one or more hardware processors to perform additional operations comprising: determining a number of nucleotides included in individual sequence representations that correspond to individual first segments to generate individual size distribution metrics for sequence representations of the individual first segments, wherein a size distribution includes a plurality of partitions that each correspond to a respective range of sizes of sequence representations and an individual size distribution metric for an individual first segment indicates a number of the set of off-target sequence representations included in the first segment that correspond to each partition of the plurality of partitions; determining the normalized size distribution metrics for the individual first segments according to the individual first size distribution metrics with respect to a reference size distribution metric; determining the second size distribution metrics for the individual second segments based on the normalized size distribution metrics of the respective plurality of individual first segments included in the individual second segment; and determining an additional estimate of the copy number of tumor cells with respect to individual second segments based on the individual second size distribution metrics that correspond to the individual second segments.

In some aspects, the first quantitative measures include first coverage metrics for individual first segments, the first normalized quantitative measures correspond to first normalized coverage metrics, the second normalized quantitative measures correspond to second normalized coverage metrics, the reference quantitative measure is a reference coverage metric, and the second quantitative measures include second coverage metrics for the individual second segments.

In some aspects, the one or more non-transitory computer-readable storage media of the computing system include additional computer-readable instructions that, when executed by the one or more hardware processors, cause the one or more hardware processors to perform additional operations comprising: determining a number of the sequence representations that correspond to individual first segments to generate the individual first coverage metrics for the individual first segments; determining the first normalized coverage metrics for the individual first segments according to the individual first coverage metrics; determining the second normalized coverage metrics for the individual first segments according to the individual first coverage metrics with respect to the reference coverage metric; and determining the second coverage metrics for the individual second segments based on the first normalized coverage metrics and the second normalized coverage metrics; wherein the estimate of the copy number of tumor cells with respect to individual second segments is based on the individual second coverage metrics that correspond to the individual second segments.

In some aspects, the quantitative measures include first size distribution metrics and first coverage metrics for individual first segments; the first normalized quantitative measures and the second normalized quantitative measures correspond to at least one of normalized size distribution metrics or normalized coverage metrics; the reference quantitative measure includes a reference size distribution metric and a reference coverage metric; and the second quantitative measures include second size distribution metrics and second coverage metrics for the individual second segments.

In some aspects, the one or more non-transitory computer-readable storage media of the computing system include additional computer-readable instructions that, when executed by the one or more hardware processors, cause the one or more hardware processors to perform additional operations comprising: determining a size of individual sequence representations by determining a number of nucleotides included in the individual sequence representations that correspond to individual first segments; generating the first size distribution metrics for the individual first segments based on the respective sizes of the individual sequence representations, wherein a size distribution includes a plurality of partitions that each correspond to a respective range of sizes of sequence representations and an individual size distribution metric for an individual first segment indicates a number of the set of off-target sequence representations included in the first segment that correspond to each partition of the plurality of partitions; determining the normalized size distribution metrics for the individual first segments according to the individual first size distribution metrics with respect to the reference size distribution metric; and determining the second size distribution metrics for the individual second segments based on the normalized size distribution metrics of the respective plurality of individual first segments included in the individual second segments.

In some aspects, the one or more non-transitory computer-readable storage media of the computing system include additional computer-readable instructions that, when executed by the one or more hardware processors, cause the one or more hardware processors to perform additional operations comprising: determining a number of the sequence representations that correspond to individual first segments to generate the individual first coverage metrics for the individual first segments; determining the first normalized coverage metrics for the individual first segments according to the individual first coverage metrics; determining the second normalized size distribution metrics for the individual first segments according to the individual first coverage metrics with respect to the reference coverage metric; and determining the second coverage metrics for the individual second segments based on the first normalized coverage metrics and the second normalized coverage metrics.

In some aspects, the estimate of the copy number of tumor cells with respect to individual second segments is an aggregate estimate of the copy number of tumor cells with respect to individual second segments that is generated, by the computing system, by determining a first estimate of the copy number of tumor cells with respect to individual second segments based on the second size distribution metrics and a second estimate of the copy number of tumor cells with respect to individual second segments based on the second coverage metrics.

In some aspects, the one or more non-transitory computer-readable storage media of the computing system include additional computer-readable instructions that, when executed by the one or more hardware processors, cause the one or more hardware processors to perform additional operations comprising: determining a ratio of a number of wild-type alleles related to the sample with respect to a number of mutated alleles related to the sample; and determining a heterozygous single nucleotide polymorphism (SNP) metric based on the ratio.

In some aspects, the one or more non-transitory computer-readable storage media of the computing system include additional computer-readable instructions that, when executed by the one or more hardware processors, cause the one or more hardware processors to perform additional operations comprising: determining an additional estimate of the tumor fraction for the sample based on the SNP metric; and determining an additional estimate of the copy number of tumor cells related to the sample based on the SNP metric.

In some aspects, the one or more non-transitory computer-readable storage media of the computing system include additional computer-readable instructions that, when executed by the one or more hardware processors, cause the one or more hardware processors to perform additional operations comprising: determining parameters of a model that correspond to a likelihood function that generates the estimate of the copy number of tumor cells related to the sample; wherein the parameters of the model correspond to at least a portion of the individual estimates of the copy number of tumor cells with respect to the individual second segments and correspond to the estimate for the tumor fraction of the sample.

In some aspects, the parameters of the model correspond to one or more SNP metrics, individual SNP metrics of the one or more SNP metrics being related to a respective ratio of a number of mutant alleles with respect to a number of wild-type alleles.

In some aspects, at least a portion of the individual first segments include from about 30,000 nucleotides to about 150,000 nucleotides of the reference human genome.

In some aspects, at least a portion of the individual second segments include from at least about 1 million nucleotides to about 10 million nucleotides of the reference human genome; and the second segments are determined by one or more circular binary segmentation processes.

In some aspects, the sample is derived from tissue of the subject.

In some aspects, the sample is derived from a fluid obtained from the subject.

In some aspects, the one or more non-transitory computer-readable storage media of the computing system include additional computer-readable instructions that, when executed by the one or more hardware processors, cause the one or more hardware processors to perform additional operations comprising: determining an estimate for a tumor fraction of the sample based on the individual second quantitative metrics.

In some aspects, the estimate for the tumor fraction of the sample and the estimates of the copy number of tumor cells with respect to individual second segments is determined based on: observed quantitative measures=2*(1−TF)+n*TF, where n is the tumor cell copy number and TF is the tumor fraction of the sample; and wherein the observed quantitative measures include at least a portion of the second quantitative measures.

In some aspects, the one or more non-transitory computer-readable storage media of the computing system include additional computer-readable instructions that, when executed by the one or more hardware processors, cause the one or more hardware processors to perform additional operations comprising: determining, by the computing system, a number of the sequence representations that correspond to individual first segments and that correspond to one or more single nucleotide polymorphisms (SNPs); and determining, by the computing system, a mutant allele fraction for an individual SNP based on the number of sequence representations that correspond to the individual SNP.

In some aspects, the second segments of the reference human genome are determined based on the mutant allele fractions for the individual first segments.

In some aspects, the one or more SNPs correspond to heterozygous germline SNPs.

In some aspects, the one or more SNPs correspond to driver mutations for one or more types of cancer.

In some aspects, the one or more non-transitory computer-readable storage media of the computing system include additional computer-readable instructions that, when executed by the one or more hardware processors, cause the one or more hardware processors to perform additional operations comprising: performing, by the computing system, a first implementation of a circular binary segmentation process based on the second normalized quantitative measures to determine a first estimate of the second segments of the reference human genome; and performing, by the computing system, a second implementation of the circular binary segmentation process based on the mutant allele fractions of the individual first segments to determine a second estimate of the second segments of the reference human genome.

In some aspects, one or more computer-readable storage media comprise computer-readable instructions that, when executed by one or more processors of a computing system, cause the computing system to perform operations comprising: obtaining sequence data indicating sequence representations related to polynucleotide molecules included in a sample; generating a set of aligned sequence representations by performing an alignment process that determines one or more of the sequence representations that have at least a threshold amount of homology with respect to a portion of a reference human genome; determining a set of off-target sequence representations by identifying a first portion of the number of aligned sequence representations that do not correspond to target regions of the reference human genome; determining a set of on-target sequence representations by identifying a second portion of the number of aligned sequence representations that correspond to the target regions of the reference human genome; determining first segments of the reference human genome, wherein the first segments do not include the target regions; determining first quantitative measures for individual first segments based on a respective subset of the set of off-target sequence representations corresponding to the individual first segments; determining first normalized quantitative measures for individual first segments with respect to an additional quantitative measure of the individual first segments; determining second normalized quantitative measures for individual first segments by adjusting individual first normalized quantitative measures with respect to a reference quantitative measure for the individual first segments; determining second segments of the reference human genome, individual second segments including a greater number of nucleotides than the individual first segments and including a plurality of the individual first segments; determining second quantitative measures for individual second segments based on the first normalized quantitative measures and the second normalized quantitative measures of the respective plurality of individual first segments included in the individual second segment; and determining an estimate of a copy number of tumor cells with respect to individual second segments based on individual second quantitative measures that correspond to the individual second segments.

In some aspects, the first quantitative measures are determined based on a respective number of the polynucleotide molecules included in the sample that correspond to the individual first segments.

In some aspects, the first quantitative measures are determined based on a respective number of sequencing reads derived from the sample that correspond to the individual first segments.

In some aspects, the additional quantitative measure corresponds to a median number of sequence representations for the first segments.

In some aspects, one or more computer-readable storage media comprise computer-readable instructions that, when executed by one or more processors of a computing system, cause the computing system to perform operations comprising: prior to determining the second segments: determining guanine-cytosine (GC) content indicating a number of guanine nucleotides and cytosine nucleotides included in a portion of the set of off-target sequence representations corresponding to an individual first segment; determining a frequency of sequence representations corresponding to a partition of GC content from a plurality of partitions of GC content in the individual first segment, each partition of GC content of the plurality of partitions of GC content corresponding to a different range of values for GC content; determining an expected quantitative measure for the individual first segment based on the frequency of sequence representations corresponding to the plurality of partitions of GC content in the individual first segment; and determining a GC normalized quantitative measure for the individual first segment based on the expected quantitative measure for the individual first segment.

In some aspects one or more computer-readable storage media comprise computer-readable instructions that, when executed by one or more processors of a computing system, cause the computing system to perform operations comprising: prior to determining the second segments: determining a mappability score for each sequence representation in an individual first segment, the mappability score indicating an amount of homology between a plurality of portions of the human reference genome, each portion of the human reference genome of the plurality of portions of the human reference genome having at least a threshold amount of homology with an additional portion of the human reference genome of the plurality of portions of the human reference genome; determining a frequency of sequence representations corresponding to a partition of mappability scores from a plurality of partitions of mappability scores in the individual first segment, each partition of mappability scores of the plurality of partitions of mappability scores corresponding to a different range of values for mappability scores; determining an expected quantitative measure for the individual first segment based on the frequency of sequence representations corresponding to the plurality of partitions of mappability scores in the individual first segment; and determining a mappability score-normalized quantitative measure for the individual first segment based on the expected quantitative measure for the individual first segment.

In some aspects, the one or more computer-readable storage media comprise computer-readable instructions that, when executed by one or more processors of a computing system, cause the computing system to perform operations comprising: determining that a sequence representation that corresponds to an individual first segment has at least a threshold amount of homology with a target region; and determining that a first quantitative measure of the individual first segment is excluded from determining the individual second coverage metrics.

In some aspects, the one or more computer-readable storage media comprise computer-readable instructions that, when executed by one or more processors of a computing system, cause the computing system to perform operations comprising: obtaining training sequence data indicating additional sequence representations of additional polynucleotide molecules obtained from training samples, wherein the training samples are obtained from individuals in which no copy number alterations are detected; generating a number of reference aligned sequence representations by performing an additional alignment process that determines one or more of the additional sequence representations that have at least the threshold amount of homology with respect to a portion of the reference human genome; determining an additional set of off-target sequence representations by identifying a portion of the number of additional aligned sequence representations that do not correspond to the target regions of the reference human genome; and determining individual reference quantitative measures for the individual first segments based on a number of the additional set of off-target sequence representations included in the individual first segments.

In some aspects, the one or more computer-readable storage media comprise computer-readable instructions that, when executed by one or more processors of a computing system, cause the computing system to perform operations comprising: determining a respective number of the on-target sequence representations included in the set of on-target sequence representations that correspond to individual target regions; and determining individual further quantitative measures for individual target regions based on the respective number of the on-target sequence representations that correspond to the individual target regions; wherein the estimate of the copy number of tumor cells related to the sample is based on the individual further quantitative measures.

In some aspects, the second segments of the reference human genome are determined based on the individual additional quantitative measures that correspond to the individual target regions.

In some aspects, the first quantitative measures include first size distribution metrics for the individual first segment, at least one of the first normalized quantitative measures or the second normalized quantitative measures correspond to normalized size distribution metrics, the reference quantitative measure is a reference size distribution metric, and the second quantitative measures include second size distribution metrics for the individual second segments.

In some aspects, the one or more computer-readable storage media comprise computer-readable instructions that, when executed by one or more processors of a computing system, cause the computing system to perform operations comprising: determining a number of nucleotides included in individual sequence representations that correspond to individual first segments to generate individual size distribution metrics for sequence representations of the individual first segments, wherein a size distribution includes a plurality of partitions that each correspond to a respective range of sizes of sequence representations and an individual size distribution metric for an individual first segment indicates a number of the set of off-target sequence representations included in the first segment that correspond to each partition of the plurality of partitions; determining the normalized size distribution metrics for the individual first segments according to the individual first size distribution metrics with respect to a reference size distribution metric; determining the second size distribution metrics for the individual second segments based on the normalized size distribution metrics of the respective plurality of individual first segments included in the individual second segment; and determining an additional estimate of the copy number of tumor cells with respect to individual second segments based on the individual second size distribution metrics that correspond to the individual second segments.

In some aspects, the first quantitative measures include first coverage metrics for individual first segments, the first normalized quantitative measures correspond to first normalized coverage metrics, the second normalized quantitative measures correspond to second normalized coverage metrics, the reference quantitative measure is a reference coverage metric, and the second quantitative measures include second coverage metrics for the individual second segments.

In some aspects, the one or more computer-readable storage media comprise computer-readable instructions that, when executed by one or more processors of a computing system, cause the computing system to perform operations comprising: determining a number of the sequence representations that correspond to individual first segments to generate the individual first coverage metrics for the individual first segments; determining the first normalized coverage metrics for the individual first segments according to the individual first coverage metrics; determining the second normalized coverage metrics for the individual first segments according to the individual first coverage metrics with respect to the reference coverage metric; and determining the second coverage metrics for the individual second segments based on the first normalized coverage metrics and the second normalized coverage metrics; wherein the estimate of the copy number of tumor cells with respect to individual second segments is based on the individual second coverage metrics that correspond to the individual second segments.

In some aspects, the estimate of the copy number of tumor cells with respect to individual second segments is based on the individual second coverage metrics that correspond to the individual second segments.

In some aspects, the quantitative measures include first size distribution metrics and first coverage metrics for individual first segments; the first normalized quantitative measures and the second normalized quantitative measures correspond to at least one of normalized size distribution metrics or normalized coverage metrics; the reference quantitative measure includes a reference size distribution metric and a reference coverage metric; and the second quantitative measures include second size distribution metrics and second coverage metrics for the individual second segments.

In some aspects, the computer-readable storage media comprise computer-readable instructions that, when executed by one or more processors of a computing system, cause the computing system to perform operations comprising: includes determining a size of individual sequence representations by determining a number of nucleotides included in the individual sequence representations that correspond to individual first segments; generating the first size distribution metrics for the individual first segments based on the respective sizes of the individual sequence representations, wherein a size distribution includes a plurality of partitions that each correspond to a respective range of sizes of sequence representations and an individual size distribution metric for an individual first segment indicates a number of the set of off-target sequence representations included in the first segment that correspond to each partition of the plurality of partitions; determining the normalized size distribution metrics for the individual first segments according to the individual first size distribution metrics with respect to the reference size distribution metric; and determining the second size distribution metrics for the individual second segments based on the normalized size distribution metrics of the respective plurality of individual first segments included in the individual second segments.

In some aspects, the computer-readable storage comprise computer-readable instructions that, when executed by one or more processors of a computing system, cause the computing system to perform operations comprising: determining a number of the sequence representations that correspond to individual first segments to generate the individual first coverage metrics for the individual first segments; determining the first normalized coverage metrics for the individual first segments according to the individual first coverage metrics; determining the second normalized size distribution metrics for the individual first segments according to the individual first coverage metrics with respect to the reference coverage metric; and determining the second coverage metrics for the individual second segments based on the first normalized coverage metrics and the second normalized coverage metrics.

In some aspects, the estimate of the copy number of tumor cells with respect to individual second segments is an aggregate estimate of the copy number of tumor cells with respect to individual second segments that is generated, by the computing system, by determining a first estimate of the copy number of tumor cells with respect to individual second segments based on the second size distribution metrics and a second estimate of the copy number of tumor cells with respect to individual second segments based on the second coverage metrics.

In some aspects, the computer-readable storage media comprise computer-readable instructions that, when executed by one or more processors of a computing system, cause the computing system to perform operations comprising: determining a ratio of a number of wild-type alleles related to the sample with respect to a number of mutated alleles related to the sample; and determining a heterozygous single nucleotide polymorphism (SNP) metric based on the ratio.

In some aspects, the computer-readable storage media comprise computer-readable instructions that, when executed by one or more processors of a computing system, cause the computing system to perform operations comprising: determining an additional estimate of the tumor fraction for the sample based on the SNP metric; and determining an additional estimate of the copy number of tumor cells related to the sample based on the SNP metric.

In some aspects, the computer-readable storage media comprise computer-readable instructions that, when executed by one or more processors of a computing system, cause the computing system to perform operations comprising: determining parameters of a model that correspond to a likelihood function that generates the estimate of the copy number of tumor cells related to the sample; wherein the parameters of the model correspond to at least a portion of the individual estimates of the copy number of tumor cells with respect to the individual second segments and correspond to the estimate for the tumor fraction of the sample.

In some aspects, the parameters of the model correspond to one or more SNP metrics, individual SNP metrics of the one or more SNP metrics being related to a respective ratio of a number of mutant alleles with respect to a number of wild-type alleles.

In some aspects, at least a portion of the individual first segments include from about 30,000 nucleotides to about 150,000 nucleotides of the reference human genome.

In some aspects, at least a portion of the individual second segments include from at least about 1 million nucleotides to about 10 million nucleotides of the reference human genome; and the second segments are determined by one or more circular binary segmentation processes.

In some aspects, the computer-readable storage media comprise computer-readable instructions that, when executed by one or more processors of a computing system, cause the computing system to perform operations comprising: determining an estimate for a tumor fraction of the sample based on the individual second quantitative metrics.

In some aspects, the estimate for the tumor fraction of the sample and the estimates of the copy number of tumor cells with respect to individual second segments is determined based on: observed quantitative measures=2*(1−TF)+n*TF, where n is the tumor cell copy number and TF is the tumor fraction of the sample; and wherein the observed quantitative measures include at least a portion of the second quantitative measures.

In some aspects, the computer-readable storage media comprise computer-readable instructions that, when executed by one or more processors of a computing system, cause the computing system to perform operations comprising: determining, by the computing system, a number of the sequence representations that correspond to individual first segments and that correspond to one or more single nucleotide polymorphisms (SNPs); and determining, by the computing system, a mutant allele fraction for an individual SNP based on the number of sequence representations that correspond to the individual SNP.

In some aspects, the second segments of the reference human genome are determined based on the mutant allele fractions for the individual first segments.

In some aspects, the one or more SNPs correspond to heterozygous germline SNPs.

In some aspects, the one or more SNPs correspond to driver mutations for one or more types of cancer.

In some aspects, the computer-readable storage media comprise computer-readable instructions that, when executed by one or more processors of a computing system, cause the computing system to perform operations comprising: performing, by the computing system, a first implementation of a circular binary segmentation process based on the second normalized quantitative measures to determine a first estimate of the second segments of the reference human genome; and performing, by the computing system, a second implementation of the circular binary segmentation process based on the mutant allele fractions of the individual first segments to determine a second estimate of the second segments of the reference human genome.

In some aspects, a method comprising: obtaining, by a computing system including one or more computing devices each having one or more processors and memory, sequence data indicating sequence representations of polynucleotide molecules included in a sample; generating, by the computing system, a number of aligned sequence representations by performing an alignment process that determines one or more sequence representations that have at least a threshold amount of homology with respect to a portion of a reference human genome; determining, by the computing system, a set of off-target sequence representations by identifying a portion of the number of aligned sequence representations that do not correspond to target regions of the reference human genome; performing, by the computing system, a plurality of segmentation processes to determine a number of segments of the reference human genome; determining, by the computing system, individual quantitative measures for individual segments of the reference human genome based on a portion of the set of off-target sequence representations corresponding to the individual segments; and determining, by the computing system, a plurality of estimates of a copy number of tumor cells related to the sample based on the individual quantitative metrics, individual estimates of the plurality of estimates of the copy number of tumor cells corresponding to an individual segment.

In some aspects, the plurality of segmentation processes include: a first segmentation process comprising determining, by the computing system, first segments of the reference human genome, wherein the first segments do not include the target regions; and a second segmentation process comprising determining, by the computing system, second segments of the reference human genome, individual second segments including a greater number of nucleotides than the individual first segments and including a plurality of the individual first segments.

In some aspects, the individual quantitative measures correspond to individual coverage metrics, and the method comprises: determining, by the computing system, individual first coverage metrics for individual first segments of the reference human genome based on a number of the set of off-target polynucleotide sequence representations included in the individual first segments; determining, by the computing system, normalized coverage metrics for individual first segments according to the individual first coverage metrics; and determining, by the computing system, individual second coverage metrics for individual second segments of the reference human genome based on the normalized coverage metrics of the respective plurality of individual segments included in the individual second segment.

In some aspects, the normalized coverage metrics are determined by: determining, by the computing system, first normalized quantitative measures for individual first segments based on the individual first coverage metrics with respect to a median number of sequence representations of the individual first segments.

In some aspects, the method includes determining, by the computing system, second normalized quantitative measures for individual first segments based on the individual coverage metrics with respect to reference coverage metrics for the individual first segments, the reference coverage metrics being determined based on samples obtained from individuals in which copy number variation is not detected; and adjusting, by the computing system, individual first normalized quantitative measures with respect to the second normalized coverage metrics for the individual first segments.

In some aspects, the estimate of the copy number of tumor cells related to the sample is based on the individual second coverage metrics.

In some aspects, the individual quantitative measures correspond to individual size distribution metrics, and the method comprises: determining, by the computing system, individual first size distribution metrics for individual first segments, wherein a size distribution includes a plurality of partitions that each correspond to a respective range of sizes of sequence representations and an individual size distribution metric for an individual first segment indicates a number of the set of off-target sequence representations included in the first segment that correspond to each partition of the plurality of partitions; determining, by the computing system, normalized size distribution metrics for individual first segments according to individual first size distribution metrics with respect to a reference size distribution metric; and determining, by the computing system, individual second size distribution metrics for individual second segments of the reference human genome based on the normalized size distribution metrics of the respective plurality of individual first segments included in the individual second segment.

In some aspects, the estimate of the copy number of tumor cells related to the sample is based on the individual second size distribution metrics.

In some aspects, the method includes determining, by the computing system, a ratio of a number of wild-type alleles related to the sample with respect to a number of mutated alleles related to the sample; and determining, by the computing system, a heterozygous single nucleotide polymorphism (SNP) metric based on the ratio.

In some aspects, the method includes determining, by the computing system, an additional estimate of the copy number of tumor cells related to the sample based on the SNP metric.

In some aspects, the method includes determining, by the computing system, an estimate for tumor fraction of the sample based on the individual quantitative measures.

In some aspects, the estimate for the copy number of tumor cells and the tumor fraction of the sample is determined based on: observed quantitative measures=2*(1−TF)+n*TF, where n is the tumor cell copy number and TF is the tumor fraction of the sample; and wherein the observed quantitative measures include at least a portion of the quantitative measures.

In some aspects, a computing system includes: one or more hardware processors; and one or more non-transitory computer-readable storage media including computer-readable instructions that, when executed by the one or more hardware processors, cause the one or more hardware processors to perform operations comprising: obtaining sequencing data indicating sequence representations of polynucleotide molecules included in a sample; generating a number of aligned sequence representations by performing an alignment process that determines one or more sequence representations that have at least a threshold amount of homology with respect to a portion of a reference human genome; determining a set of off-target sequence representations by identifying a portion of the number of aligned sequence representations that do not correspond to target regions of the reference human genome; performing a plurality of segmentation processes to determine a number of segments of the reference human genome; determining individual quantitative measures for individual segments of the reference human genome based on a portion of the set of off-target sequence representations corresponding to the individual segments; and determining a plurality of estimates of a copy number of tumor cells related to the sample based on the individual quantitative metrics, individual estimates of the plurality of estimates of the copy number of tumor cells corresponding to an individual segment.

In some aspects, the one or more non-transitory computer-readable storage media of the computing system include computer-readable instructions that, when executed by the one or more hardware processors, cause the one or more hardware processors to perform operations comprising: performing the plurality of segmentation processes by: performing a first segmentation process comprising determining first segments of the reference human genome, wherein the first segments do not include the target regions; and performing a second segmentation process comprising determining second segments of the reference human genome, individual second segments including a greater number of nucleotides than the individual first segments and including a plurality of the individual first segments.

In some aspects, the individual quantitative measures correspond to individual coverage metrics, and the one or more non-transitory computer-readable storage media of the computing system include additional computer-readable instructions that, when executed by the one or more hardware processors, cause the one or more hardware processors to perform additional operations comprising: determining the normalized coverage metrics by: determining first normalized quantitative measures for individual first segments based on the individual first coverage metrics with respect to a median number of sequence representations of the individual first segments.

In some aspects, the one or more non-transitory computer-readable storage media of the computing system include additional computer-readable instructions that, when executed by the one or more hardware processors, cause the one or more hardware processors to perform additional operations comprising: determining second normalized quantitative measures for individual first segments based on the individual coverage metrics with respect to reference coverage metrics for the individual first segments, the reference coverage metrics being determined based on samples obtained from individuals in which copy number variation is not detected; and adjusting individual first normalized quantitative measures with respect to the second normalized coverage metrics for the individual first segments.

In some aspects, the estimate of the copy number of tumor cells related to the sample is based on the individual second coverage metrics.

In some aspects, the individual quantitative measures correspond to individual size distribution metrics, and the estimate of the copy number of tumor cells related to the sample is based on the individual second size distribution metrics.

In some aspects, the one or more non-transitory computer-readable storage media of the computing system include computer-readable instructions that, when executed by the one or more hardware processors, cause the one or more hardware processors to perform operations comprising: determining a ratio of a number of wild-type alleles related to the sample with respect to a number of mutated alleles related to the sample; and determining a heterozygous single nucleotide polymorphism (SNP) metric based on the ratio.

In some aspects, the one or more non-transitory computer-readable storage media of the computing system include additional computer-readable instructions that, when executed by the one or more hardware processors, cause the one or more hardware processors to perform additional operations comprising: determining an additional estimate of the copy number of tumor cells related to the sample based on the SNP metric.

In some aspects, the one or more non-transitory computer-readable storage media of the computing system include computer-readable instructions that, when executed by the one or more hardware processors, cause the one or more hardware processors to perform operations comprising: determining an estimate for tumor fraction of the sample based on the individual quantitative measures.

In some aspects, the estimate for the copy number of tumor cells and the tumor fraction of the sample is determined based on: observed quantitative measures=2*(1−TF)+n*TF, where n is the tumor cell copy number and TF is the tumor fraction of the sample; and wherein the observed quantitative measures include at least a portion of the quantitative measures.

In some aspects, computer-readable storage media comprise computer-readable instructions that, when executed by one or more processors of a computing system, cause the computing system to perform operations comprising:

obtaining sequence data indicating sequence representations of polynucleotide molecules included in a sample; generating a number of aligned sequence representations by performing an alignment process that determines one or more sequence representations that have at least a threshold amount of homology with respect to a portion of a reference human genome; determining a set of off-target sequence representations by identifying a portion of the number of aligned sequence representations that do not correspond to target regions of the reference human genome; performing a plurality of segmentation processes to determine a number of segments of the reference human genome; determining individual quantitative measures for individual segments of the reference human genome based on a portion of the set of off-target sequence representations corresponding to the individual segments; and determining a plurality of estimates of a copy number of tumor cells related to the sample based on the individual quantitative metrics, individual estimates of the plurality of estimates of the copy number of tumor cells corresponding to an individual segment.

In some aspects, the computer-readable storage media comprise computer-readable instructions that, when executed by one or more processors of a computing system, cause the computing system to perform operations comprising: performing the plurality of segmentation processes by: performing a first segmentation process comprising determining first segments of the reference human genome, wherein the first segments do not include the target regions; and performing a second segmentation process comprising determining second segments of the reference human genome, individual second segments including a greater number of nucleotides than the individual first segments and including a plurality of the individual first segments.

In some aspects, the individual quantitative measures correspond to individual coverage metrics; and comprising additional computer-readable instructions that, when executed by the one or more processors of the computing system, cause the computing system to perform additional operations comprising: determining individual first coverage metrics for individual first segments of the reference human genome based on a number of the set of off-target polynucleotide sequence representations included in the individual first segments; determining normalized coverage metrics for individual first segments according to the individual first coverage metrics; and determining individual second coverage metrics for individual second segments of the reference human genome based on the normalized coverage metrics of the respective plurality of individual segments included in the individual second segment.

In some aspects, the computer-readable storage media comprise computer-readable instructions that, when executed by one or more processors of a computing system, cause the computing system to perform operations comprising: determining the normalized coverage metrics by: determining first normalized quantitative measures for individual first segments based on the individual first coverage metrics with respect to a median number of sequence representations of the individual first segments.

In some aspects, the computer-readable storage media comprise computer-readable instructions that, when executed by one or more processors of a computing system, cause the computing system to perform operations comprising: determining second normalized quantitative measures for individual first segments based on the individual coverage metrics with respect to reference coverage metrics for the individual first segments, the reference coverage metrics being determined based on samples obtained from individuals in which copy number variation is not detected; and adjusting individual first normalized quantitative measures with respect to the second normalized coverage metrics for the individual first segments.

In some aspects, the estimate of the copy number of tumor cells related to the sample is based on the individual second coverage metrics.

In some aspects, the individual quantitative measures correspond to individual size distribution metrics, and comprising additional computer-readable instructions that, when executed by the one or more processors of the computing system, cause the computing system to perform additional operations comprising: determining individual first size distribution metrics for individual first segments, wherein a size distribution includes a plurality of partitions that each correspond to a respective range of sizes of sequence representations and an individual size distribution metric for an individual first segment indicates a number of the set of off-target sequence representations included in the first segment that correspond to each partition of the plurality of partitions; determining normalized size distribution metrics for individual first segments according to individual first size distribution metrics with respect to a reference size distribution metric; and determining individual second size distribution metrics for individual second segments of the reference human genome based on the normalized size distribution metrics of the respective plurality of individual first segments included in the individual second segment.

In some aspects, the estimate of the copy number of tumor cells related to the sample is based on the individual second size distribution metrics.

In some aspects, the computer-readable storage media comprise computer-readable instructions that, when executed by one or more processors of a computing system, cause the computing system to perform operations comprising: determining a ratio of a number of wild-type alleles related to the sample with respect to a number of mutated alleles related to the sample; and determining a heterozygous single nucleotide polymorphism (SNP) metric based on the ratio.

In some aspects, the computer-readable storage media comprise computer-readable instructions that, when executed by one or more processors of a computing system, cause the computing system to perform operations comprising: determining an additional estimate of the copy number of tumor cells related to the sample based on the SNP metric.

In some aspects, the computer-readable storage media comprise computer-readable instructions that, when executed by one or more processors of a computing system, cause the computing system to perform operations comprising: determining an estimate for tumor fraction of the sample based on the individual quantitative measures.

In some aspects, the estimate for the copy number of tumor cells and the tumor fraction of the sample is determined based on: observed quantitative measures=2*(1−TF)+n*TF, where n is the tumor cell copy number and TF is the tumor fraction of the sample; and wherein the observed quantitative measures include at least a portion of the quantitative measures.

In some aspects, a method comprising: obtaining, by a computing system including one or more computing devices each having one or more processors and memory, sequencing data including a number of sequencing reads based on polynucleotide molecules derived from a sample; generating, by the computing system, a number of aligned sequencing reads by performing an alignment process that determines one or more portions of the number of sequencing reads that have at least a threshold amount of homology with respect to a portion of the reference human genome; determining, by the computing system, a set of off-target sequence reads by identifying a portion of the number of aligned sequence reads that do not correspond to the target regions of the reference human genome; performing, by the computing system, a plurality of segmentation processes to determine a number of segments of the reference human genome; determining, by the computing system, quantitative measures for individual segments of the reference human genome based on the set of off-target sequencing reads that correspond to the individual segments; and determining, by the computing system, a plurality of estimates of a copy number of tumor cells related to the sample based on the individual quantitative measures, individual estimates of the plurality of estimates of the copy number of tumor cells corresponding to an individual segment.

In some aspects, the plurality of segmentation processes include: a first segmentation process comprising determining, by the computing system, first segments of the reference human genome, wherein the first segments do not include the target regions; and a second segmentation process comprising determining, by the computing system, second segments of the reference human genome, individual second segments including a greater number of nucleotides than the individual first segments and including a plurality of the individual first segments.

In some aspects, the individual quantitative measures correspond to individual coverage metrics, and the method comprises: determining, by the computing system, individual first coverage metrics for individual first segments based on a number of the set of off-target sequencing reads included in the individual first segments; determining, by the computing system, normalized coverage metrics for individual first segments according to individual first coverage metrics; and determining, by the computing system, individual second coverage metrics for individual second segments based on the normalized coverage metrics of the respective plurality of individual segments included in the individual second segment.

In some aspects, the normalized coverage metrics are determined by: determining, by the computing system, first normalized quantitative measures for individual first segments based on the individual first coverage metrics with respect to a median number of sequencing reads related to the individual first segments.

In some aspects, the method includes determining, by the computing system, second normalized quantitative measures for individual first segments based on the individual coverage metrics with respect to reference coverage metrics for the individual first segments, the reference coverage metrics being determined based on samples obtained from individuals in which copy number variation is not detected; and adjusting, by the computing system, individual first normalized quantitative measures with respect to the second normalized coverage metrics for the individual first segments;

In some aspects, the estimate of the copy number of tumor cells related to the sample is based on the individual second coverage metrics.

In some aspects, the individual quantitative measures correspond to individual size distribution metrics, and the method comprises: determining, by the computing system, individual first size distribution metrics for individual first segments, wherein a size distribution includes a plurality of partitions that each correspond to a respective range of sizes of sequencing reads and an individual size distribution metric for an individual first segment indicates a number of the set of off-target sequencing reads included in the first segment that correspond to each partition of the plurality of partitions; determining, by the computing system, normalized size distribution metrics for individual first segments according to individual first size distribution metrics with respect to a reference size distribution metric; and determining, by the computing system, individual second size distribution metrics for individual second segments of the reference human genome based on the normalized size distribution metrics of the respective plurality of individual first segments included in the individual second segment.

In some aspects, the estimate of the copy number of tumor cells related to the sample is based on the individual second size distribution metrics.

In some aspects, the method includes determining, by the computing system, a ratio of a number of wild-type alleles related to the sample with respect to a number of mutated alleles related to the sample; and determining, by the computing system, a heterozygous single nucleotide polymorphism (SNP) metric based on the ratio.

In some aspects, the method includes determining, by the computing system, an additional estimate of the copy number of tumor cells related to the sample based on the SNP metric.

In some aspects, the method includes determining an estimate for tumor fraction of the sample based on the individual quantitative measures.

In some aspects, the estimate for the copy number of tumor cells and the tumor fraction of the sample is determined based on: observed quantitative measures=2*(1−TF)+n*TF, where n is the tumor cell copy number and TF is the tumor fraction of the sample; and wherein the observed quantitative measures include at least a portion of the quantitative measures.

In some aspects, a computing system includes: one or more hardware processors; and one or more non-transitory computer-readable storage media including computer-readable instructions that, when executed by the one or more hardware processors, cause the one or more hardware processors to perform operations comprising: obtaining sequencing data including a number of sequencing reads based on polynucleotide molecules derived from a sample; generating a number of aligned sequence reads by performing an alignment process that determines one or more portions of the number of sequencing reads that have at least a threshold amount of homology with respect to a portion of the reference human genome; determining a set of off-target sequence reads by identifying a portion of the number of aligned sequencing reads that do not correspond to the target regions of the reference human genome; performing a plurality of segmentation processes to determine a number of segments of the reference human genome; determining quantitative measures for individual segments of the reference human genome based on the set of off-target sequencing reads that correspond to the individual segments; and determining a plurality of estimates of a copy number of tumor cells related to the sample based on the individual quantitative measures, individual estimates of the plurality of estimates of the copy number of tumor cells corresponding to an individual segment.

In some aspects, the one or more non-transitory computer-readable storage media of the computing system include additional computer-readable instructions that, when executed by the one or more hardware processors, cause the one or more hardware processors to perform additional operations comprising: performing the plurality of segmentation processes by: performing a first segmentation process by determining first segments of the reference human genome, wherein the first segments do not include the target regions; and performing a second segmentation process by determining second segments of the reference human genome, individual second segments including a greater number of nucleotides than the individual first segments and including a plurality of the individual first segments.

In some aspects, the individual quantitative measures correspond to individual coverage metrics; and the one or more non-transitory computer-readable storage media of the computing system include additional computer-readable instructions that, when executed by the one or more hardware processors, cause the one or more hardware processors to perform additional operations comprising: determining individual first coverage metrics for individual first segments of the reference human genome based on a number of the set of off-target polynucleotide sequence representations included in the individual first segments; determining normalized coverage metrics for individual first segments according to the individual first coverage metrics; and determining individual second coverage metrics for individual second segments of the reference human genome based on the normalized coverage metrics of the respective plurality of individual segments included in the individual second segment.

In some aspects, the one or more non-transitory computer-readable storage media of the computing system include additional computer-readable instructions that, when executed by the one or more hardware processors, cause the one or more hardware processors to perform additional operations comprising: determining the normalized coverage metrics by determining first normalized quantitative measures for individual first segments based on the individual first coverage metrics with respect to a median number of sequencing reads related to the individual first segments.

In some aspects, the one or more non-transitory computer-readable storage media of the computing system include additional computer-readable instructions that, when executed by the one or more hardware processors, cause the one or more hardware processors to perform additional operations comprising: determining second normalized quantitative measures for individual first segments based on the individual coverage metrics with respect to reference coverage metrics for the individual first segments, the reference coverage metrics being determined based on samples obtained from individuals in which copy number variation is not detected; and adjusting individual first normalized quantitative measures with respect to the second normalized coverage metrics for the individual first segments.

In some aspects, the estimate of the copy number of tumor cells related to the sample is based on the individual second coverage metrics.

In some aspects, the individual quantitative measures correspond to individual size distribution metrics; and the one or more non-transitory computer-readable storage media include additional computer-readable instructions that, when executed by the one or more hardware processors, cause the one or more hardware processors to perform additional operations comprising: determining individual first size distribution metrics for individual first segments, wherein a size distribution includes a plurality of partitions that each correspond to a respective range of sizes of sequence representations and an individual size distribution metric for an individual first segment indicates a number of the set of off-target sequence representations included in the first segment that correspond to each partition of the plurality of partitions; determining normalized size distribution metrics for individual first segments according to individual first size distribution metrics with respect to a reference size distribution metric; and determining, by the computing system, individual second size distribution metrics for individual second segments of the reference human genome based on the normalized size distribution metrics of the respective plurality of individual first segments included in the individual second segment.

In some aspects, the estimate of the copy number of tumor cells related to the sample is based on the individual second size distribution metrics.

In some aspects, the one or more non-transitory computer-readable storage media of the computing system include additional computer-readable instructions that, when executed by the one or more hardware processors, cause the one or more hardware processors to perform additional operations comprising: determining a ratio of a number of wild-type alleles related to the sample with respect to a number of mutated alleles related to the sample; and determining a heterozygous single nucleotide polymorphism (SNP) metric based on the ratio.

In some aspects, the one or more non-transitory computer-readable storage media of the computing system include additional computer-readable instructions that, when executed by the one or more hardware processors, cause the one or more hardware processors to perform additional operations comprising: determining an additional estimate of the copy number of tumor cells related to the sample based on the SNP metric.

In some aspects, the one or more non-transitory computer-readable storage media of the computing system include additional computer-readable instructions that, when executed by the one or more hardware processors, cause the one or more hardware processors to perform additional operations comprising: determining an estimate for tumor fraction of the sample based on the individual quantitative measures.

In some aspects, the estimate for the copy number of tumor cells and the tumor fraction of the sample is determined based on: observed quantitative measures=2*(1−TF)+n*TF, where n is the tumor cell copy number and TF is the tumor fraction of the sample; and wherein the observed quantitative measures include at least a portion of the quantitative measures.

In some aspects, one or more computer-readable storage media comprising computer-readable instructions that, when executed by one or more processors of a computing system, cause the computing system to perform operations comprising: obtaining sequencing data including a number of sequencing reads based on polynucleotide molecules derived from a sample; generating a number of aligned sequencing reads by performing an alignment process that determines one or more portions of the number of sequencing reads that have at least a threshold amount of homology with respect to a portion of the reference human genome; determining a set of off-target sequence reads by identifying a portion of the number of aligned sequence reads that do not correspond to the target regions of the reference human genome; performing a plurality of segmentation processes to determine a number of segments of the reference human genome; determining quantitative measures for individual segments of the reference human genome based on the set of off-target sequencing reads that correspond to the individual segments; and determining a plurality of estimates of a copy number of tumor cells related to the sample based on the individual quantitative measures, individual estimates of the plurality of estimates of the copy number of tumor cells corresponding to an individual segment.

In some aspects, the computer-readable storage media comprise computer-readable instructions that, when executed by one or more processors of a computing system, cause the computing system to perform operations comprising: performing the plurality of segmentations processes by: performing a first segmentation process comprising determining first segments of the reference human genome, wherein the first segments do not include the target regions; and performing a second segmentation process comprising determining second segments of the reference human genome, individual second segments including a greater number of nucleotides than the individual first segments and including a plurality of the individual first segments.

In some aspects, the individual quantitative measures correspond to individual coverage metrics, and comprising additional computer-readable instructions that, when executed by the one or more processors of the computing system, cause the computing system to perform additional operations comprising: determining individual first coverage metrics for individual first segments based on a number of the set of off-target sequence reads included in the individual first segments; determining normalized coverage metrics for individual first segments according to individual first coverage metrics; and determining individual second coverage metrics for individual second segments based on the normalized coverage metrics of the respective plurality of individual segments included in the individual second segment.

In some aspects, the computer-readable storage media comprise computer-readable instructions that, when executed by one or more processors of a computing system, cause the computing system to perform operations comprising: determining the normalized coverage metrics by: determining first normalized quantitative measures for individual first segments based on the individual first coverage metrics with respect to a median number of sequence representations of the individual first segments.

In some aspects, the computer-readable storage media comprise computer-readable instructions that, when executed by one or more processors of a computing system, cause the computing system to perform operations comprising: determining second normalized quantitative measures for individual first segments based on the individual coverage metrics with respect to reference coverage metrics for the individual first segments, the reference coverage metrics being determined based on samples obtained from individuals in which copy number variation is not detected; and adjusting individual first normalized quantitative measures with respect to the second normalized coverage metrics for the individual first segments.

In some aspects, the estimate of the copy number of tumor cells related to the sample is based on the individual second coverage metrics.

In some aspects, the individual quantitative measures correspond to individual size distribution metrics, and comprising additional computer-readable instructions that, when executed by the one or more processors of the computing system, cause the computing system to perform additional operations comprising: determining individual first size distribution metrics for individual first segments, wherein a size distribution includes a plurality of partitions that each correspond to a respective range of sizes of sequence reads and an individual size distribution metric for an individual first segment indicates a number of the set of off-target sequence reads included in the first segment that correspond to each partition of the plurality of partitions; determining normalized size distribution metrics for individual first segments according to individual first size distribution metrics with respect to a reference size distribution metric; and determining individual second size distribution metrics for individual second segments of the reference human genome based on the normalized size distribution metrics of the respective plurality of individual first segments included in the individual second segment.

In some aspects, the estimate of the copy number of tumor cells related to the sample is based on the individual second size distribution metrics.

In some aspects, the computer-readable storage media comprise computer-readable instructions that, when executed by one or more processors of a computing system, cause the computing system to perform operations comprising: determining a ratio of a number of wild-type alleles related to the sample with respect to a number of mutated alleles related to the sample; and determining a heterozygous single nucleotide polymorphism (SNP) metric based on the ratio.

In some aspects, the computer-readable storage media comprise computer-readable instructions that, when executed by one or more processors of a computing system, cause the computing system to perform operations comprising: determining an additional estimate of the copy number of tumor cells related to the sample based on the SNP metric.

In some aspects, the computer-readable storage media comprise computer-readable instructions that, when executed by one or more processors of a computing system, cause the computing system to perform operations comprising: determining an estimate for tumor fraction of the sample based on the individual quantitative measures.

In some aspects, the estimate for the copy number of tumor cells and the tumor fraction of the sample is determined based on: observed quantitative measures=2*(1−TF)+n*TF, where n is the tumor cell copy number and TF is the tumor fraction of the sample; and wherein the observed quantitative measures include at least a portion of the quantitative measures.

In some aspects, a method comprising: obtaining, by a computing system including one or more computing devices each having one or more processors and memory, sequencing data indicating polynucleotide molecules included in a sample; generating, by the computing system, a number of aligned polynucleotide molecules by performing an alignment process that determines one or more polynucleotide molecules that have at least a threshold amount of homology with respect to a portion of a reference human genome; determining, by the computing system, a set of off-target polynucleotide molecules by identifying a portion of the number of aligned polynucleotide molecules that do not correspond to target regions of the reference human genome; performing, by the computing system, a plurality of segmentation processes to determine a number of segments of the reference human genome; determining, by the computing system, quantitative measures for individual segments of the reference human genome based on a portion of the set of off-target polynucleotides molecules that correspond to the individual segments; and determining, by the computing system, a plurality of estimates of a copy number of tumor cells related to the sample based on the individual quantitative measures, individual estimates of the plurality of estimates of the copy number of tumor cells corresponding to an individual segment.

In some aspects, the plurality of segmentation processes include: a first segmentation process comprising determining, by the computing system, first segments of the reference human genome, wherein the first segments do not include the target regions; and a second segmentation process comprising determining, by the computing system, second segments of the reference human genome, individual second segments including a greater number of nucleotides than the individual first segments and including a plurality of the individual first segments.

In some aspects, the individual quantitative measures correspond to individual coverage metrics, and the method comprises: determining, by the computing system, individual first coverage metrics for individual first segments based on a number of the set of off-target polynucleotide molecules included in the individual first segments; determining, by the computing system, normalized coverage metrics for individual first segments according to individual first coverage metrics; and determining, by the computing system, individual second coverage metrics for individual second segments based on the normalized coverage metrics of the respective plurality of individual segments included in the individual second segment.

In some aspects, the normalized coverage metrics are determined by: determining, by the computing system, first normalized quantitative measures for individual first segments based on the individual first coverage metrics with respect to a median number of polynucleotide molecules related to the individual first segments.

In some aspects, the method includes determining, by the computing system, second normalized quantitative measures for individual first segments based on the individual coverage metrics with respect to reference coverage metrics for the individual first segments, the reference coverage metrics being determined based on samples obtained from individuals in which copy number variation is not detected; and adjusting individual first normalized quantitative measures with respect to the second normalized coverage metrics for the individual first segments;

In some aspects, the estimate of the copy number of tumor cells related to the sample is based on the individual second coverage metrics.

In some aspects, the individual quantitative measures correspond to individual size distribution metrics, and the method comprises: determining, by the computing system, individual first size distribution metrics for individual first segments, wherein a size distribution includes a plurality of partitions that each correspond to a respective range of sizes of polynucleotide molecules and an individual size distribution metric for an individual first segment indicates a number of the set of off-target polynucleotide molecules included in the first segment that correspond to each partition of the plurality of partitions; determining, by the computing system, normalized size distribution metrics for individual first segments according to individual first size distribution metrics with respect to a reference size distribution metric; and determining, by the computing system, individual second size distribution metrics for individual second segments of the reference human genome based on the normalized size distribution metrics of the respective plurality of individual first segments included in the individual second segment.

In some aspects, the estimate of the copy number of tumor cells related to the sample is based on the individual second size distribution metrics.

In some aspects, the estimate of the copy number of tumor cells related to the sample is based on the individual second size distribution metrics.

In some aspects, the method comprises: determining, by the computing system, a ratio of a number of wild-type alleles related to the sample with respect to a number of mutated alleles related to the sample; and determining, by the computing system, a heterozygous single nucleotide polymorphism (SNP) metric based on the ratio.

In some aspects, the method includes determining, by the computing system, an additional estimate of the copy number of tumor cells related to the sample based on the SNP metric.

In some aspects, the method includes: determining, by the computing system, an estimate for tumor fraction of the sample based on the individual quantitative measures.

In some aspects, the estimate for copy number of tumor cells and the tumor fraction of the sample is determined based on: observed quantitative measures=2*(1−TF)+n*TF, where n is the tumor cell copy number and TF is the tumor fraction of the sample; and wherein the observed quantitative measures include at least a portion of the quantitative measures.

In some aspects, a computing system comprising: one or more hardware processors; and one or more non-transitory computer-readable storage media including computer-readable instructions that, when executed by the one or more hardware processors, cause the one or more hardware processors to perform operations comprising: obtaining sequencing data indicating polynucleotide molecules included in a sample; generating a number of aligned polynucleotide molecules by performing an alignment process that determines one or more polynucleotide molecules that have at least a threshold amount of homology with respect to a portion of a reference human genome; determining a set of off-target polynucleotide molecules by identifying a portion of the number of aligned polynucleotide molecules that do not correspond to target regions of the reference human genome; performing a plurality of segmentation processes to determine a number of segments of the reference human genome; determining quantitative measures for individual segments of the reference human genome based on a portion of the set of off-target polynucleotides molecules that correspond to the individual segments; and determining a plurality of estimates of a copy number of tumor cells related to the sample based on the individual quantitative measures, individual estimates of the plurality of estimates of the copy number of tumor cells corresponding to an individual segment.

In some aspects, the one or more non-transitory computer-readable storage media of the computing system include additional computer-readable instructions that, when executed by the one or more hardware processors, cause the one or more hardware processors to perform additional operations comprising: performing the plurality of segmentation processes by: performing a first segmentation process comprising determining first segments of the reference human genome, wherein the first segments do not include the target regions; and performing a second segmentation process comprising determining second segments of the reference human genome, individual second segments including a greater number of nucleotides than the individual first segments and including a plurality of the individual first segments.

In some aspects, the individual quantitative measures correspond to individual coverage metrics, and the one or more non-transitory computer-readable storage media include additional computer-readable instructions that, when executed by the one or more hardware processors, cause the one or more hardware processors to perform additional operations comprising: determining individual first coverage metrics for individual first segments based on a number of the set of off-target polynucleotide molecules included in the individual first segments; determining, by the computing system, normalized coverage metrics for individual first segments according to individual first coverage metrics; and determining individual second coverage metrics for individual second segments based on the normalized coverage metrics of the respective plurality of individual segments included in the individual second segment.

In some aspects, the one or more non-transitory computer-readable storage media of the computing system include additional computer-readable instructions that, when executed by the one or more hardware processors, cause the one or more hardware processors to perform additional operations comprising: determining the normalized coverage metrics by: determining first normalized quantitative measures for individual first segments based on the individual first coverage metrics with respect to a median number of polynucleotide molecules related to the individual first segments.

In some aspects, the one or more non-transitory computer-readable storage media of the computing system include additional computer-readable instructions that, when executed by the one or more hardware processors, cause the one or more hardware processors to perform additional operations comprising: determining second normalized quantitative measures for individual first segments based on the individual coverage metrics with respect to reference coverage metrics for the individual first segments, the reference coverage metrics being determined based on samples obtained from individuals in which copy number variation is not detected; and adjusting individual first normalized quantitative measures with respect to the second normalized coverage metrics for the individual first segments;

In some aspects, the estimate of the copy number of tumor cells related to the sample is based on the individual second coverage metrics.

In some aspects, the individual quantitative measures correspond to individual size distribution metrics; and the one or more non-transitory computer-readable storage media include additional computer-readable instructions that, when executed by the one or more hardware processors, cause the one or more hardware processors to perform additional operations comprising: determining individual first size distribution metrics for individual first segments, wherein a size distribution includes a plurality of partitions that each correspond to a respective range of sizes of polynucleotide molecules and an individual size distribution metric for an individual first segment indicates a number of the set of off-target polynucleotide molecules included in the first segment that correspond to each partition of the plurality of partitions; determining normalized size distribution metrics for individual first segments according to individual first size distribution metrics with respect to a reference size distribution metric; and determining, by the computing system, individual second size distribution metrics for individual second segments of the reference human genome based on the normalized size distribution metrics of the respective plurality of individual first segments included in the individual second segment.

In some aspects, the estimate of the copy number of tumor cells related to the sample is based on the individual second size distribution metrics.

In some aspects, the one or more non-transitory computer-readable storage media of the computing system include additional computer-readable instructions that, when executed by the one or more hardware processors, cause the one or more hardware processors to perform additional operations comprising: determining a ratio of a number of wild-type alleles related to the sample with respect to a number of mutated alleles related to the sample; and determining a heterozygous single nucleotide polymorphism (SNP) metric based on the ratio.

In some aspects, the one or more non-transitory computer-readable storage media of the computing system include additional computer-readable instructions that, when executed by the one or more hardware processors, cause the one or more hardware processors to perform additional operations comprising: determining an additional estimate of the copy number of tumor cells related to the sample based on the SNP metric.

In some aspects, the one or more non-transitory computer-readable storage media of the computing system include additional computer-readable instructions that, when executed by the one or more hardware processors, cause the one or more hardware processors to perform additional operations comprising: determining an estimate for tumor fraction of the sample based on the individual quantitative measures.

In some aspects, the estimate for copy number of tumor cells and the tumor fraction of the sample is determined based on: observed quantitative measures=2*(1−TF)+n*TF, where n is the tumor cell copy number and TF is the tumor fraction of the sample; and wherein the observed quantitative measures include at least a portion of the quantitative measures.

In some aspects, one or more computer-readable storage media comprising computer-readable instructions that includes: obtaining sequencing data indicating polynucleotide molecules included in a sample; generating a number of aligned polynucleotide molecules by performing an alignment process that determines one or more polynucleotide molecules that have at least a threshold amount of homology with respect to a portion of a reference human genome; determining a set of off-target polynucleotide molecules by identifying a portion of the number of aligned polynucleotide molecules that do not correspond to target regions of the reference human genome; performing a plurality of segmentation processes to determine a number of segments of the reference human genome; determining quantitative measures for individual segments of the reference human genome based on a portion of the set of off-target polynucleotides molecules that correspond to the individual segments; and determining a plurality of estimates of a copy number of tumor cells related to the sample based on the individual quantitative measures, individual estimates of the plurality of estimates of the copy number of tumor cells corresponding to an individual segment.

In some aspects, the computer-readable storage media comprise computer-readable instructions that, when executed by one or more processors of a computing system, cause the computing system to perform operations comprising: performing the plurality of segmentation by: performing a first segmentation process by determining first segments of the reference human genome, wherein the first segments do not include the target regions; and performing a second segmentation process by determining second segments of the reference human genome, individual second segments including a greater number of nucleotides than the individual first segments and including a plurality of the individual first segments.

In some aspects, the individual quantitative measures correspond to individual coverage metrics, and comprising additional computer-readable instructions that, when executed by one or more processors of a computing system, cause the computing system to perform additional operations comprising: determining individual first coverage metrics for individual first segments based on a number of the set of off-target polynucleotide molecules included in the individual first segments; determining normalized coverage metrics for individual first segments according to individual first coverage metrics; and determining individual second coverage metrics for individual second segments based on the normalized coverage metrics of the respective plurality of individual segments included in the individual second segment.

In some aspects, the computer-readable storage media comprise computer-readable instructions that, when executed by one or more processors of a computing system, cause the computing system to perform operations comprising: determining the normalized coverage metrics by: determining first normalized quantitative measures for individual first segments based on the individual first coverage metrics with respect to a median number of polynucleotide molecules related to the individual first segments.

In some aspects, the computer-readable storage media comprise computer-readable instructions that, when executed by one or more processors of a computing system, cause the computing system to perform operations comprising: determining second normalized quantitative measures for individual first segments based on the individual coverage metrics with respect to reference coverage metrics for the individual first segments, the reference coverage metrics being determined based on samples obtained from individuals in which copy number variation is not detected; and adjusting individual first normalized quantitative measures with respect to the second normalized coverage metrics for the individual first segments;

In some aspects, the estimate of the copy number of tumor cells related to the sample is based on the individual second coverage metrics.

In some aspects, the individual quantitative measures correspond to individual size distribution metrics, and comprising additional computer-readable instructions that, when executed by one or more processors of a computing system, cause the computing system to perform additional operations comprising: determining individual first size distribution metrics for individual first segments, wherein a size distribution includes a plurality of partitions that each correspond to a respective range of sizes of polynucleotide molecules and an individual size distribution metric for an individual first segment indicates a number of the set of off-target polynucleotide molecules included in the first segment that correspond to each partition of the plurality of partitions; determining normalized size distribution metrics for individual first segments according to individual first size distribution metrics with respect to a reference size distribution metric; and determining individual second size distribution metrics for individual second segments of the reference human genome based on the normalized size distribution metrics of the respective plurality of individual first segments included in the individual second segment.

In some aspects, the computer-readable storage media comprise computer-readable instructions that, when executed by one or more processors of a computing system, cause the computing system to perform operations comprising: determining a ratio of a number of wild-type alleles related to the sample with respect to a number of mutated alleles related to the sample; and determining a heterozygous single nucleotide polymorphism (SNP) metric based on the ratio.

In some aspects, the computer-readable storage media comprise computer-readable instructions that, when executed by one or more processors of a computing system, cause the computing system to perform operations comprising: determining an additional estimate of the copy number of tumor cells related to the sample based on the SNP metric.

In some aspects, the one or more computer-readable storage media of comprise computer-readable instructions that, when executed by one or more processors of a computing system, cause the computing system to perform operations comprising: determining an estimate for tumor fraction of the sample based on the individual quantitative measures.

In some aspects, the estimate for copy number of tumor cells and the tumor fraction of the sample is determined based on: observed quantitative measures=2*(1−TF)+n*TF, where n is the tumor cell copy number and TF is the tumor fraction of the sample; and wherein the observed quantitative measures includes at least a portion of the quantitative measures.

Definitions

In order for the present disclosure to be more readily understood, certain terms are first defined below. Additional definitions for the following terms and other terms may be set forth through the specification. If a definition of a term set forth below is inconsistent with a definition in an application or patent that is incorporated by reference, the definition set forth in this application should be used to understand the meaning of the term.

As used in this specification and the appended claims, the singular forms “a,” “an,” and “the” include plural references unless the context clearly dictates otherwise. Thus, for example, a reference to “a method” includes one or more methods, and/or steps of the type described herein and/or which will become apparent to those persons of ordinary skill in the art upon reading this disclosure and so forth.

It is also to be understood that the terminology used herein is for the purpose of describing particular implementations only, and is not intended to be limiting. Further, unless defined otherwise, all technical and scientific terms used herein have the same meaning as commonly understood by one of ordinary skill in the art to which this disclosure pertains. In describing and claiming the methods, computer readable media, and systems, the following terminology, and grammatical variants thereof, will be used in accordance with the definitions set forth below.

About: As used herein, “about” or “approximately” as applied to one or more values or elements of interest, refers to a value or element that is similar to a stated reference value or element. In certain implementations, the term “about” or “approximately” refers to a range of values or elements that falls within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value or element unless otherwise stated or otherwise evident from the context (except where such number would exceed 100% of a possible value or element).

Administer: As used herein, "administer" or "administering" a therapeutic agent (e.g., an immunological therapeutic agent) to a subject means to give, apply or bring the composition into contact with the subject. Administration can be accomplished by any of a number of routes, including, for example, topical, oral, subcutaneous, intramuscular, intraperitoneal, intravenous, intrathecal and intradermal.

Adapter. As used herein, "adapter" refers to a short nucleic acid (e.g., less than about 500 nucleotides, less than about 100 nucleotides, or less than about 50 nucleotides in length) that can be at least partially double-stranded and used to link to either or both ends of a given sample nucleic acid molecule. Adapters can include nucleic acid primer binding sites to permit amplification of a nucleic acid molecule flanked by adapters at both ends, and/or a sequencing primer binding site, including primer binding sites for sequencing applications, such as various next-generation sequencing (NGS) applications. Adapters can also include binding sites for capture probes, such as an oligonucleotide attached to a flow cell support or the like. Adapters can also include a nucleic acid tag as described herein. Nucleic acid tags can be positioned relative to amplification primer and sequencing primer binding sites, such that a nucleic acid tag is included in amplicons and sequence reads of a given nucleic acid molecule. The same or different adapters can be linked to the respective ends of a nucleic acid molecule. In some implementations, the same adapter is linked to the respective ends of the nucleic acid molecule except that the nucleic acid tag differs. In some implementations, the adapter is a Y-shaped adapter in which one end is blunt ended or tailed as described herein, for joining to a nucleic acid molecule, which is also blunt ended or tailed with one or more complementary nucleotides. In still other example implementations, an adapter is a bell-shaped adapter that includes a blunt or tailed end for joining to a nucleic acid molecule to be analyzed. Other examples of adapters include T-tailed and C-tailed adapters.

Alignment: As used herein, "alignment" or "align" refers to determining whether at least two sequence representations have at least a threshold amount of homology. In one or more examples, the threshold amount of homology can be at least about 90%, at least about 91%, at least about 92%, at least about 93%, at least about 94%, at least about 95%, at least about 96%, at least about 97%, at least about 98%, at least about 99%, at least about 99.5%, or at least about 99.9%. In situations where two sequence representations have at least the threshold amount of homology, the two sequence representations can be referred to as being "aligned."

Amplify: As used herein, "amplify" or "amplification" in the context of nucleic acids refers to the production of multiple copies of a polynucleotide, or a portion of the polynucleotide, starting from a small amount of the polynucleotide (e.g., a single polynucleotide molecule), where the amplification products or amplicons are generally detectable. Amplification of polynucleotides encompasses a variety of chemical and enzymatic processes.

Barcode: As used herein, "barcode" or "molecular barcode" in the context of nucleic acids refers to a nucleic acid molecule comprising a sequence that can serve as a molecular identifier. For example, individual "barcode" sequences can be added to each DNA fragment during next-generation sequencing (NGS) library preparation so that each read can be identified and sorted before the final data analysis.

Cancer Type: As used herein, "cancer type" refers to a type or subtype of cancer defined, e.g., by histopathology. Cancer type can be defined by any conventional criterion, such as on the basis of occurrence in a given tissue (e.g., blood cancers, central nervous system (CNS), brain cancers, lung cancers (small cell and non-small cell), skin cancers, nose cancers, throat cancers, liver cancers, bone cancers, lymphomas, pancreatic cancers, bowel cancers, rectal cancers, thyroid cancers, bladder cancers, kidney cancers, mouth cancers, stomach cancers, breast cancers, prostate cancers, ovarian cancers, lung cancers, intestinal cancers, soft tissue cancers, neuroendocrine cancers, gastroesophageal cancers, head and neck cancers, gynecological cancers, colorectal cancers, urothelial cancers, solid state cancers, heterogeneous cancers, homogenous cancers), unknown primary origin and the like, and/or of the same cell lineage (e.g., carcinoma, sarcoma, lymphoma, cholangiocarcinoma, leukemia, mesothelioma, melanoma, or glioblastoma) and/or cancers exhibiting cancer markers, such as Her2, CA15-3, CA19-9, CA-125, CEA, AFP, PSA, HCG, hormone receptor and NMP-22. Cancers can also be classified by stage (e.g., stage 1, 2, 3, or 4) and whether of primary or secondary origin.

Carrier Signal: As used herein, "carrier signal" refers to any intangible medium that is capable of storing, encoding, or carrying transitory or non-transitory instructions 1102 for execution by the machine 1100, and includes digital or analog communications signals or other intangible medium to facilitate communication of such instructions 1102. Instructions 1102 may be transmitted or received over the network 1134 using a transitory or non-transitory transmission medium via a network interface device and using any one of a number of well-known transfer protocols.

Cell-Free Nucleic Acid: As used herein, "cell-free nucleic acid" refers to nucleic acids not contained within or otherwise bound to a cell or, in some implementations, nucleic acids remaining in a sample following the removal of intact cells. Cell-free nucleic acids can include, for example, all non-encapsulated nucleic acids sourced from a bodily fluid (e.g., blood, plasma, serum, urine, cerebrospinal fluid (CSF), etc.) from a subject. Cell-free nucleic acids include DNA (cfDNA), RNA (cfRNA), and hybrids thereof, including genomic DNA, mitochondrial DNA, circulating DNA, siRNA, miRNA, circulating RNA (cRNA), tRNA, rRNA, small nucleolar RNA (snoRNA), Piwi-interacting RNA (piRNA), long non-coding RNA (long ncRNA), and/or fragments of any of these. Cell-free nucleic acids can be double-stranded, single-stranded, or a hybrid thereof. A cell-free nucleic acid can be released into bodily fluid through secretion or cell death processes, e.g., cellular necrosis, apoptosis, or the like. Some cell-free nucleic acids are released into bodily fluid from cancer cells, e.g., circulating tumor DNA (ctDNA). Others are released from healthy cells. CtDNA can be non-encapsulated tumor-derived fragmented DNA. A cell-free nucleic acid can have one or more epigenetic modifications, for example, a cell-free nucleic acid can be acetylated, 5-methylated, ubiquitylated, phosphorylated, sumoylated, ribosylated, and/or citrullinated.

Cellular Nucleic Acids: As used herein, "cellular nucleic acids" means nucleic acids that are disposed within one or more cells at least at the point a sample is taken or collected from a subject, even if those nucleic acids are subsequently removed as part of a given analytical process.

Communications Network: As used herein, "communications network" refers to one or more portions of a network 114, 1034 that may be an ad hoc network, an intranet, an extranet, a virtual private network (VPN), a local area network (LAN), a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, a network 114, 1034 or a portion of a network may include a wireless or cellular network and the coupling may be a Code Division Multiple Access (CDMA) connection, a Global System for Mobile communications (GSM) connection, or other type of cellular or wireless coupling. In this example, the coupling may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology.

Confidence Interval: As used herein, "confidence interval" means a range of values so defined that there is a specified probability that the value of a given parameter lies within that range of values.

Control Sample: As used herein, "control sample" or "reference sample" refers to a sample obtained from individuals without known copy number variation.

Copy Number. As used herein, can include "integer copy number" that is an integer corresponding to the copy number in a tumor cell or a non-tumor cell. Copy number can also include "observed copy number" that is a real number that represents the copy number of a mixture of tumor cells and non-tumor cells.

Copy Number Amplification: As used herein, "copy number amplification," refers to an increase in a number of repeats of a genomic region within a genome of an individual relative to a number of repeats of a genomic region within the genome of a control population.

Copy Number Deletion: As used herein, "copy number deletion," refers to a decrease in a number of repeats of a genomic region within a genome of an individual relative to a number of repeats of a genomic region within the genome of a control population.

Copy Number Variant: As used herein, "copy number variant", "CNV", or "copy number variation" refers to a phenomenon in which sections of the genome are repeated and the number of repeats in the genome varies between individuals in the population under consideration and varies between two conditions or states of an individual (e.g., CNV can vary in an individual before and after receiving a therapy).

Coverage: As used herein, "coverage" or "coverage metrics" refer to the number of nucleic acid molecules or sequencing reads that correspond to a particular genomic region of a reference sequence.

Deoxyribonucleic Acid or Ribonucleic Acid: As used herein, "deoxyribonucleic acid" or "DNA" refers to a natural or modified nucleotide which has a hydrogen group at the 2'-position of the sugar moiety. DNA can include a chain of nucleotides comprising four types of nucleotide bases: adenine (A), thymine (T), cytosine (C), and guanine (G). As used herein, "ribonucleic acid" or "RNA" refers to a natural or modified nucleotide which has a hydroxyl group at the 2'-position of the sugar moiety. RNA can include a chain of nucleotides comprising four types of nucleotides: A, uracil (U), G, and C. As used herein, the term "nucleotide" refers to a natural nucleotide or a modified nucleotide. Certain pairs of nucleotides specifically bind to one another in a complementary fashion (called complementary base pairing). In DNA, adenine (A) pairs with thymine (T) and cytosine (C) pairs with guanine (G). In RNA, adenine (A) pairs with uracil (U) and cytosine (C) pairs with guanine (G). When a first nucleic acid strand binds to a second nucleic acid strand made up of nucleotides that are complementary to those in the first strand, the two strands bind to form a double strand. As used herein, "nucleic acid sequencing data", "nucleic acid sequencing information", "sequence information", "sequence representation", "nucleic acid sequence", "nucleotide sequence", "genomic sequence", "genetic sequence", "fragment sequence", "sequencing read", or "nucleic acid sequencing read" denotes any information or data that is indicative of the order and identity of the nucleotide bases (e.g., adenine, guanine, cytosine, and thymine or uracil) in a molecule (e.g., a whole genome, whole transcriptome, exome, oligonucleotide, polynucleotide, or fragment) of a nucleic acid such as DNA or RNA. It should be understood that the present teachings contemplate sequence information obtained using all available varieties of techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, and electronic signature-based systems.

Driver Mutation: As used herein, "driver mutation" means a mutation that drives cancer progression.

Immunotherapy: As used herein, "immunotherapy" refers to treatment with one or more agents that act to stimulate the immune system so as to kill or at least to inhibit growth of cancer cells, and preferably to reduce further growth of the cancer, reduce the size of the cancer and/or eliminate the cancer. Some such agents bind to a target present on cancer cells; some bind to a target present on immune cells and not on cancer cells; some bind to a target present on both cancer cells and immune cells. Such agents include, but are not limited to, checkpoint inhibitors and/or antibodies. Checkpoint inhibitors are inhibitors of pathways of the immune system that maintain self-tolerance and modulate the duration and amplitude of physiological immune responses in peripheral tissues to minimize collateral tissue damage (see, e.g., Pardoll, Nature Reviews Cancer 12, 252-264 (2012)). Example agents include antibodies against any of PD-1, PD-2, PD-L1, PD-L2, CTLA-40, OX40, B7.1, B7He, LAG3, CD137, KIR, CCRS, CD27, or CD40. Other example agents include proinflammatory cytokines, such as IL-1β, IL-6, and TNF-α. Other example agents are T-cells activated against a tumor, such as T-cells activated by expressing a chimeric antigen targeting a tumor antigen recognized by the T-cell.

Indel: As used herein, "indel" refers to a mutation that involves the insertion or deletion of nucleotides in the genome of a subject.

Limit of Detection (LoD): As used herein, "limit of detection" means the smallest amount of a substance (e.g., a nucleic acid) in a sample that can be measured by a given assay or analytical approach.

Machine-Readable Medium: As used herein, "machine-readable medium" refers to a component, device, or other tangible media able to store instructions 1102 and data temporarily or permanently and may include, but is not limited to, random-access memory (RAM), read-only memory (ROM), buffer memory, flash memory, optical media, magnetic media, cache memory, other types of storage (e.g., erasable programmable read-only memory (EEPROM)) and/or any suitable combination thereof. The term "machine-readable medium" may be taken to include a single medium or multiple media (e.g., a centralized or distributed database, or associated caches and servers) able to store instructions 1102. The term "machine-readable medium" shall also be taken to include any medium, or combination of multiple media, that is capable of storing instructions 1102 (e.g., code) for execution by a machine 1100, such that the instructions 1102, when executed by one or more processors 1104 of the machine 1100, cause the machine 1100 to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes signals per se.

Mappability Score: As used herein, "mappability score" refers to a value that indicates an amount of homology between two regions of a reference sequence. Mappability scores for two respective regions can have increasing values as the amount of homology between the respective regions increases. In addition, mappability scores for two respective regions can have decreasing values as the amount of homology between the respective regions decreases. The amount of homology can be determined by determining an amount of misalignment between a region and the reference sequence. As the mappability score increases, the probability of a region being misaligned is reduced. Further, as the mappability score decreases, the probability of a region being misaligned increases.

Maximum MAF: As used herein, "maximum MAF" or "max MAF" refers to the maximum MAF of all somatic variants in a sample.

Minor Allele Frequency: As used herein, "minor allele frequency" refers to the frequency at which minor alleles (e.g., not the most common allele) occurs in a given population of nucleic acids, such as a sample obtained from a subject. Genetic variants at a low minor allele frequency can have a relatively low frequency of presence in a sample.

Mutant Allele Fraction: As used herein, "mutant allele fraction", "mutation dose," or "MAF" refers to the fraction of nucleic acid molecules harboring an allelic alteration or mutation at a given genomic position in a given sample. MAF is generally expressed as a fraction or a percentage. For example, an MAF can be less than about 0.5, 0.1, 0.05, or 0.01 (i.e., less than about 50%, 10%, 5%, or 1%) of all somatic variants or alleles present at a given locus.

Mutation: As used herein, "mutation" refers to a variation from a known reference sequence and includes mutations such as, for example, single nucleotide variants (SNVs), copy number variants or variations (CNVs)/aberrations, insertions or deletions (indels), gene fusions, transversions, translocations, frame shifts, duplications, repeat expansions, and epigenetic variants. A mutation can be a germline or somatic mutation. In some examples, a reference sequence for purposes of comparison is a wildtype genomic sequence of the species of the subject providing a test sample, typically the human genome.

Mutation Caller. As used herein, "mutation caller" means an algorithm (embodied in software or otherwise computer implemented) that is used to identify mutations in test sample data (e.g., sequence information obtained from a subject).

Mutation Count: As used herein, "mutation count" or "mutational count" refers to the number of somatic mutations in a whole genome or exome or targeted regions of a nucleic acid sample.

Neoplasm: As used herein, the terms "neoplasm" and "tumor" are used interchangeably. They refer to abnormal growth of cells in a subject. A neoplasm or tumor can be benign, potentially malignant, or malignant. A malignant tumor is referred to as a cancer or a cancerous tumor.

Next Generation Sequencing: As used herein, "next generation sequencing" or "NGS" refers to sequencing technologies having increased throughput as compared to traditional Sanger- and capillary electrophoresis-based approaches, for example, with the ability to generate hundreds of thousands of relatively small sequencing reads at a time. Some examples of next generation sequencing techniques include, but are not limited to, sequencing by synthesis, sequencing by ligation, and sequencing by hybridization.

Nucleic Acid Tag: As used herein, "nucleic acid tag" refers to a short nucleic acid (e.g., less than about 500 nucleotides, about 100 nucleotides, about 50 nucleotides, or about 10 nucleotides in length), used to distinguish nucleic acids from different samples (e.g., representing a sample index), or different nucleic acid molecules in the same sample (e.g., representing a molecular barcode), of different types, or which have undergone different processing. The nucleic acid tag comprises a predetermined, fixed, non-random, random or semi-random oligonucleotide sequence. Such nucleic acid tags may be used to label different nucleic acid molecules or different nucleic acid samples or sub-samples. Nucleic acid tags can be single-stranded, double-stranded, or at least partially double-stranded. Nucleic acid tags optionally have the same length or varied lengths. Nucleic acid tags can also include double-stranded molecules having one or more blunt-ends, include 5' or 3' single-stranded regions (e.g., an overhang), and/or include one or more other single-stranded regions at other locations within a given molecule. Nucleic acid tags can be attached to one end or to both ends of the other nucleic acids (e.g., sample nucleic acids to be amplified and/or sequenced). Nucleic acid tags can be decoded to reveal information such as the sample of origin, form, or processing of a given nucleic acid. For example, nucleic acid tags can also be used to enable pooling and/or parallel processing of multiple samples comprising nucleic acids bearing different molecular barcodes and/or sample indexes in which the nucleic acids are subsequently being deconvolved by detecting (e.g., reading) the nucleic acid tags. Nucleic acid tags can also be referred to as identifiers (e.g. molecular identifier, sample identifier). Additionally, or alternatively, nucleic acid tags can be used as molecular identifiers (e.g., to distinguish between different molecules or amplicons of different parent molecules in the same sample or sub-sample). This includes, for example, uniquely tagging different nucleic acid molecules in a given sample, or non-uniquely tagging such molecules. In the case of non-unique tagging applications, a limited number of tags (i.e., molecular barcodes) may be used to tag each nucleic acid molecule such that different molecules can be distinguished based on their endogenous sequence information (for example, start and/or stop positions where they map to a selected reference sequence, a sub-sequence of one or both ends of a sequence, and/or length of a sequence) in combination with at least one molecular barcode. A sufficient number of different molecular barcodes are used such that there is a low probability (e.g., less than about a 10%, less than about a 5%, less than about a 1%, or less than about a 0.1% chance) that any two molecules may have the same endogenous sequence information (e.g., start and/or stop positions, subsequences of one or both ends of a sequence, and/or lengths) and also have the same molecular barcode.

Off-Target Region: As used herein, "off-target region" refers to a genomic region of a reference sequence that is outside of target regions of the reference sequence. For example, off-target regions can include regions of the reference sequence that are outside of regions of the reference sequence that correspond to one or more probes used to capture polynucleotides of interest.

Off-Target Sequence Representation: As used herein, "off-target sequence representation" refers to polynucleotide molecules or sequencing reads that have at least a threshold amount of homology with respect to genomic regions that are outside of a target region of a reference sequence. Off-target sequence representations can refer to polynucleotide molecules and sequence reads that align with off-target regions. The threshold amount of homology can be at least about 90%, at least about 91%, at least about 92%, at least about 93%, at least about 94%, at least about 95%, at least about 96%, at least about 97%, at least about 98%, at least about 99%, at least about 99.5%, or at least about 99.9%.

On-Target Sequence Representation: As used herein, "on-target sequence representation" refers to polynucleotides or sequencing reads that have at least a threshold amount of homology with respect to target regions of a reference sequence. On-target sequence representations can refer to polynucleotide molecules and sequence reads that align with on-target regions. The threshold amount of homology can be at least about 90%, at least about 91%, at least about 92%, at least about 93%, at least about 94%, at least about 95%, at least about 96%, at least about 97%, at least about 98%, at least about 99%, at least about 99.5%, or at least about 99.9%.

Polynucleotide: As used herein, "polynucleotide", "nucleic acid", "nucleic acid molecule", "polynucleotide molecule", or "oligonucleotide" refers to a linear polymer of nucleosides (including deoxyribonucleosides, ribonucleosides, or analogs thereof) joined by internucleosidic linkages. A polynucleotide can comprise at least three nucleosides. Oligonucleotides often range in size from a few monomeric units, e.g. 3-4, to hundreds of monomeric units. Whenever a polynucleotide is represented by a sequence of letters, such as "ATGCCTG," it will be understood that the nucleotides are in 5'→3' order from left to right and that in the case of DNA, "A" denotes deoxyadenosine, "C" denotes deoxycytidine, "G" denotes deoxyguanosine, and "T" denotes deoxythymidine, unless otherwise noted. The letters A, C, G, and T may be used to refer to the bases themselves, to nucleosides, or to nucleotides comprising the bases, as is standard in the art.

Probe: As used herein, "probe" refers to a polynucleotide comprising a functionality. The functionality can be a detectable label (fluorescent), a binding moiety (biotin), or a solid support (a magnetically attractable particle or a chip). Probes can include single-stranded DNA/RNA polynucleotides or double stranded DNA polynucleotides that hybridize to target nucleic acid sequences (e.g., SureSelect® probes, Agilent Technologies). Sequence capture using probes generally depends, in part, on the number of consecutive nucleotides in at least a portion of the target nucleic acid sequence that is complementary (or nearly complementary) to the sequence of the probe. In some examples, probes can correspond to driver mutations.

Processing: As used herein, the terms "processing", "calculating", and "comparing" can be used interchangeably. In certain applications, the terms refer to determining a difference, e.g., a difference in number or sequence. For example, gene expression, copy number variation (CNV), indel, and/or single nucleotide variant (SNV) values or sequences can be processed.

Processor. As used herein, "processor" refers to any circuit or virtual circuit (a physical circuit emulated by logic executing on an actual processor) that manipulates data values according to control signals (e.g., "commands," "op codes," "machine code," etc.) and which produces corresponding output signals that are applied to operate a machine. A processor may, for example, be a CPU, a RISC processor, a CISC processor, a GPU, a DSP, an ASIC, a RFIC or any combination thereof. A processor may further be a multi-core processor having two or more independent processors (sometimes referred to as "cores") that may execute instructions contemporaneously.

Quantitative Measures: As used herein, "quantitative measures" refers to numerical values that are generated by analyzing characteristics of sequence representations. Quantitative measures can include coverage metrics and size distribution metrics. The quantitative measures can also include mutant allele frequency of germline single nucleotide polymorphisms that are related to genomic regions of a reference sequence that correspond to target regions.

Reference Sequence: As used herein, "reference sequence" refers to a known sequence used for purposes of comparison with experimentally determined sequences. For example, a known sequence can be an entire genome, a chromosome, or any segment thereof. A reference sequence can include at least about 20, at least about 50, at least about 100, at least about 200, at least about 250, at least about 300, at least about 350, at least about 400, at least about 450, at least about 500, at least about 1000, or more nucleotides. A reference sequence can align with a single contiguous sequence of a genome or chromosome or can include non-contiguous segments that align with different regions of a genome or chromosome. Example reference sequences, include, for example, human genome reference sequences, such as, hG19 and hG38.

Sample: As used herein, "sample" means anything capable of being analyzed by the methods and/or systems disclosed herein.

Sensitivity: As used herein, "sensitivity" means the probability of detecting the presence of a single nucleotide variant, an insertion, and a deletion at a given MAF and coverage and the probability of detecting the presence of a copy number variant at a given tumor fraction and coverage.

Sequencing: As used herein, "sequencing" refers to any of a number of technologies used to determine the sequence (e.g., the identity and order of monomer units) of a biomolecule, e.g., a nucleic acid such as DNA or RNA. Example sequencing methods include, but are not limited to, targeted sequencing, single molecule real-time sequencing, exon or exome sequencing, intron sequencing, electron microscopy-based sequencing, panel sequencing, transistor-mediated sequencing, direct sequencing, random shotgun sequencing, Sanger dideoxy termination sequencing, whole-genome sequencing, sequencing by hybridization, pyrosequencing, capillary electrophoresis, duplex sequencing, cycle sequencing, single-base extension sequencing, solid-phase sequencing, high-throughput sequencing, massively parallel signature sequencing, emulsion PCR, co-amplification at lower denaturation temperature-PCR (COLD-PCR), multiplex PCR, sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD™ sequencing, MS-PET sequencing, and a combination thereof. In some implementations, sequencing can be performer by a gene analyzer such as, for example, gene analyzers commercially available from Illumina, Inc., Pacific Biosciences, Inc., or Applied Biosystems/Thermo Fisher Scientific, among many others.

Single Nucleotide Polymorphism: As used herein, "single nucleotide polymorphism" or SNP means a mutation or variation in a single nucleotide that occurs at a specific portion in the genome and that is present in at least a threshold fraction of a population (e.g., 1%) having a given phenotype. A germline single nucleotide polymorphism is present in the germlines of the fraction of the population in which the germline SNP is present.

Single Nucleotide Variant: As used herein, "single nucleotide variant" or "SNV" means a mutation or variation in a single nucleotide that occurs at a specific position in the genome.

Size Distribution Metrics: As used herein, "size distribution metrics" refer to a number of sequence representations that are included in individual partitions of a size distribution based on the size of the individual sequence representations. A size of a sequence representation can refer to a number of nucleotides represented in the sequence representation. In addition, individual partitions of a size distribution can include a range of sizes of sequence representations. In various examples, the range of sizes of two adjacent partitions in the size distribution may not overlap.

Somatic Mutation: As used herein, "somatic mutation" means a mutation in the genome that occurs after conception. Somatic mutations can occur in any cell of the body except germ cells and accordingly, are not passed on to progeny.

Subject: As used herein, "subject" refers to an animal, such as a mammalian species (e.g., human) or avian (e.g., bird) species, or other organism, such as a plant. More specifically, a subject can be a vertebrate, e.g., a mammal such as a mouse, a primate, a simian or a human. Animals include farm animals (e.g., production cattle, dairy cattle, poultry, horses, pigs, and the like), sport animals, and companion animals (e.g., pets or support animals). A subject can be a healthy individual, an individual that has or is suspected of having a disease or a predisposition to the disease, or an individual that is in need of therapy or suspected of needing therapy. The terms "individual" or "patient" are intended to be interchangeable with "subject."

For example, a subject can be an individual who has been diagnosed with having a cancer, is going to receive a cancer therapy, and/or has received at least one cancer therapy. The subject can be in remission of a cancer. As another example, the subject can be an individual who is diagnosed of having an autoimmune disease. As another example, the subject can be a female individual who is pregnant or who is planning on getting pregnant, who may have been diagnosed of or suspected of having a disease, e.g., a cancer, an autoimmune disease.

Target Region: As used herein, "target region" refers to a genomic region of interest. For example, the genomic region of interest can correspond to one or more mutations that are consistent with one or more types of cancer. Additionally, the genomic region of interest can be enriched by one or more probes.

Threshold: As used herein, "threshold" refers to a predetermined value used to characterize experimentally determined values of the same parameter for different samples depending on their relation to the threshold.

Tumor Fraction: As used herein, "tumor fraction" refers to the estimate of the fraction of nucleic acid molecules derived from a tumor in a given sample. For example, the tumor fraction of a sample can be a measure derived from the max MAF of the sample or pattern of sequencing coverage of the sample or length of the cfDNA fragments in the sample or any other selected feature of the sample. In some instances, the tumor fraction of a sample is equal to the max MAF of the sample.

Variant: As used herein, a "variant" can be referred to as an allele. A variant is usually presented at a frequency of 50% (0.5) or 100% (1), depending on whether the allele is heterozygous or homozygous. For example, germline variants are inherited and usually have a frequency of 0.5 or 1. Somatic variants; however, are acquired variants and usually have a frequency of <0.5. Major and minor alleles of a genetic locus refer to nucleic acids harboring the locus in which the locus is occupied by a nucleotide of a reference sequence, and a variant nucleotide different than the reference sequence respectively. Measurements at a locus can take the form of allelic fractions (AFs), which measure the frequency with which an allele is observed in a sample.

DETAILED DESCRIPTION

Cancer is usually caused by the accumulation of mutations within genes of an individual's cells, at least some of which result in improperly regulated cell division. Such mutations can include single nucleotide variations (SNVs), gene fusions, insertions, transversions, translocations, and inversions. These mutations can also include copy number variations that correspond to an increase or a decrease in the number of copies of a gene within a tumor genome relative to an individual's noncancerous cells. An extent of mutations present in cell-free nucleic acids and an amount of mutated cell-free nucleic acids of a sample can be used as biomarkers to determine tumor progression, predict patient outcome, and refine treatment choices. In various examples, the extent of mutations present in cell-free nucleic acids can be indicated by tumor cells copy number and tumor fraction for a given sample.

In existing systems and methods, polynucleotides derived from cell-free nucleic acids included in a sample can be identified that correspond to target regions of a reference sequence. One or more quantitative measures that correspond to amounts of the on-target sequences derived from a sample can be generated and used to determine estimates for the copy number of tumor cells and/or tumor fraction for a given sample. Additionally, in existing systems, polynucleotides derived from a sample can be identified that are aligned with portions of the reference sequence that are outside of the target regions. In existing systems, the off-target sequence representations are typically not used to determine estimates for at least one of the copy number of tumor cells or the tumor fraction of a sample because the off-target sequences do not correspond to the on-target regions of the reference sequence.

In implementations described herein, information derived from a sample that goes beyond information derived from on-target sequence representations can be used to determine tumor metrics with respect to a subject providing the sample. For example, information derived from off-target sequence representations can be used to determine estimates for the copy number of tumor cells and/or the tumor fraction of a sample. Additionally, information derived from the presence of germline SNPs can be used to determine estimates for at least one of the copy number of tumor cells or the tumor fraction of a sample. The use of information in addition to the information derived from on-target sequence representations to determine estimates for at least one of the copy number of tumor cells or the tumor fraction of a sample can improve the accuracy of the estimates of the copy number of tumor cells and/or the tumor fraction of a sample in relation to existing techniques. Further, the improvement in the accuracy of the estimates of the copy number of the tumor cells and/or the tumor fraction of the sample is a result of using information corresponding to off-target molecules that was previously not considered in detecting the copy number variation in a subject and was therefore discarded.

In one or more illustrative examples, a number of off-target sequence representations can be determined from sequencing data that is derived from a sample. In addition, a first segmentation process can be performed that determines a number of first segments for a reference sequence. The number of first segments can be referred to as “bins”, in one or more examples. Quantitative measures can be determined with respect to the off-target sequence representations. For example, coverage metrics indicating a number of sequence representations can be determined with respect to off-target sequence representations related to individual first segments. The coverage metrics can be normalized with respect to reference coverage metrics determined from samples of individuals in which copy number variation is not present. In various examples, a second segmentation process can be performed such that each second segment includes multiple first segments. The normalized coverage metrics for the first segments that correspond to individual second segments can be used to determine tumor cells copy number for one or more second segments and to determine tumor fraction for the sample. The tumor cells copy number for one or more second segments and the tumor fraction can be used as values of parameters for a maximum likelihood estimation model that determines a likelihood of the values of the tumor cells copy number and/or the tumor fraction. In some implementations, size distribution data indicating the distribution of different sized sequence representations with respect to segments of the reference sequence can also be used to determine values of parameters of a maximum likelihood estimation model, such as the tumor fraction and tumor cells copy number. Further, single nucleotide polymorphism data can be used to determine values of parameters of a maximum likelihood estimation model.

FIG. 1 is a diagrammatic representation of an example architecture 100 that determines tumor metrics, such as copy number variation, in a subject based on the information obtained from off-target regions, according to one or more implementations. In one or more examples, the disease under consideration is a type of cancer. Non-limiting examples of such cancers include biliary tract cancer, bladder cancer, transitional cell carcinoma, urothelial carcinoma, brain cancer, gliomas, astrocytomas, breast carcinoma, metaplastic carcinoma, cervical cancer, cervical squamous cell carcinoma, rectal cancer, colorectal carcinoma, colon cancer, hereditary nonpolyposis colorectal cancer, colorectal adenocarcinomas, gastrointestinal stromal tumors (GISTs), endometrial carcinoma, endometrial stromal sarcomas, esophageal cancer, esophageal squamous cell carcinoma, esophageal adenocarcinoma, ocular melanoma, uveal melanoma, gallbladder carcinomas, gallbladder adenocarcinoma, renal cell carcinoma, clear cell renal cell carcinoma, transitional cell carcinoma, urothelial carcinomas, Wilms tumor, leukemia, acute lymphocytic leukemia (ALL), acute myeloid leukemia (AML), chronic lymphocytic (CLL), chronic myeloid (CML), chronic myelomonocytic (CMML), liver cancer, liver carcinoma, hepatoma, hepatocellular carcinoma, cholangiocarcinoma, hepatoblastoma, Lung cancer, non-small cell lung cancer (NSCLC), mesothelioma, B-cell lymphomas, non-Hodgkin lymphoma, diffuse large B-cell lymphoma, Mantle cell lymphoma, T cell lymphomas, non-Hodgkin lymphoma, precursor T-lymphoblastic lymphoma/leukemia, peripheral T cell lymphomas, multiple myeloma, nasopharyngeal carcinoma (NPC), neuroblastoma, oropharyngeal cancer, oral cavity squamous cell carcinomas, osteosarcoma, ovarian carcinoma, pancreatic cancer, pancreatic ductal adenocarcinoma, pseudopapillary neoplasms, acinar cell carcinomas. Prostate cancer, prostate adenocarcinoma, skin cancer, melanoma, malignant melanoma, cutaneous melanoma, small intestine carcinomas, stomach cancer, gastric carcinoma, gastrointestinal stromal tumor (GIST), uterine cancer, or uterine sarcoma.

The architecture 100 can include a sequencing machine 102. In one or more examples, the sequencing machine 102 can be any of a number of sequencing machines that can perform one or more sequencing operations that amplify nucleic acids present in a sample 104. In various examples, the sequencing machine 102 can perform next-generation sequencing operations. In one or more examples, the sample 104 can include an amount of at least one bodily fluid extracted from a subject. In one or more additional examples, the sample 104 can include a tissue sample that is obtained from a subject.

Prior to sequencing, polynucleotides can be extracted from the sample 104. The extraction of polynucleotides from the sample 104 can include implementing one or more cell lysis techniques to cleave the membranes of cells included in the sample 104 and applying one or more proteases to break down proteins included in the sample 104. The extraction of polynucleotides from the sample 104 can also include a number of washing and/or elution techniques to separate the polynucleotides from other components included in the sample 104. In various examples, thousands, up to millions, up to billions of polynucleotides can be extracted from the sample 104 prior to sequencing. In addition, blunt-end ligation can be performed on the extracted polynucleotides and adapters, as well as tags (e.g., molecular barcodes) can be added to the extracted polynucleotides. The extracted polynucleotides can also be enriched by causing hybridization between the extracted polynucleotides and probes that correspond to target regions of a reference sequence. The enrichment process can identify thousands, hundreds of thousands, up to millions of polynucleotides that correspond to on-target regions associated with the probes. Thousands, up to millions of unenriched polynucleotides that correspond to off-target regions of the reference sequence can also be present after the enrichment process.

Subsequent to the enrichment process, the enriched polynucleotides can be amplified according to one or more amplification processes. The one or more amplification processes can produce thousands, up to millions of copies of individual enriched polynucleotides. In one or more examples, a portion of the unenriched polynucleotides can be amplified, in some instances, but not to the extent that the enriched polynucleotides are amplified. The one or more amplification processes can generate an amplification product that undergoes one or more sequencing operations. After performing one or more sequencing operations with respect to the sample 104, the sequencing machine 102 can produce a sequencing data 106.

The sequencing data 106 can include alphanumeric representations of the nucleic acids included in an amplification product. For example, the sequencing data 106 can include, for individual nucleic acids of the amplification product, data that corresponds to a string of letters that represent the respective chains of nucleotides that correspond to the individual nucleic acids.

The sequencing data 106 can be stored in one or more data files. For example, the sequencing data 106 can be stored in a FASTQ file that comprises a text-based sequencing data file format storing raw sequence data and quality scores. In one or more additional examples, the sequencing data 106 can be stored in a data file according to a binary base call (BCL) sequence file format. In one or more further examples, the sequencing data 106 can be stored in a BAM file. In one or more examples, the sequencing data 106 can comprise at least about one gigabyte (GB), at least about 2 GB, at least about 3 GB, at least about 4 GB, at least about 5 GB, at least about 8 GB, or at least about 10 GB. An individual sequence representation included in the sequencing data 106 can be referred to herein as a "read" or a "sequencing read." In various examples, individual first nucleic acids included in the sample 104 can correspond to multiple sequence representations included in the sequencing data 106 as a result of the amplification of the individual first nucleic acids. In one or more additional examples, individual second nucleic acids included in the sample 104 can correspond to a single sequence representation included in the sequencing data 106 as a result of the absence of amplification of the individual second nucleic acids.

The architecture 100 can include a computing system 108 that obtains the sequencing data 106 from the sequencing machine 102 and analyzes the sequencing data 106. For example, the computing system 108 can analyze the sequencing data 106 to determine a probability that copy number variation is present within a subject from which the sample 104 is derived. In one or more additional examples, the computing system 108 can also determine a probability that a tumor is present in a subject that provided the sample 104. The computing system 108 can include one or more computing devices 110. The one or more computing devices 110 can include at least one of one or more desktop computing devices, one or more mobile computing devices, or one or more server computing device. In various examples, at least a portion of the one or more computing devices 110 can be included in a remote computing environment, such as a cloud computing environment. In one or more examples, the computing system 108 and the sequencing machine 102 can be owned, operated, maintained, and/or controlled by a single organization. In one or more additional examples, the computing system 108 and the sequencing machine 102 can be owned, operated, maintained, and/or controlled by multiple organizations.

At operation 112, the computing system 108 can perform an alignment process. The alignment process can include determining that at least a portion of individual sequence representations included in the sequencing data 106 correspond to a genomic region of a reference sequence. The alignment process can determine an amount of homology between individual sequence representations included in the sequence data 106 and portions of the reference sequence. The amount of homology between a given sequence representation and the reference sequence can indicate a number of positions of the reference sequence that have the same nucleotide as corresponding positions of the given sequence representation. The computing system 108 can determine that a sequence representation is aligned with a portion of a reference sequence based on determining that the sequence representation and the portion of the reference sequence have at least a threshold amount of homology. In scenarios where a sequence representation has at least the threshold amount of homology with respect to multiple portions of the reference sequence, the portion of the reference sequence having the greatest amount of homology with the sequence representation can be determined to be aligned with the sequence representation. Sequence representations having at least the threshold amount of homology with the reference sequence can be included in aligned sequence representations 114 that are generated by the alignment process that takes place at operation 112.

The amount of homology between a given sequence representation and a portion of a reference sequence can be determined using BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Genetics Computer Group, University Research Park, Madison Wis.), using default settings, which uses the algorithm of Needleman and Wunsch (J. Mol. Biol. 48; 443-453 (1970)). The amount of homology between a sequence representation and a portion of the reference sequence can also be determined using a Burrows-Wheeler aligner (Li, H., & Durbin, R. (2009). Fast and accurate short read alignment with Burrows-Wheeler transform. *Bioinformatics,* 25(14), 1754-1760).

In one or more implementations, individual aligned sequence representations 114 can correspond to individual reads that are included in the sequencing data 106. In these scenarios, the aligned sequence representations 114 can include multiple reads that correspond to a single polynucleotide included in the sample 104. reference sequence. In one or more additional examples, the aligned sequence representations 114 can correspond to individual nucleic acids included in the sample 104. In these situations, the computing system can determine a group of reads included in the sequence data 106 that correspond to an individual nucleic acid included in the sample 104 based on molecular bar codes that are common to each group of sequencing reads. That is, individual nucleic acids included in the sample 104 can be encoded with a molecular bar codes that uniquely identify the individual nucleic acids and, in at least some cases, the individual nucleic acids can be represented by multiple reads included in the sequencing data 106. Accordingly, when multiple sequence representations are present in the sequencing data 106 that correspond to a single nucleic acid included in the sample 104, the computing system 108 can group the multiple sequence representations together. In various examples, the groups of sequence representations that correspond to a single nucleic acid included in the sample 104 can be referred to herein as "families." Additionally, start and stop positions with respect to the reference sequence of the aligned sequence representations 114 having a common molecular barcode can be used to group the sequence representations that correspond to individual nucleic acids included in the sample 104. In one or more illustrative examples, an individual sequence representation that represents a family of sequence representations that corresponds to a single nucleic acid included in the sample 104 can be referred to herein as a "consensus sequence representation."

The computing system 108 can analyze the aligned sequence representations 114 at operation 116. In one or more examples, the aligned sequence representations 114 can be analyzed with respect to a number of target regions of the reference sequence. In one or more illustrative examples, the target regions can correspond to polynucleotide sequences of the probes used to identify nucleic acids of interest that are present within the sample 104. The computing system 108 can analyze the aligned sequence representations 114 to determine at least a subset of the sequence representations that can be used to determine whether copy number variation is present in the subject from which the sample 104 was obtained. In one or more examples, the aligned sequence representations 114 can be analyzed to determine on-target sequence representations 118 that are included in the aligned sequence representations 114. On-target sequence representations 118 can include sequence representations included in the aligned sequence representations 114 that have at least a threshold amount of homology with target regions of the reference sequence.

In addition, the aligned sequence representations 114 can be analyzed to determine off-target sequence representations 120. The off-target sequence representations 120 can be aligned with portions of the reference sequence that do not correspond to target regions. In one or more examples, the off-target sequence representations 120 can have no overlap with at least one target region of the reference sequence. In one or more additional examples, the off-target sequence representations 120 can have less than a threshold amount of overlap with at least one target region of the reference sequence. In one or more illustrative examples, the threshold amount of overlap can be no greater than about 10% homology between a sequence representation and a target region, no greater than about 9% homology between a sequence representation and a target region, no greater than about 8% homology between a sequence representation and a target region, no greater than about 7% homology between a sequence representation and a target region, no greater than about 6% homology between a sequence representation and a target region, no greater than about 5% homology between a sequence representation and a target region, no greater than about 4% homology between a sequence representation and a target region, no greater than about 3% homology between a sequence representation and a target region, no greater than about 2% homology between a sequence representation and a target region, no greater than about 1% homology between a sequence representation and a target region, no greater than about 0.5% homology between a sequence representation and a target region, or no greater than about 0.1% homology between a sequence representation and a target region.

The computing system 108 can, at operation 122, analyze one or more quantitative measures derived from the sequencing data 106. At least a portion of the quantitative measures derived from the sequencing data 106 can be determined with respect to the on-target sequence representations 118. In addition, at least a portion of the quantitative measures derived from the sequencing data 106 can be determined with respect to the off-target sequence representations 120. In one or more examples, the computing system 108 can determine one or more coverage metrics with respect to the on-target sequence representations 118. For example, the computing system 108 can determine a number of the on-target sequence representations that are aligned with individual target regions of the reference sequence to generate respective coverage metrics for individual target regions. In various examples, the computing system 108 can determine one or more normalized coverage metrics for individual target regions based on the respective number of on-target sequence representations 118 that correspond to the individual target regions in relation to the total number of on-target sequence representations 118 or with respect to the number of on-target sequence representations 118 that correspond to a group of target regions.

Additionally, the computing system 108 can determine one or more coverage metrics with respect to the off-target sequence representations 120. In one or more examples, the computing system 108 can determine a plurality of segments of the reference sequence and determine a number of the off-target sequence representations 120 that correspond to individual segments of the plurality of segments. In one or more additional examples, the computing system 108 can determine one or more size distribution metrics with respect to the off-target sequence representations 120. For example, the computing system 108 can determine respective size distributions that correspond to individual segments of the plurality of segments based on a number of the off-target sequence representations 120 having a particular size or range of sizes. In one or more illustrative examples, the number of nucleotides included in an individual off-target sequence representation 120 can be referred to herein as a "size" of the individual off-target sequence representation 120. In one or more examples, the size of an individual sequence representation can include a number of nucleotides that is included in the molecule that corresponds to the individual sequence representation. In one or more additional examples, the size of an individual sequence representation can include a number of nucleotides that is included in the molecule that corresponds to the individual sequence representation in addition to one or more additional nucleotides, such as nucleotides of an adapter and/or barcode. Further, a size distribution can include a normal distribution of sizes of sequence representations based on a mean sequence representation size and having at least eight partitions. The partitions can be distributed equally above the mean and below the mean. In various examples, the individual partitions can correspond to one or more standard deviations from the mean.

In one or more examples, the computing system 108 can perform multiple segmentation processes with respect to the reference sequence. For example, the computing system 108 can perform a first segmentation process that partitions the reference sequence into a plurality of first segments. In one or more implementations, the plurality of first segments can be referred to as "bins." The computing system 108 can also perform a second segmentation process that partitions the reference sequence into a plurality of second segments. In various examples, the plurality of first segments can include a greater number of segments than the plurality of second segments. To illustrate, the plurality of second segments can include multiple first segments. In one or more examples, the computing system 108 can determine quantitative measures, such as at least one of coverage metrics or size distribution metrics, for both the plurality of first segments and the plurality of second segments. To illustrate, the quantitative measures determined by the computing system 108 with respect to the plurality of first segments can be used by the computing system 108 to determine the quantitative measures for the plurality of second segments.

In one or more illustrative scenarios, multiple segmentations processes can be implemented because copy number variations are not present within the smaller, first segments. Accordingly, a second segmentation process that generates second segments that include multiple first segments is implemented, such that the second segments have a size that corresponds to a genomic region in which copy number variation may take place. Additionally, the first segmentation process can be performed to generate normalized data for individual first segments that can minimizes biases that may be present. Thus, performing multiple segmentation processes can generate quantitative measures that can be used to more accurately determine copy number variation and/or tumor fraction with respect to a subject that provided the sample 104.

The analysis of the quantitative measures derived from the on-target sequence representations 118 and the off-target sequence representations 120 performed by the computing system 108 at operation 122 can be used to determine one or more tumor metrics 124. In one or more examples, the one or more tumor metrics 124 can include tumor cells copy number for individual second segments. The tumor cells copy number for individual second segments can indicate an amount of amplification or deletion in a genomic region that corresponds to one or more of the individual second segments. In various examples, the tumor cells copy number can indicate a loss of heterozygosity of a genomic region that corresponds to one or more of the individual second segments. In one or more additional examples, the one or more tumor metrics 124 can include an estimate of the tumor fraction that corresponds to the sample 104. In one or more illustrative examples, the one or more tumor metrics 124 can indicate progression or regression of growth of a tumor within an individual from which the sample 104 was obtained. Additionally, the one or more tumor metrics 124 can indicate effectiveness of one or more treatments provided to a subject that provided the sample 104. In one or more additional illustrative examples, the one or more tumor metrics 124 can be utilized with respect to a model to generate a probability that a tumor is present in the subject from which the sample 104 was obtained. In one or more further illustrative examples, the one or more tumor indicators 124 can correspond to parameters of a maximum likelihood estimation model that can be implemented to determine a tumor cells copy number for a subject from which the sample 104 was obtained. In various other illustrative examples, the one or more tumor indicators 124 can correspond to parameters of an expectation maximization model that can be implemented to determine a tumor cells copy number of a subject from which the sample 104 was obtained.

Figure 2:
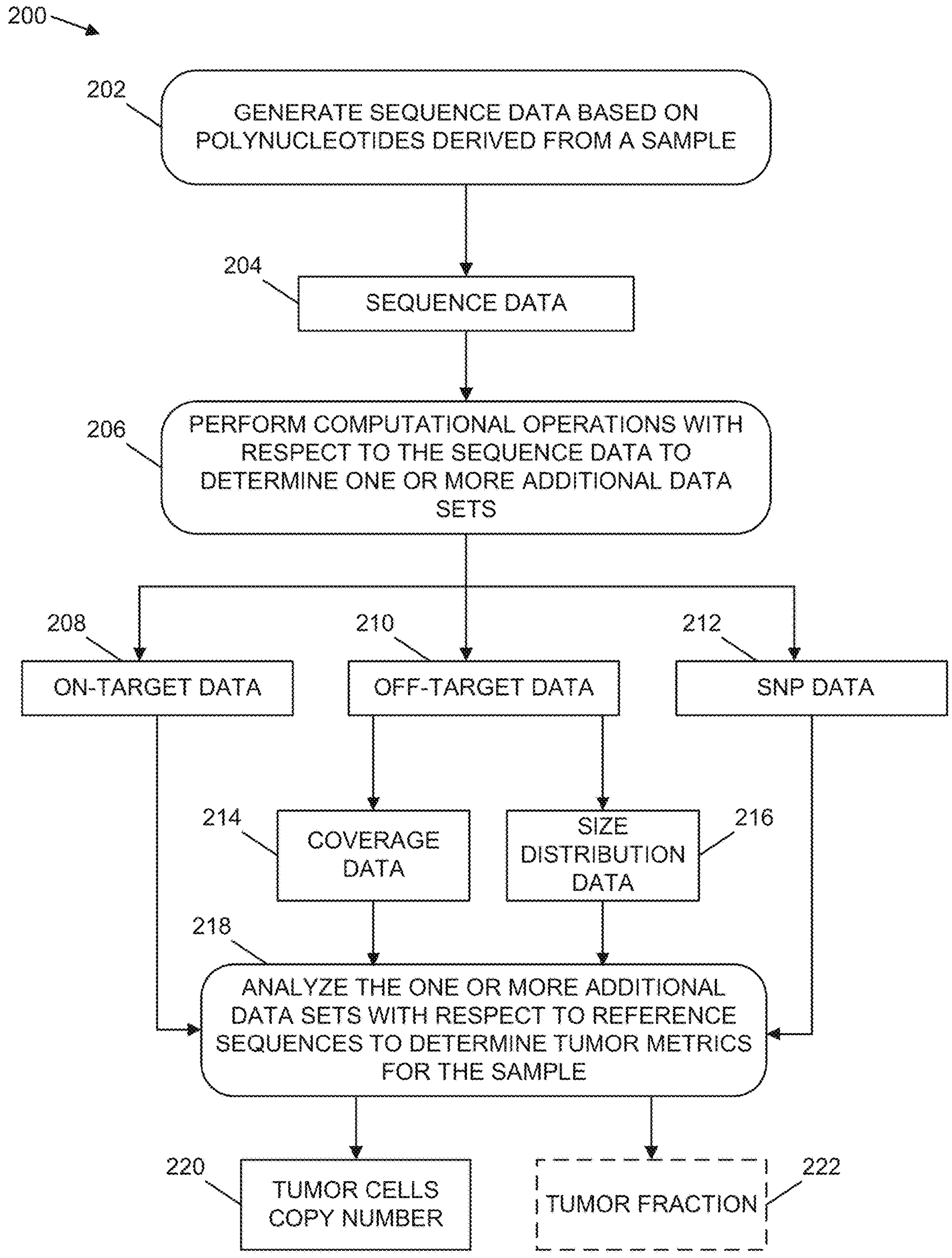
FIG. 2 is a flowchart of an example process to determine tumor metrics related to a subject based on on-target polynucleotides, off-target polynucleotides, and single nucleotide polymorphism data, according to one or more implementations.

FIG. 2 is a flowchart of an example process 200 to determine tumor metrics related to a subject, such as tumor cells copy number, based on on-target sequence representations, off-target sequence representations, and single nucleotide polymorphism data, according to one or more implementations. The process 200 can include, at 202, generating sequencing data 204 based on polynucleotides derived from a sample. The sequencing data 204 can include sequencing reads corresponding to data generated by a sequencing machine. In one or more examples, the sequencing data 204 can indicate that a number of sequencing reads are derived from a single polynucleotide.

At operation 206, the process 200 can include performing computational operations with respect to the sequencing data 204 to determine one or more additional data sets. In various examples, the one or more additional data sets can include one or more subsets of the sequence representations included in the sequencing data 204. The one or more additional data sets can be determined based one or more criteria. For example, operation 206 can be performed to produce on-target data 208 based on determining a first subset of the sequence representations included in the sequencing data 204 that correspond to target regions of a reference sequence. Additionally, operation 206 can be performed to produce off-target data 210 based on determining a second subset of the sequence representations included in the sequencing data 204 that correspond to portions of the reference sequence that exclude the target regions.

Further, operation 206 can be performed to produce single nucleotide polymorphism data 212 based on identifying sequence representations included in the sequencing data 204 that correspond to a number of germline SNPs. In various examples, the germline SNPs used to produce the SNP data 212 can include germline SNPs that are included in genomic regions of a reference sequence that correspond to target regions. In one or more examples, the SNP data 212 can be determined by analyzing sequence representations of the sequence data 204 in relation to the positions and variations that corresponds to respective germline SNPs that correspond to one or more probes. In one or more implementations, the SNP data 212 can include sequence representations of a number of individual germline SNPs included in one or more publicly available databases. In one or more illustrative examples, the SNP data 212 can include sequence representations of germline SNPs identified in a version of the gnomAD database, such as a most recent version of the gnomAD database at the time of filing this document. In one or more additional examples, a number of sequence representations can be grouped into families according to molecular barcodes common to the number of sequence representations and based on start positions and stop positions with respect to the original polynucleotide molecule that corresponds to a subset of the number of sequence representations included in individual families. Quantitative measures that correspond to the SNPs derived from the sample can be determined based on the number of families that align to respective portions of the reference genome related to individual SNPs.

Computational operations performed with respect to operation 206 can also utilize the off-target data 210 to determine quantitative measures based on the sequence representations included in the off-target data 210. For example, computational operations can be performed to determine coverage data 214 and size distribution data 216. The coverage data 214 can include a number of sequence representations that correspond to individual segments of the reference sequence. In one or more examples, the coverage data 214 can indicate a number or count of sequence representations that correspond to individual segments of off-target regions of a reference sequence. In one or more additional examples, the coverage data 214 can indicate a number of polynucleotides that correspond to individual segments of off-target regions of a reference sequence.

Normalized quantitative measures can also be determined in relation to the off-target data 210. For example, the coverage data 214 can also include normalized coverage data. In one or more illustrative examples, normalized coverage data can indicate a first coverage metric obtained from a given segment of the reference sequence in relation to a second coverage metric obtained from the given segment. In one or more illustrative examples, the second coverage metric is determined from samples of individuals in which a copy number variation is not detected. In various examples, the second coverage metric can be a reference coverage metric. reference sequence. In one or more examples, an average of the number of sequence representations that correspond to the reference coverage metric for a given segment of the reference sequence can be determined and used to determine the normalized coverage metric.

Additionally, the size distribution data 216 can indicate a distribution of sizes with respect to sequence representations that correspond to a given segment of the reference sequence. In various examples, sizes of sequence representations can be grouped to form a number of partitions that each include a range of sizes of sequence representations. The distribution of sizes of sequence representations can indicate a number of sequence representations that correspond to each respective partition.

In one or more examples, the size distribution data 216 can include normalized size distribution data. The normalized size distribution data can indicate a first distribution of sizes of first sequence representations that correspond to the sample with respect to a given segment of the reference sequence in relation to a second distribution of sizes of second sequence representations that correspond to the given segment that are obtained from samples of individuals in which copy number variation is not detected. reference sequence. In one or more illustrative examples, the second sequence representations can be used to determine reference size distribution metrics. In these scenarios, the normalized size distribution data can include a ratio of the first distribution of sizes of the first sequence representations with respect to the second distribution of sizes of the second sequence representations.

At 218, the process 200 can include analyzing the one or more additional data sets with respect to reference sequences to determine indicators of copy number variation being present in a subject. In the illustrative example of FIG. 2, at least one of the on-target data 208, the off-target data 210, or the SNP data 212 can be used to determine tumor cell copy number 220 with respect to a sample from which the sequencing data 204 is derived. In addition, at least one of the on-target data 208, the off-target data 210, or the SNP data 212 can be used to determine tumor fraction 222 in relation to the sample used to derive the sequencing data 204.

The tumor cells copy number 220 and, in at least some instances, the tumor fraction 222 for the sample can be determined by:

observed coverage=$2*(1-\mathrm{TF})+n*\mathrm{TF}$, where $n$ is the tumor cell copy number 220 and TF is the sample tumor fraction 222.

In one or more illustrative examples, the tumor fraction 220 of a given sample can be at least about 0.05%, at least about 0.1%, at least about 0.2%, at least about 0.5%, at least about 1%, at least about 2%, at least about 3%, at least about 4%, at least about 5%, at least about 10%, at least about 15%, at least about 20%, at least about 25%, at least about 30%, at least about 35%, at least about 40%, at least about 45%, or at least about 50% of all nucleic acids included in the given sample.

The observed coverage and the tumor cell copy number 220 used to determine the tumor fraction 222 can be determined by performing one or more segmentation operations with respect to the reference sequence to determine a number of segments of the reference sequence. In one or more examples, results of segmentations operations performed in relation to the different types of data can be different. For example, coverage data 214 can be used to determine a first segmentation of a reference sequence. Additionally, the on-target data 210 and the coverage data 214 can be used determine merged data that can be used to determine a second segmentation of the reference sequence that is different from the first segmentation.

In various examples, the on-target data 208 can include a number of on-target sequence representations and the observed coverage for the on-target data 208 can be determined for individual target regions of the reference sequence by determining a respective number of the on-target sequence representations that correspond to the individual target regions of the reference sequence. In one or more illustrative examples, a number of on-target sequence representations that are homologous with respect to a middle region of a target region can be determined to determine the observed coverage with respect to the on-target region. The middle region of the target region can include at least one nucleotide, at least two nucleotides, at least three nucleotides, at least four nucleotides, at least 5 nucleotides, at least 10 nucleotides, at least 15 nucleotides, at least 20 nucleotides, or at least 25 nucleotides. In one or more additional examples, the coverage data for the on-target data 208 can correspond to an average coverage of the target sequence representations across segments of a reference genome, such as 100 kb segments.

In one or more further examples, the on-target data 208 can include size distribution data that corresponds to individual segments of the reference sequence. In one or more examples, a size distribution can include a number of gradations that each include a range of sizes of on-target sequence representations. The size distribution for an individual segment of the reference sequence can include a number of the on-target sequence representations included in each gradation of the distribution.

In addition, the on-target data 208 related to coverage data and/or size distribution data can be normalized. In various examples, the on-target data 208 can be normalized in relation to at least one of reference coverage data or reference size distribution data based on on-target sequence representations that are generated based on a number of samples obtained from individuals in which a tumor is not present. The on-target data 208 with respect to on-target coverage data can also be normalized in relation to a median value for coverage of on-target sequence representations.

Tumor cells copy number 220 can be determined with respect to on-target data 208 according to techniques described in PCT Application Publication No. WO2017/106768 and entitled "Methods to Determine Tumor Gene Copy Number by Analysis of Cell-Free DNA," which is incorporated by reference herein in its entirety. The observed coverage and tumor cells copy number 220 generated using the on-target data 208 can be used to determine an estimate of the tumor fraction 222, in at least some implementations. The off-target data 210 can include a number of off-target sequence representations and the observed coverage for the coverage data 214 derived from the off-target data 210 can be determined for individual segments of the reference sequence by determining a number of the off-target sequence representations that correspond to individual segments of the reference sequence. The tumor cell copy number 220 can be determined for individual segments of the reference sequence. In one or more illustrative examples, a segmentation process can be performed with respect to the reference sequence using the coverage data 214 such that the segments are generated by determining regions of the reference sequence where the copy number for a given segment is not changing after one or more iterations of the segmentation process. In this way, the tumor cells copy number 220 for each segment is determined based on the results of a segmentation process performed using at least the coverage data 214. The observed coverage and tumor cell copy number 220 generated using the coverage data 214 can be used to determine an estimate of the tumor fraction 222.

Additionally, the observed coverage for the size distribution data 216 can correspond to size distributions derived from the off-target data 210 that correspond to individual segments of the reference sequence. In one or more examples, a size distribution can include a number of gradations that each include a range of sizes of sequence representations. The size distribution for an individual segment of the reference sequence can include a number of the off-target sequence representations included in each gradation of the distribution. The tumor cells copy number 220 can be determined for individual segments of the reference sequence based on size distribution metrics for individual segments of the reference sequence. In one or more illustrative examples, a segmentation process can be performed with respect to the reference sequence using the size distribution data 216 such that the segments are generated by determining regions of the reference sequence where the tumor cells copy number 220 for the region is not changing after a number of iterations of the segmentation process. In this way, the tumor cells copy number 220 for each segment is determined based on the results of a segmentation process performed using at least the size distribution data 216. The observed coverage and tumor cells copy number 220 generated using the size distribution data 216 can be used to determine an estimate of the tumor fraction 220.

In one or more further examples, a merged version of the coverage data 214 of the off-target sequence representations and coverage data for the on-target sequence representations can be used to determine the tumor-cells copy number 220 and/or the tumor fraction 222. In one or more examples, the merged coverage data can be determined based on a number of on-target sequence representations and a number of off-target sequence representations that correspond to individual regions of a reference genome. In various examples, the merged coverage data can be determined based on normalized coverage data generated with respect to the on-target data 208 and the off-target data 210. In one or more illustrative examples, the merged coverage data can be determined by shifting the on-target coverage data based on the on-target regions and the off-target regions within proximity to a given gene such that the on-target and off-target coverage data are distributed with respect to a common mean. In one or more implementations, the distributions of the coverage data for the on-target regions and the off-target regions can be different.

The SNP data 212 can be used to determine the tumor fraction 222 by determining a mutant allele frequency (MAF) for individual SNPs that are present in the sequencing data 204. Tumor cells copy number 220 for segments of the reference sequence can be determined using the SNP data 212 and techniques such as those described by Chen, Gary et al., "Precise inference of copy number alternations in tumor samples from SNP arrays", Bioinformatics 2013 Dec. 1; 29(23): 2964-2970.

After the tumor cells copy number 220 and the tumor fraction 222 are determined using at least one of the on-target data 208, the off-target data 210, or the SNP data 212, a model can be implemented using values of the tumor cells copy number 220 and values of the tumor fraction 222 as parameters of the model. In one or more implementations, values for the tumor cells copy number 220 and values of the tumor fraction 222 determined based on each of the on-target data 208, the off-target data 210, and the SNP data 212 can be combined and a model can be implemented using the combined values to determine a likelihood of the estimates of the tumor cells copy number 220 and the tumor fraction 222.

Figure 3:
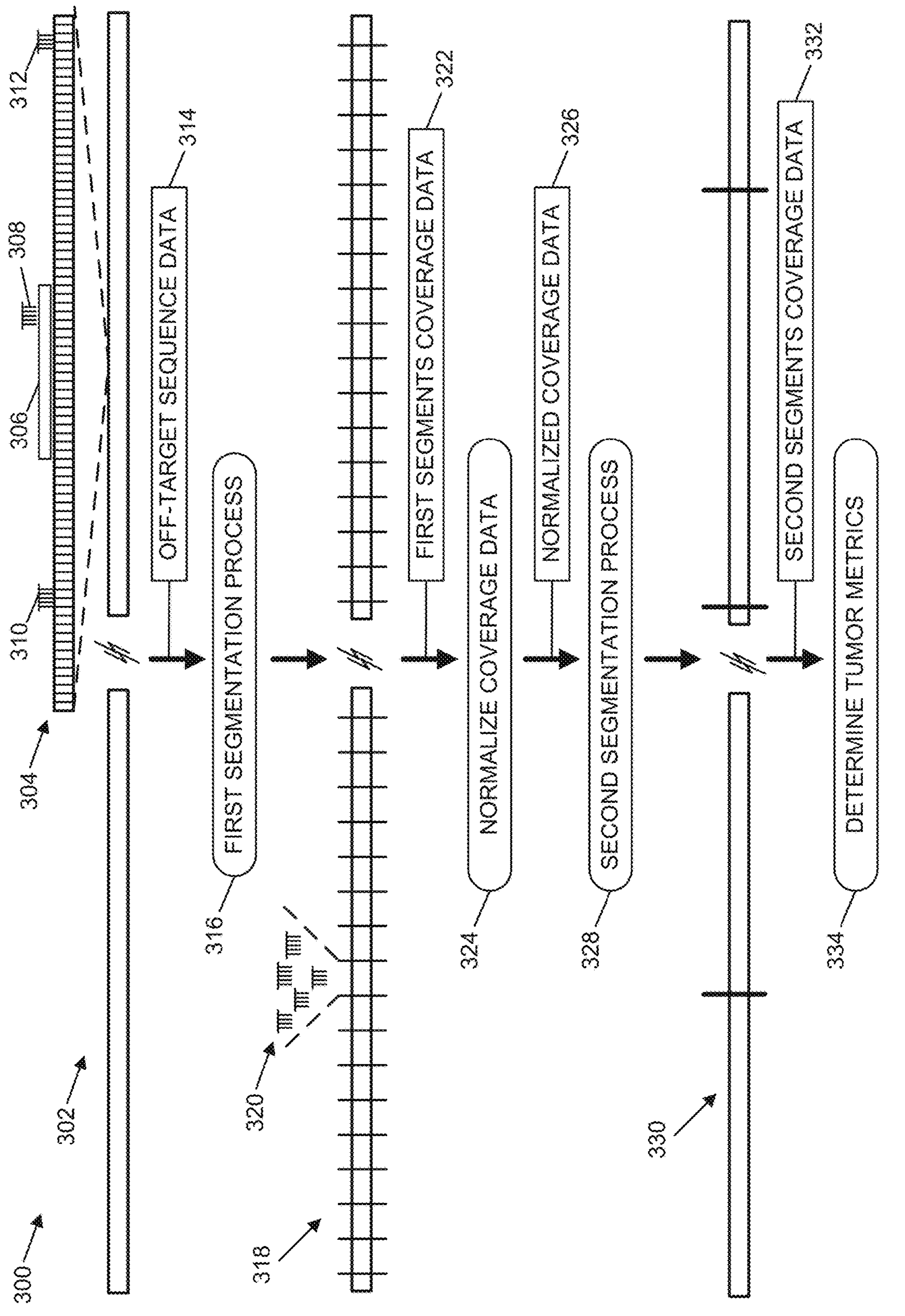
FIG. 3 is a diagrammatic representation of an example process to determine tumor metrics related to a subject based on coverage metrics derived from off-target polynucleotides, according to one or more implementations.

FIG. 3 is a diagrammatic representation of an example process 300 to determine tumor metrics related to a subject based on coverage metrics derived from off-target sequences, according to one or more implementations. The process 300 can include determining on-target sequence representations and off-target sequence representations based on sequencing data that includes sequence representations derived from a sample obtained from a subject. In one or more examples, on-target sequence representations and off-target sequence representations can be determined by analyzing sequence representations with respect to a reference sequence 302. To illustrate, sequence representations can be analyzed with respect to one or more portions of the reference sequence 302, such as an illustrative reference sequence portion 304, to determine an amount of homology between the sequence representations and the illustrative reference sequence portion 304. In the illustrative example of FIG. 3, the illustrative reference sequence portion 304 can include a target region 306. In various examples, the target region 306 can correspond to a region of the reference sequence 302 that corresponds to a driver mutation. In various examples, the reference sequence 302 can have at least about 500 target regions, at least about 1000 target regions, at least about 2500 target regions, at least about 5000 target regions, at least about 10,000 target regions, at least about 15,000 target regions, at least about 20,000 target regions, at least about 25,000 target regions, or at least about 30,000 target regions. The target region 306 can include from about 25 nucleotides to about 250 nucleotides, from about 50 nucleotides to about 200 nucleotides, or from about 75 nucleotides to about 150 nucleotides.

Additionally, in the illustrative example of FIG. 3, a first sequence representation 308, a second sequence representation 310, and a third sequence representation 312 are analyzed with respect to the illustrative reference sequence portion 304. Based on the analysis, the first sequence representation 308 can be determined to be aligned the target region 306. In these scenarios, the first sequence representation 308 can be identified as an on-target sequence. Further, the second sequence representation 310 can be determined to be aligned with a portion of the illustrative reference sequence portion 304 that is outside of the target region 306. The third sequence representation 312 can also be determined to be aligned with an additional portion of the illustrative reference sequence portion 304 that is outside of the target region 306. In these situations, the second sequence representation 310 and the third sequence representation 312 can be identified as off-target sequences.

The alignment process between sequence representations derived from a sample and the reference sequence 302 can generate off-target sequence data 314. The off-target sequence data 314 can include sequence representations that are aligned with regions of the reference sequence 302 that are outside of target regions. For example, the off-target sequence data 314 can include the second sequence representation 310 and the third sequence representation 312.

The process 300 can include, at operation 316, a first segmentation process that is performed based on the off-target sequence data 314. In one or more examples, sequence data that corresponds to on-target sequence representations is excluded from being used during the first segmentation process 316. In various examples, the coverage depth, such as number of sequence representations, for on-target regions can be greater than the coverage depth for off-target regions.

The discrepancy between coverage depth of on-target regions and off-target regions can cause an amount of noise to be present in sequence data that includes both on-target sequence representations and off-target sequence representation. The amount of noise can result in inaccuracies of tumor metrics generated using the process 300. In order to reduce the noise present when on-target sequence data is used to perform the first segmentation process 316 and to increase the accuracy of tumor metrics generated by the process 300, the first segmentation process 316 is performed using the off-target sequence data 314.

The first segmentation process can generate a number of first segments of the reference sequence 302, such as the illustrative first segment 318. In one or more illustrative examples, the first segments 318 can include no greater than about 200 kilobases (kb), no greater than about 180 kb, no greater than about 160 kb, no greater than about 140 kb, no greater than about 120 kb, no greater than about 100 kb, no greater than about 80 kb, or no greater than about 60 kb. In one or more additional illustrative examples, the first segments 318 can include at least about 50 kb, at least about 60 kb, at least about 70 kb, at least about 80 kb, at least about 90 kb, at least about 100 kb, at least about 120 kb, at least about 140 kb, at least about 160 kb, or at least about 180 kb. In various examples, at least a portion of the plurality of first segments 318 can have a same number of nucleotides and a remainder of the plurality of first segments 318 can have fewer nucleotides. In one or more illustrative examples, a first number of the first segments 318 can have 200 kb and a second number of the first segments 318 can have less than 200 kb. In one or more additional examples, at least about 70% of the plurality of first segments 318 have a same number of nucleotides, at least about 75% of the plurality of first segments 318 have a same number of nucleotides, at least about 80% of the plurality of first segments 318 have a same number of nucleotides, at least about 85% of the plurality of first segments 318 have a same number of nucleotides, at least about 90% of the plurality of first segments 318 have a same number of nucleotides, at least about 95% of the plurality of first segments 318 have a same number of nucleotides, or at least about 99% of the plurality of first segments 318 have a same number of nucleotides. In one or more further examples, the first segmentation process of the reference sequence 302 can be performed such that the plurality of first segments 318 exclude the target regions. In these implementations, the plurality of first segments 318 do not overlap with the target regions.

The number of first segments 318 of the reference sequence 302 can be at least about 7000, at least about 8000, at least about 9000, at least about 10,000, at least about 11,000, at least about 12,000, at least about 13,000, at least about 14,000, at least about 15,000, at least about 16,000, at least about 17,000, at least about 18,000, at least about 19,000, at least about 20,000, at least about 21,000, at least about 22,000, at least about 23,000, at least about 24,000, at least about 25,000, or at least about 26,000. In one or more illustrative examples, the number of first segments 318 of the reference sequence 302 can be from about 7000 to about 35,000, from about 10,000 to about 30,000, or from about 12,000 to about 27,000.

In one or more examples, the process 300 can include determining coverage data 320 for individual first segments 318. The coverage data 320 for individual first segments 318 can include a number of off-target sequence representations that have at least a threshold amount of homology with the individual first segments 318. The coverage data generated for the first segments 318 can be used to produce first segments coverage data 322. In various examples, the first segments coverage data 322 can include the number of off-target sequence representations that correspond to the individual first segments 318. In one or more illustrative examples, the number of off-target sequence representations corresponding to an individual first segment 318 can be on the order of hundreds of off-target sequence representations, up to thousands and tens of thousands off-target sequence representations.

In various examples, the first segments coverage data 322 can exclude the coverage information for one or more of the first segments 318. In this way, the one or more first segments 318 used to determine the first segments coverage data 322 can be filtered. The filtering of the first segments 318 can be performed based on the off-target sequence data 314. In one or more additional examples, the filtering of the first segments 318 can be performed based on off-target sequence representation data generated from reference samples obtained from individuals in which a copy number variation is not detected In one or more examples, first segments 318 having coverage information that is at least one of one standard deviation, two standard deviations, three standard deviations, or four standard deviations above or below a reference median coverage metric, can be excluded from the first segments coverage data 322. In one or more illustrative examples, during a training process using reference samples, first segments 318 having coverage information that is at least one of one standard deviation, two standard deviations, three standard deviations, or four standard deviations above or below a reference median coverage metric, can be excluded from determining the first segments coverage data 322. In one or more further examples, one or more first segments that correspond to an X chromosome and/or Y chromosome can be excluded from the first segments coverage data 324.

Further, first segments 318 having at least a threshold amount of overlap with target regions of the reference sequence 302 can be determined. In scenarios where one or more first segments 318 have at least the threshold amount of overlap with target regions of the reference sequence 302, the coverage information that corresponds to the one or more first segments 318 can be excluded from the first segments coverage data 322. In various examples, the threshold amount of overlap between target regions of the reference sequence 302 and one or more of the first segments 318 can include at least about 5 nucleotides of a first segment 318 overlap with a target region of the reference sequence 302, at least about 10 nucleotides of a first segment 318 overlap with a target region of the reference sequence 302, at least about 15 nucleotides of a first segment 318 overlap with a target region of the reference sequence 302, at least about 20 nucleotides of a first segment 318 overlap with a target region of the reference sequence 302, or at least about 25 nucleotides of a first segment 318 overlap with a target region of the reference sequence 302.

First segments 318 having a threshold amount of overlap with target regions can be excluded from the first segments coverage data 322 due to the amount of noise that can be generated when data from these first segments 318 is included in the first segments coverage data 322. In one or more examples, the amount of coverage, such as the number of sequence representations, for first segments 318 that have a threshold amount of overlap with target regions can be greater than the amount of coverage for first segments 318 that do not have the threshold amount of overlap with one or more target regions. In one or more illustrative examples, the consider only off-target because coverage depth is different for off-target and on-target combined it is too noisy. Average coverage is 300-400. Noise is too much. Difference in coverage between on-target and off-target. That's why we don't bring them together until the second segmentation In one or more further examples, the first segments coverage data 322 can exclude sequence representations for one or more of the first segments 318 in situations where an amount of variation between the coverage data with respect to a first segment and a number of additional first segments 318 is greater than a threshold amount of variation with respect to off-target sequence representation data generated from reference samples obtained from individuals in which a copy number variation is not detected. For example, a first segment 318 having a measure of coverage for reference sequence representations that is at least one standard deviation, at least two standard deviations, at least three standard deviations, or at least four standard deviations from a mean of coverage data for the reference sequence representations can be excluded from the first segments coverage data 318.

In one or more additional implementations, coverage information of one or more first segments that have fewer than a threshold number of sequence representations can also be excluded from the first segments coverage data 322. In one or more illustrative examples, the threshold number of sequence representations present in a first segment 318 in order to exclude coverage information of the respective first segment 318 from the first segments coverage data 322 is 0, 1, 2, 3, 4, 5, 8, 10, 12, 15, 20, 25, 35, 50, 75, or 100. In various examples, the coverage data used to determine whether to exclude a respective first segment 318 from determining the first segments coverage data 322 can be based on reference coverage data of the first segments 318 corresponding to reference samples obtained from individuals in which copy number variation is not detected.

Additionally, at operation 324, the process 300 can include normalizing the first segments coverage data 322 to produce normalized coverage data 326. The normalized coverage data 326 can be generated by analyzing the first segments coverage data 322 with respect to reference coverage data. In one or more examples, the reference coverage data can be determined based on off-target sequences that are generated based on a number of samples obtained from individuals in which copy number variation is not present. In various examples, the reference coverage data can be determined by analyzing sequence data obtained from reference samples of individuals in which copy number variation is not present to determine off-target sequence representations generated from the reference samples that do not align with target regions of the reference sequence 302. Reference coverage data for first segments 318 of the reference sequence 302 can be produced by determining a respective number of off-target sequence representations derived from the reference samples that are included in individual first segments 318. In one or more illustrative examples, the reference coverage data for a given first segment 318 can be determined based on an average number of off-target sequence representations derived from a plurality of reference samples with respect to the given first segment 318. For individual first segments 318, normalized coverage data can be generated by determining a ratio of the number of off-target sequence representations included in the individual first segments coverage data 322 in relation to the reference coverage data for the individual first segments 318. The normalized coverage data 326 can be produced by aggregating the ratios of the number of off-target sequence representations included in the first segments coverage data 322 in relation to the reference coverage data for the individual first segments 318.

The normalization of the first segments coverage data 322 can also be performed with respect to at least one of guanine-cytosine (G-C) content or mappability scores. For example, for individual first segments 318, G-C content can be determined that indicates a number of guanine nucleotides and a number of cytosine nucleotides of off-target sequence representations that correspond to the individual first segments 318. In addition, frequency of G-C content can be determined for a partition of G-C content of a plurality of partitions. Individual partitions of G-C content can correspond to different ranges of values of G-C content. In this way, the frequency of G-C content for a given first segment 318 can be represented by a G-C content distribution for individual first segments 318. An expected amount of coverage for individual first segments 318 can be determined based on the frequency of G-C content for the individual first segments 318. At least a portion of the normalized coverage data 326 can include G-C normalized coverage data that is determined based on the expected amount of coverage for individual first segments 318.

Further, a mappability score can be determined for individual sequence representations that correspond to individual first segments 318. A frequency of sequence representations can also be determined that corresponds to a number of sequence representations having a mappability score within a partition of a plurality of partitions for an individual first segment 318. Individual partitions of mappability scores of the plurality of partitions for individual first segments 318 can correspond to a different range of values of mappability scores. An expected amount of coverage for individual first segments 318 can be determined based on the frequency of mappability scores for the individual first segments 318. At least a portion of the normalized coverage data 326 can mappability score normalized coverage data that is determined based on the expected amount of coverage for individual first segments 318.

In various examples, the normalized coverage data 326 can include a combination of normalized data corresponding to at least one of G-C content normalized data, mappability score normalized data, coverage data normalized according to reference coverage data, or coverage data normalized according to median coverage data. In one or more examples, a normalization performed in relation to a first set of data can be adjusted based on a normalization performed in relation to one or more additional sets of data to produce a final normalized value for the coverage metrics of a first segment 318. For example, a first normalization of first segments 318 can be performed with respect to first segments coverage data 322 for an individual first segment 318 in relation to median coverage data generated from a plurality of the first segments 318. In one or more examples, the first normalization can result in a first ratio for the individual first segment 318. Continuing with this example, a second normalization can be performed with respect to first segments coverage data 322 for the individual first segment 318 in relation to reference coverage data for the individual first segment 318 derived from a number of reference samples. In one or more additional examples, the second normalization can result in a second ratio for the individual first segment 318. In these situations, the first normalized coverage data for the individual first segment 318 generated after the first normalization can be adjusted based on second normalized coverage data for the individual first segment 318 generated after the second normalization to produce first adjusted normalized coverage data.

A third normalization can take place with respect to G-C content of the individual first segment 318 in relation to G-C content of a plurality of additional first segments 318 (e.g., median G-C content) or in relation to G-C content derived from reference samples. The results of the third normalization can include a third ratio. In various examples, the second normalized coverage data can be adjusted based on the G-C content normalized data to produce second adjusted normalized coverage data. Further, a fourth normalization can be performed with respect to the mappability scores to produce mappability score normalized data. The second adjusted normalized coverage data can be further adjusted based on the mappability score normalized data to generate third adjusted normalized coverage data. In various examples, at least one of the first normalized coverage data, the first adjusted normalized coverage, the second adjusted normalized coverage data, or the third adjusted normalized coverage data can be included in the normalized coverage data 326.

In one or more examples, the process 324 of normalizing the coverage data can including one or more operations that apply a scaling factor to the first segments coverage data 322. In one or more additional examples, the scaling factor can be applied to on-target coverage data. The scaling factor can be determined by dividing the coverage data for a given first segment 118 by a median of coverage data for a group of first segments 318. In one or more illustrative examples, the group of first segments 318 can include at least about 90% of the first segments 318, at least about 95% of the first segments 318, at least about 99% of the first segments, at least about 99.5% of the first segments 318, or at least about 99.9% of the first segments 318.

The process 300 can include, at operation 328, performing a second segmentation process with respect to the reference sequence 302. The second segmentation process can partition the reference sequence 302 into a number of second segments, such as an illustrative second segment 330. Individual second segments 330 can include a plurality of first segments 318. In one or more examples, individual second segments 330 can include at least 30 first segments 318, at least 35 first segments 318, at least 40 first segments 318, at least 45 first segments 318, at least 50 segments 318, at least 55 first segments 318, or at least 60 first segments 318. In one or more illustrative examples, individual second segments 330 can include a greater number of nucleotides than individual first segments 318. For example, individual second segments 330 can include at least about 2 million nucleotides, at least about 3 million nucleotides, at least about 4 million nucleotides, at least about 5 million nucleotides, at least about 6 million nucleotides, or at least about 7 million nucleotides. In one or more illustrative examples, individual second segments 330 can include from about 2 million nucleotides to about 12 million nucleotides, from about 3 million nucleotides to about 10 million nucleotides, or from about 4 million nucleotides to about 8 million nucleotides. In various examples, at least one or more of the second segments 330 can have a different number of nucleotides than at least one additional one of the second segments 330. In various examples the second segmentation process can include one or more circular binary segmentation processes, such as those described by Olshen, Adam et al., "Circular binary segmentations for the analysis of array-based DNA copy number data", Biostatistics, 2004 October; 5(4): 557-72.

A number of the second segments 330 that are determined as part of the second segmentation process can be at least 5, at least 7, at least 10, at least 12, at least 15, at least 16, at least 17, at least 18, at least 19, at least 20, at least 21, at least 22, at least 23, at least 24, or at least 25. In one or more illustrative examples, the number of second segments 330 determined as part of the second segmentation process can be from 5 to 30, from 10 to 27, or from 18 to 24.

Subsequent to completion of the second segmentation process, second segments coverage data 332 can be determined. The second segments coverage data 332 for individual second segments 330 can comprise the normalized coverage metrics for each first segment 318 included an individual second segment 330. In one or more illustrative examples, the second segments coverage data 332 for an individual second segment 330 can correspond to a sum of the normalized coverage metrics for the plurality of first segments 318 that comprise the second segment 330. At operation 334, tumor metrics can be determined based on the second segments coverage data. 332. For example, tumor cells copy number for a sample from which the off-target sequence representations are derived can be determined based on the second segments coverage data 332. The tumor cells copy number for individual second segments 330 can indicate an amount of amplification or deletion of a genomic region that corresponds to one or more of the individual second segments 330. In various examples, the tumor cells copy number can indicate a loss of heterozygosity of a genomic region that corresponds to one or more of the individual second segments 330. Additionally, the tumor fraction can also be determined upon completion of the second segmentation process. In one or more illustrative examples, the tumor metrics can comprise values of parameters of a model that can be used to determine a likelihood of the values of the tumor cells copy number and tumor fraction. To illustrate, the second segmentation process can result in 23 segments. In these scenarios, the tumor metrics can include 23 tumor cells copy numbers that each correspond to a respective second segment 23. The 23 tumor cells copy numbers along with the tumor fraction determined based on the second segments coverage data 332 can comprise values of parameters for a maximum likelihood estimation model that determines the likelihood for the estimated values of the tumor cells copy number and the tumor fraction.

In one or more examples, the first segmentation process 316 and the second segmentation process 328 can be repeated for at least a portion of the second segments 330 that do not satisfy one or more criteria. For example, the likelihood of a tumor cells copy number for one or more second segments 330 can be less than a minimum likelihood after a first iteration of the first segmentation process 316 and the second segmentation process 328. In one or more additional examples, the one or more criteria can correspond to whether or not the estimate of the tumor cells copy number is changing from one iteration of the segmentations processes to the next iteration.

In these situations, the first segmentation process 316 and the second segmentation process 328 can be repeated for the one or more second segments that do not satisfy the one or more criteria, while the first segmentation process 316 and the second segmentation process 328 are not repeated for the second segments 330 that do satisfy the one or more criteria. To illustrate, the portions of the reference sequence 302 that correspond to the one or more second segments 330 that do not satisfy the one or more criteria, can be segmented into additional first segments. In various examples, the second segmentations process can be performed with respect to second segments having a same or consistent copy number in relation to an expected copy number for the segment. The expected copy number can be based on the copy number of a reference genome for the respective segments. Additional coverage data can be determined for the additional first segments and one or more normalization processes can be performed with respect to the additional coverage data of the additional first segments. In one or more illustrative examples, additional normalized coverage data can be determined by implementing at least one of a G-C content normalization process, a mappability score normalization process, or coverage data normalization process according to reference coverage data.

Subsequent to determining additional normalized coverage data, an additional implementation of the second segmentation process can be performed in relation to the additional first segments using the additional normalized coverage data to determine one or more additional second segments. Additional second segments coverage data can be determined for the one or more additional second segments based on the additional normalized coverage date. The additional segments coverage data for the additional second segments can be used to determine tumor cells copy number for the additional second segments. The initial tumor cells copy number for the initial second segments can be combined with the additional tumor cells copy number and be used as parameters for a maximum likelihood estimation model. Further, the coverage data for the initial second segments and the additional second segments can be combined to determine a value for tumor fraction of the sample. The value for the tumor fraction of the sample can also be used as a parameter for the maximum likelihood estimation model.

In one or more implementation, to determine the estimates for the tumor cells copy number of the second segments 330, first estimates for tumor cells copy numbers for the second segments 330 can be determined based on the second segments coverage data 332. An additional first segmentation process can be performed to determine additional first segments. In various examples, at least a portion of the additional first segments can be located in a same genomic location of the reference genome 302 as respective first segments 318. Additional normalized coverage data can also be determined based on additional first segments coverage data determined according to respective numbers of sequence representations that correspond to the additional first segments. The additional normalized coverage data can be used to perform an additional second segmentation process and additional second segments coverage data can be determined. In one or more examples, at least a portion of the additional second segments can be located in a same genomic location of the reference genome 302 as respective second segments 330. The additional second segments coverage data can be used to determine second estimates for the tumor cells copy number for the additional second segments.

The second estimates for the tumor cells copy number can be analyzed with respect to the first estimates for the tumor cells copy number. In situations where the second estimate for tumor cells copy number of an additional second segment is different from the first estimate of tumor cells copy number for a corresponding second segment, a third iteration of the first segmentation process and the second segmentation process can be performed, along with a determination of second additional first segments coverage data, second additional normalized coverage data, and second additional second coverage data. In scenarios where the second estimate for tumor cells copy number of an additional second segment is the same as the first estimate of tumor cells copy number for a corresponding second segment, a determination can be made that the tumor cells copy number for the respective second segment is unchanged and satisfies the one or more criteria for determining the estimate of tumor cells copy number for the respective second segment. In one or more illustrative examples, the tumor cells copy number for a second segment can be considered to be unchanged in response to determining that the estimates for the tumor cells copy number are the same after multiple iterations of the first segmentation process and the second segmentation process. In various examples, the initial conditions for each iteration of the first segmentation process and the second segmentation process can be different. Additionally, determining that the estimates for tumor cells copy number of the second segments is unchanged can be based on one or more circular binary segmentation techniques.

Figure 4:
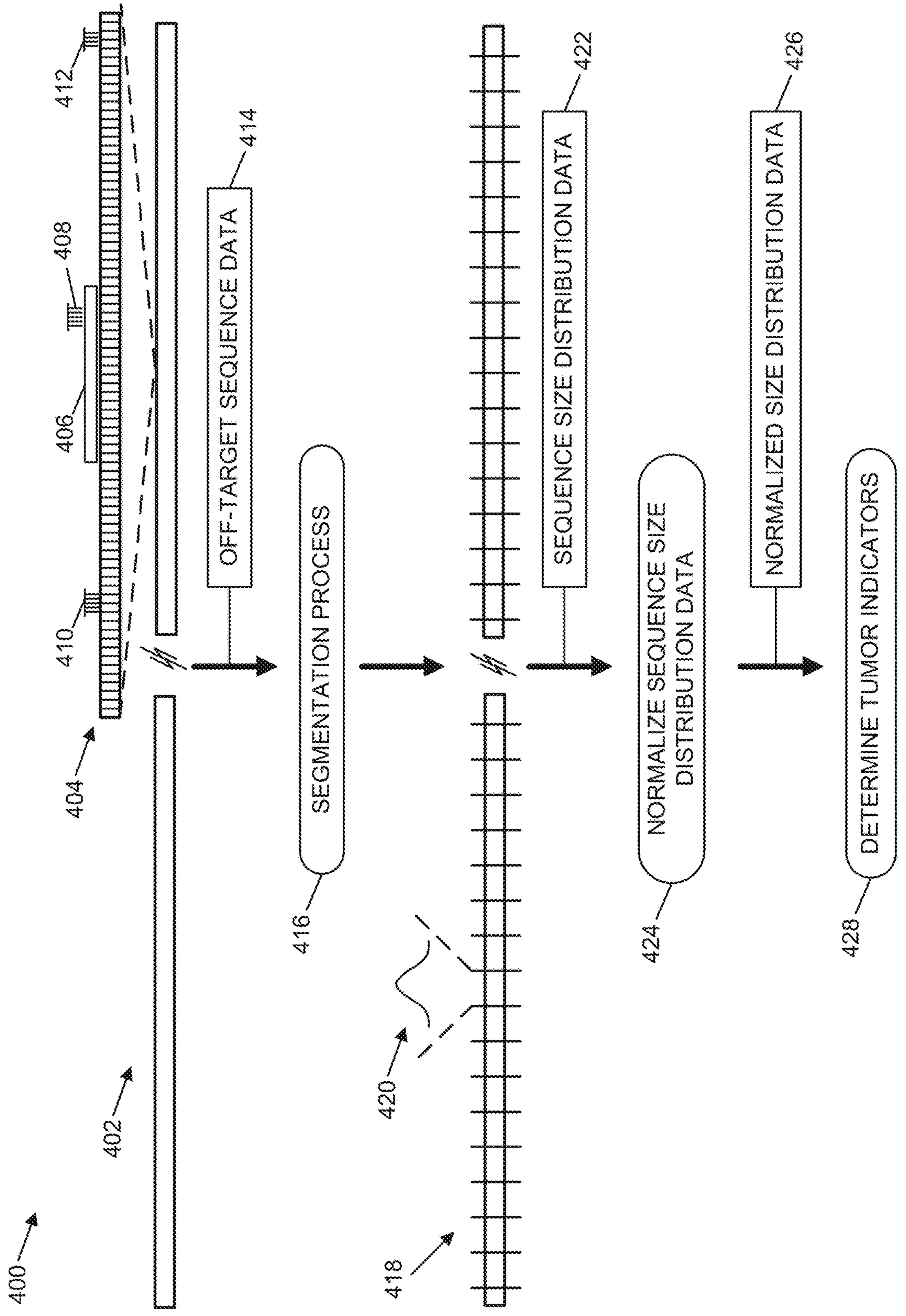
FIG. 4 is a diagrammatic representation of an example process to determine tumor metrics related to a subject based on size distribution metrics derived from off-target polynucleotides, according to one or more implementations.

FIG. 4 is a diagrammatic representation of an example process to determine tumor metrics determined from size distribution metrics derived from off-target sequences, according to one or more implementations. The process 400 can include determining on-target sequence representations and off-target sequence representations based on sequencing data that includes polynucleotide sequences derived from a sample obtained from a subject. In one or more examples, on-target sequence representations and off-target sequence representations can be determined by analyzing sequence representations with respect to a reference sequence 402. To illustrate, sequence representations can be analyzed with respect to one or more portions of the reference sequence 402, such as an illustrative reference sequence portion 404, to determine an amount of homology between the sequence representations and the illustrative reference sequence portion 404. In the illustrative example of FIG. 4, the illustrative reference sequence portion 404 can include a target region 406 that corresponds to a driver mutation. In various examples, the reference sequence 402 can have at least about 500 target regions, at least about 1000 target regions, at least about 2500 target regions, at least about 5000 target regions, at least about 10,000 target regions, at least about 15,000 target regions, at least about 20,000 target regions, at least about 25,000 target regions, or at least about 30,000 target regions. The target region 406 can include from about 25 nucleotides to about 250 nucleotides, from about 50 nucleotides to about 200 nucleotides, or from about 75 nucleotides to about 150 nucleotides.

Additionally, in the illustrative example of FIG. 4, a first sequence representation 408, a second sequence representation 410, and a third sequence representation 412 are analyzed with respect to the illustrative reference sequence portion 404. Based on the analysis, the first sequence representation 408 is aligned with respect to at least a portion of the target region 406. In these scenarios, the first sequence representation 408 can be identified as an on-target sequence representation. Further, the second sequence representation 410 can be aligned with a portion of the illustrative reference sequence portion 404 that is outside of the target region 406. The third sequence representation 412 can also be aligned with an additional portion of the illustrative reference sequence portion 404 that is outside of the target region 406. In these situations, the second sequence representation 410 and the third sequence representation 412 can be identified as off-target sequence representations.

The alignment process between sequence representations derived from a sample and the reference sequence 402 can generate off-target sequence data 414. The off-target sequence data 414 can include sequence representations that are aligned with regions of the reference sequence 402 that are outside of target regions. For example, the off-target sequence data 414 can include the second sequence representation 410 and the third sequence representation 412.

The process 400 can include, at operation 416, a first segmentation process that is performed based on the off-target sequence data 414. The first segmentation process can generate a number of first segments of the reference sequence 402, such as the illustrative first segment 418. The first segmentation process is performed such that the first segments 418 of the reference sequence 402 have no greater than a threshold number of number of nucleotides. In one or more illustrative examples, the threshold number of nucleotides can be no greater than about 200 kilobases (kb), no greater than about 180 kb, no greater than about 160 kb, no greater than about 140 kb, no greater than about 120 kb, no greater than about 100 kb, no greater than about 80 kb, or no greater than about 60 kb. In one or more additional illustrative examples, the first segments 318 can include at least about 50 kb, at least about 60 kb, at least about 70 kb, at least about 80 kb, at least about 90 kb, at least about 100 kb, at least about 120 kb, at least about 140 kb, at least about 160 kb, or at least about 180 kb. In various examples, at least a portion of first segments 418 can have a same number of nucleotides and a remainder of the plurality of first segments 418 can have fewer nucleotides. In one or more illustrative examples, at least a portion of the plurality of first segments 418 can have 200 kb and a remainder of the plurality of first segments 418 can have fewer nucleotides. In one or more additional examples, at least about 70% of the plurality of first segments 418 can have a same number of nucleotides, at least about 75% of the plurality of first segments 418 can have a same number of nucleotides, at least about 80% of the plurality of first segments 418 can have a same number of nucleotides, at least about 85% of the plurality of first segments 418 can have a same number of nucleotides, at least about 90% of the plurality of first segments 418 can have a same number of nucleotides, at least about 95% of the plurality of first segments 418 can have a same number of nucleotides, or at least about 99% of the plurality of first segments 418 can have a same number of nucleotides. In one or more further examples, the first segmentation process of the reference sequence 402 can be performed such that the plurality of first segments 418 exclude the target regions. In these implementations, the plurality of first segments 418 do not overlap with the target regions.

The number of first segments 418 of the reference sequence 402 can be at least about 7000, at least about 8000, at least about 9000, at least about 10,000, at least about 11,000, at least about 12,000, at least about 13,000, at least about 14,000, at least about 15,000, at least about 16,000, at least about 17,000, at least about 18,000, at least about 19,000, at least about 20,000, at least about 21,000, at least about 22,000, at least about 23,000, at least about 24,000, at least about 25,000, or at least about 26,000. In one or more illustrative examples, the number of first segments 418 of the reference sequence 402 can be from about 7000 to about 35,000, from about 10,000 to about 30,000, or from about 12,000 to about 27,000.

In one or more examples, the process 400 can include determining a size distribution 420 for individual first segments 418. The size distribution 420 for individual first segments 418 can include a number of off-target sequence representations that are included in respective partitions of a distribution of sequence representation sizes. For example, the size distribution 420 can represent a normal distribution of sizes for sequence representations that correspond to a respective first segment 418. In these scenarios, individual partitions can correspond to a range of sizes of sequence representations that are related to a standard deviation from the mean. To illustrate, a first partition of the distribution 420 can include sequence representations having sizes that are one standard deviation greater than the mean and a second partition of the distribution 420 can include sequence representations having sizes that are one standard deviation less than the mean. In addition, a third partition of the distribution 420 can include sequence representations having sizes between one and two standard deviations greater than the mean and a fourth partition of the distribution 420 can include sequence representations having sizes that are between one and two standard deviations less than the mean. The size distribution data generated for the first segments 418 can be used to produce sequence size distribution data 422. In various examples, the sequence size distribution data 422 can include the respective size distributions of off-target sequence representations that correspond to the individual first segments 418.

In various examples, the sequence size distribution data 422 can exclude the coverage information for one or more of the first segments 418. In this way, the one or more first segments 418 used to determine the sequence size distribution data 422 can be filtered. The filtering of the first segments 418 can be performed based on the off-target sequence data 414. In one or more additional examples, the filtering of the first segments 418 can be performed based on off-target sequence representation data generated from reference samples obtained from individuals in which copy number variation is not present.

Further, first segments 418 having at least a threshold amount of overlap with target regions of the reference sequence 402 can be determined. In scenarios where one or more first segments 418 have at least the threshold amount of overlap with target regions of the reference sequence 402, the sequence size distribution information that corresponds to the one or more first segments 418 can be excluded from the sequence size distribution data 422. In various examples, the threshold amount of overlap between target regions of the reference sequence 402 and one or more of the first segments 418 can include at least about 5 nucleotides of a first segment 418 overlap with a target region of the reference sequence 402, at least about 10 nucleotides of a first segment 418 overlap with a target region of the reference sequence 402, at least about 15 nucleotides of a first segment 418 overlap with a target region of the reference sequence 402, at least about 20 nucleotides of a first segment 418 overlap with a target region of the reference sequence 402, or at least about 25 nucleotides of a first segment 418 overlap with a target region of the reference sequence 402.

In one or more additional implementations, size distribution information of one or more first segments 418 that have fewer than a threshold number of sequence representations can also be excluded from the sequence size distribution data 422. In one or more illustrative examples, the threshold number of sequence representations present in a first segment 418 in order to exclude sequence size distribution information of the respective first segment 418 from the sequence size distribution data 422 is 0, 1, 2, 3, 4, 5, 8, 10, 12, 15, 20, 25, 35, 50, 75, or 100. In various examples, the sequence size distribution information used to determine whether to exclude a respective first segment 418 from determining the sequence size distribution data 422 can be based on reference sequence size distribution data of the first segments 418 corresponding to reference samples obtained from individuals in which copy number variation is not detected.

Additionally, at operation 424, the process 400 can include normalizing the sequence size distribution data 422 to produce normalized size distribution data 426. The normalized size distribution data 426 can be generated by analyzing the sequence size distribution data 422 with respect to reference size distribution data. In one or more examples, the reference size distribution data can be determined based on off-target sequence representations that are generated based on a number of samples obtained from individuals in which a tumor is not present. In various examples, the reference size distribution data can be determined by analyzing sequencing data obtained from reference samples of individuals in which copy number variation is not present to determine off-target sequence representations generated from the reference samples that do not align with target regions of the reference sequence 402. Reference size distribution data for first segments 418 of the reference sequence 402 can be produced by determining a respective number of off-target sequence representations derived from the reference samples that are included in respective partitions of a distribution in relation to the individual first segments 418. In one or more illustrative examples, the reference size distribution data for a given first segment 418 can be determined based on an average number of off-target sequence representations derived from a plurality of reference samples with respect to individual partitions of a distribution for the given first segment 418. For individual first segments 418, normalized size distribution data can be generated by determining a ratio of the size distribution data from a given first segment 418 derived from the sequence size distribution data 422 in relation to the reference size distribution data for the individual first segments 418. The normalized size distribution data 426 can be produced by aggregating the ratios of the size distribution data from a given first segment 418 derived from the sequence size distribution data 422 in relation to the reference size distribution data for the individual first segments 418.

Although not shown in the illustrative example of FIG. 4, the process 400 can include performing a second segmentation process with respect to the reference sequence 402. The second segmentation process can partition the reference sequence 402 into a number of second segments. Individual second segments can include a plurality of first segments 418. In one or more examples, individual second segments can include at least 30 first segments 418, at least 35 first segments 418, at least 40 first segments 418, at least 45 first segments 418, at least 50 segments 418, at least 55 first segments 418, or at least 60 first segments 418. In one or more illustrative examples, individual second segments can include a greater number of nucleotides than individual first segments 418. For example, individual second segments can include at least about 2 million nucleotides, at least about 3 million nucleotides, at least about 4 million nucleotides, at least about 5 million nucleotides, at least about 6 million nucleotides, or at least about 7 million nucleotides. In one or more illustrative examples, individual second segments can include from about 2 million nucleotides to about 12 million nucleotides, from about 3 million nucleotides to about 10 million nucleotides, or from about 4 million nucleotides to about 8 million nucleotides. In various examples, at least one or more of the second segments can have a different number of nucleotides than at least one additional one of the second segments. In various examples the second segmentation process can include one or more circular binary segmentation processes, such as those described by Olshen, Adam et al., "Circular binary segmentations for the analysis of array-based DNA copy number data", Biostatistics, 2004 October; 5(4): 557-72.

A number of the second segments that are determined as part of the second segmentation process can be at least 5, at least 7, at least 10, at least 12, at least 15, at least 16, at least 17, at least 18, at least 19, at least 20, at least 21, at least 22, at least 23, at least 24, or at least 25. In one or more illustrative examples, the number of second segments determined as part of the second segmentation process can be from 5 to 30, from 10 to 27, or from 18 to 24.

Subsequent to completion of the second segmentation process, second size distribution data can be determined. The second size distribution data for individual second segments of the reference genome 402 can comprise the normalized coverage metrics for each first segment 418 included an individual second segment. In one or more illustrative examples, the second size distribution data for an individual second segment can correspond to a sum of the normalized coverage metrics for the plurality of first segments 418 that comprise the second segment. Further, at operation 428, tumor metrics can be determined based on the second size distribution data. For example, tumor cells copy number for a sample from which the off-target sequence representations are derived can be determined based on the second size distribution data. The tumor cells copy number for individual second segments can indicate an amount of amplification or deletion of a genomic region that corresponds to one or more of the individual second segments. In various examples, the tumor cells copy number can indicate a loss of heterozygosity of a genomic region that corresponds to one or more of the individual second segments. Additionally, the tumor fraction can also be determined upon completion of the second segmentation process. In one or more illustrative examples, the tumor metrics can comprise values of parameters of a model that can be used to determine a likelihood of the values of the tumor cells copy number and tumor fraction. To illustrate, the second segmentation process can result in 23 segments. In these scenarios, the tumor metrics can include 23 tumor cells copy numbers that each correspond to a respective second segment 23. The 23 tumor cells copy numbers along with the tumor fraction determined based on the second size distribution data can comprise values of parameters for a maximum likelihood estimation model that determines the likelihood for the estimated values of the tumor cells copy number and the tumor fraction.

In one or more examples, the first segmentation process 416 and the second segmentation process can be repeated for at least a portion of the second segments that do not satisfy one or more criteria. For example, the likelihood of a tumor cells copy number for one or more second segments can be less than a minimum likelihood after a first iteration of the first segmentation process 416 and the second segmentation process. In these situations, the first segmentation process 416 and the second segmentation process can be repeated for the one or more second segments that do not satisfy the one or more criteria, while the first segmentation process 416 and the second segmentation process are not repeated for the second segments that do satisfy the one or more criteria. To illustrate, the portions of the reference sequence 402 that correspond to the one or more second segments that do not satisfy the one or more criteria, can be segmented into additional first segments. Additional coverage data can be determined for the additional first segments and one or more normalization processes can be performed with respect to the additional coverage data of the additional first segments.

In one or more illustrative examples, additional normalized coverage data can be determined by implementing a size distribution data normalization process according to reference size distribution data.

Subsequent to determining additional normalized size distribution data, an additional implementation of the second segmentation process can be performed in relation to the additional first segments using the additional normalized size distribution data to determine one or more additional second segments. Additional second segments size distribution data can be determined for the one or more additional second segments based on the additional normalized size distribution date. The additional segments size distribution data for the additional second segments can be used to determine tumor cells copy number for the additional second segments. The initial tumor cells copy number for the initial second segments can be combined with the additional tumor cells copy number and be used as parameters for a maximum likelihood estimation model. Further, the size distribution data for the initial second segments and the additional second segments can be combined to determine a value for tumor fraction of the sample. The value for the tumor fraction of the sample can also be used as a parameter for the maximum likelihood estimation model.

In one or more implementations, to determine the estimates for the tumor cells copy number of the second segments of the reference genome 402, first estimates for tumor cells copy numbers for the second segments can be determined based on second segments size distribution data. An additional first segmentation process can be performed to determine additional first segments. In various examples, at least a portion of the additional first segments can be located in a same genomic location of the reference genome 402 as respective first segments 418. Additional normalized size distribution data can also be determined based on additional first segments size distribution data determined according to respective numbers of sequence representations that correspond to the additional first segments. The additional normalized size distribution data can be used to perform an additional second segmentation process and additional second segments size distribution data can be determined. In one or more examples, at least a portion of the additional second segments can be located in a same genomic location of the reference genome 402 as respective second segments. The additional second segments size distribution data can be used to determine second estimates for the tumor cells copy number for the additional second segments.

The second estimates for the tumor cells copy number can be analyzed with respect to the first estimates for the tumor cells copy number. In situations where the second estimate for tumor cells copy number of an additional second segment is different from the first estimate of tumor cells copy number for a corresponding second segment, a third iteration of the first segmentation process and the second segmentation process can be performed, along with a determination of second additional first segments size distribution data, second additional normalized size distribution data, and second additional second size distribution data. In scenarios where the second estimate for tumor cells copy number of an additional second segment is the same as the first estimate of tumor cells copy number for a corresponding second segment, a determination can be made that the tumor cells copy number for the respective second segment is unchanged and satisfies the one or more criteria for determining the estimate of tumor cells copy number for the respective second segment. In one or more illustrative examples, the tumor cells copy number for a second segment can be considered to be unchanged in response to determining that the estimates for the tumor cells copy number are the same after multiple iterations of the first segmentation process and the second segmentation process. In various examples, the initial conditions for each iteration of the first segmentation process and the second segmentation process can be different. Additionally, determining that the estimates for tumor cells copy number of the second segments is unchanged can be based on one or more circular binary segmentation techniques.

Figure 5:
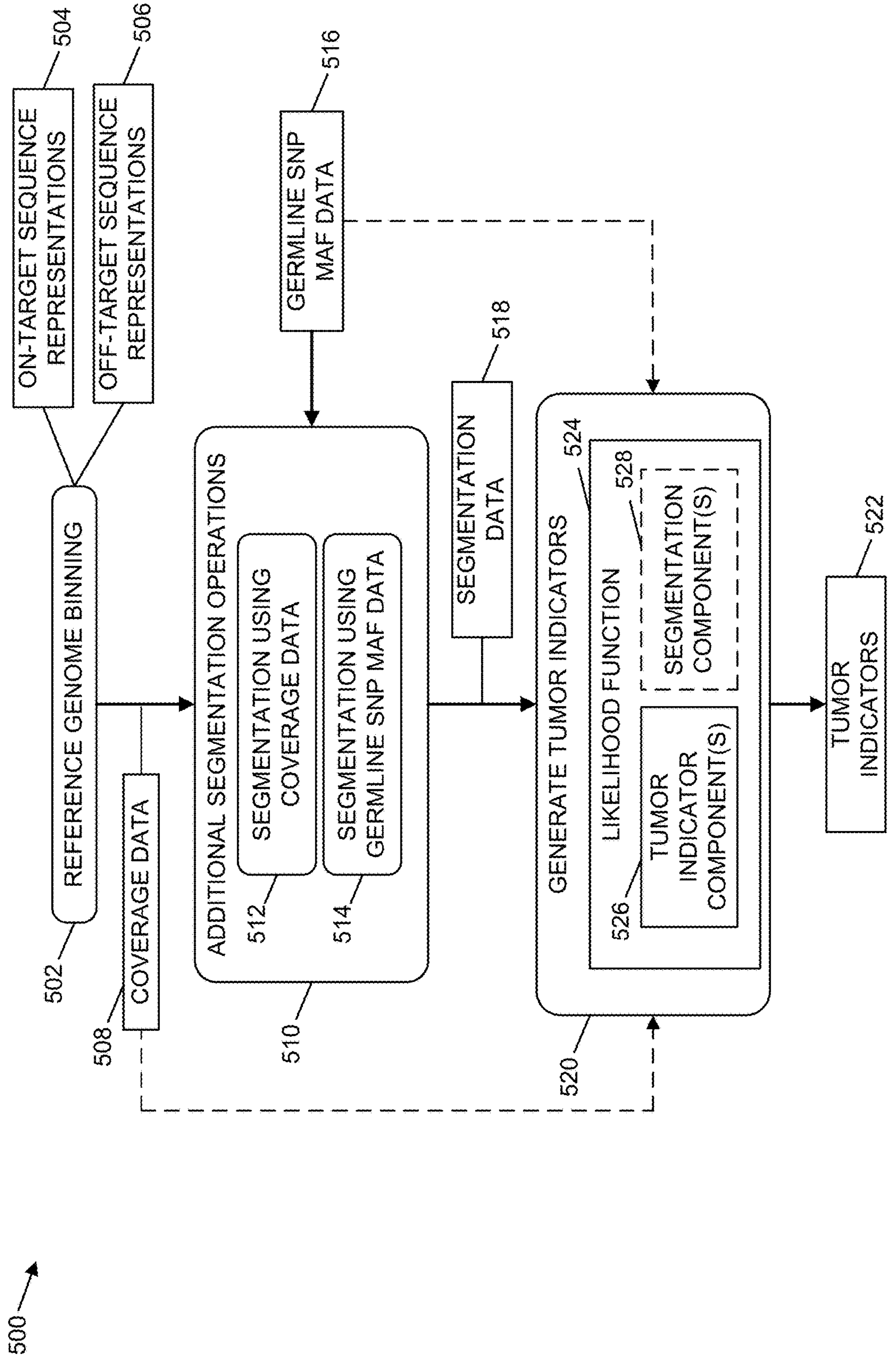
FIG. 5 is a diagrammatic representation of an example process to determine tumor metrics using a binning operation, one or more additional segmentation operations, and a likelihood function.

FIG. 5 is a diagrammatic representation of an example process 500 to determine tumor metrics using a binning operation, one or more additional segmentation operations, and a likelihood function. The process 500, at operation 502, includes reference genome binning. The reference genome binning can include determining bins along a sequence of nucleotides of a reference genome where the bins are comprised of a number of nucleic acids. In one or more examples, individual bins can include no greater than about 200 kb, no greater than about 180 kb, no greater than about 160 kb, no greater than about 140 kb, no greater than about 120 kb, no greater than about 100 kb, no greater than about 80 kb, or no greater than about 60 kb. In one or more additional illustrative examples, the first segments 318 can include at least about 50 kb, at least about 60 kb, at least about 70 kb, at least about 80 kb, at least about 90 kb, at least about 100 kb, at least about 120 kb, at least about 140 kb, at least about 160 kb, or at least about 180 kb. In various examples, at least a portion of the bins can have a same number of nucleotides and a remainder of the bins can have fewer nucleotides. In one or more illustrative examples, a first number of the bins can have 200 kb and a second number of the bins can have less than 200 kb. In one or more additional examples, at least about 70% of the bins have a same number of nucleotides, at least about 75% of the bins have a same number of nucleotides, at least about 80% of the bins have a same number of nucleotides, at least about 85% of the bins have a same number of nucleotides, at least about 90% of the bins have a same number of nucleotides, at least about 95% of the bins have a same number of nucleotides, or at least about 99% of the bins have a same number of nucleotides. In various examples, the bins can exclude target regions. For example, the bins can be determined such that individual bins do not overlap with one or more target regions.

In one or more examples, a target region can correspond to a region of the reference sequence that corresponds to a driver mutation. In one or more illustrative examples, individual driver mutations can correspond to a probe that is part of a tumor detection diagnostic test. In various examples, the reference sequence can have at least about 500 target regions, at least about 1000 target regions, at least about 2500 target regions, at least about 5000 target regions, at least about 10,000 target regions, at least about 15,000 target regions, at least about 20,000 target regions, at least about 25,000 target regions, or at least about 30,000 target regions. Individual target regions can include from about 25 nucleotides to about 250 nucleotides, from about 50 nucleotides to about 200 nucleotides, or from about 75 nucleotides to about 150 nucleotides. In one or more examples, the reference sequence can be a human reference sequence.

The number of bins can be at least about 7000, at least about 8000, at least about 9000, at least about 10,000, at least about 11,000, at least about 12,000, at least about 13,000, at least about 14,000, at least about 15,000, at least about 16,000, at least about 17,000, at least about 18,000, at least about 19,000, at least about 20,000, at least about 21,000, at least about 22,000, at least about 23,000, at least about 24,000, at least about 25,000, or at least about 26,000. In one or more illustrative examples, the number of bins can be from about 7000 to about 35,000, from about 10,000 to about 30,000, or from about 12,000 to about 27,000.

The reference genome binning that takes place at operation 502 can generate on-target sequence representations 504 and off-target sequence representations 506. The on-target sequence representations 504 can correspond to at least one of sequence reads derived from a sample or nucleotide molecules included in a sample that are aligned with target regions of a reference sequence. In addition, the off-target sequence representations 506 can correspond to at least one of sequence reads derived from a sample or nucleotide molecules included in a sample that are aligned with respective bins produced by the reference genome binning.

The on-target sequence representations 504 and the off-target sequence representations 506 can be combined to produce coverage data 508. The coverage data 508 can indicate a quantitative measure of sequence representations that correspond to individual bins produced by the reference genome binning and a quantitative measure of sequence representations that correspond to individual target regions. The quantitative measures included in the coverage data 508 can correspond to a number of sequence representations that correspond to an individual bin or an individual target region. In one or more additional examples, the quantitative measures included in the coverage data 508 can correspond to a ratio of the number of sequence representations that correspond to an individual bin or an individual target region with respect to a total number of sequence representations that correspond to the individual bin or the individual target region.

In one or more examples, at least one of the on-target sequence representations 504 or the off-target sequence representations 506 can be filtered to generate the coverage data 508. For example, off-target sequence representations 506 that are aligned with individual bins that are associated with less than a threshold number of sequence representations can be excluded from the coverage data 508. In addition, sequence representations included in the off-target sequence representations 506 that have at least a threshold amount of overlap with one or more target regions can be excluded from the coverage data 508.

The coverage data 508 can be used as part of additional segmentation operations performed at operation 510. In one or more examples, the coverage data 508 can be subjected to one or more normalization techniques before being used as part of the additional segmentation operations performed at operation 510. In one or more illustrative examples, the coverage data 508 can be normalized according to at least one of reference sample coverage data, G-C content, or mappability score. In various examples, the reference sample coverage data can correspond to quantitative measures derived from samples obtained from individuals in which copy number variation is not present. In one or more scenarios, the reference sample coverage data can be generated from off-target sequence representations obtained from individuals in which copy number variation is not present.

The additional segmentations operations performed at operation 510 can include segmentation using the coverage data 508 at operation 512. The segmentation using coverage data performed at operation 512 can include determining segments of the reference sequence that are different from the bins. In one or more examples, the segmentation using the coverage data 508 can partition the reference sequence into at least 30 segments, at least 35 segments, at least 40 segments, at least 45 segments, at least 50 segments, at least 55 segments, or at least 60 segments. In one or more illustrative examples, the segments produced by the segmentation using the coverage data 514 can include a greater number of nucleotides than the bins generated as part of the reference genome binning performed at operation 502. For example, individual segments produced at operation 512 can include at least about 2 million nucleotides, at least about 3 million nucleotides, at least about 4 million nucleotides, at least about 5 million nucleotides, at least about 6 million nucleotides, or at least about 7 million nucleotides. In one or more illustrative examples, individual segments produced at operation 512 can include from about 2 million nucleotides to about 12 million nucleotides, from about 3 million nucleotides to about 10 million nucleotides, or from about 4 million nucleotides to about 8 million nucleotides. In various examples, at least one or more of the segments produced at operation 512 can have a different number of nucleotides than at least one additional one of the segments produced at operation 512. That is, the individual segments generated by the operation 512 using the coverage data 508 can have a variable number of nucleotides. Additionally, the number of nucleotides included in given segments determined at operation 512 can be different across different samples. To illustrate, a first number of nucleotides included in individual segments produced at operation 512 for a first sample obtained from a first individual can be different from a second number of nucleotides included in individual segments produced at operation 512 for a second sample obtained from a second individual. In one or more implementations, for a given group of samples, the number and location of bins produced at operation 502 can be the same, while at least one of the number of segments or the size of the segments produced at operation 512 can vary. In various examples the second segmentation process can include one or more circular binary segmentation processes, such as those described by Olshen, Adam et al., "Circular binary segmentations for the analysis of array-based DNA copy number data", Biostatistics, 2004 October; 5(4): 557-72.

Further, the additional segmentation operations at operation 510 can include, at operation 514, segmentation using germline SNP mutant allele frequency (MAF) data 516. The germline SNP MAF data 516 can correspond to heterozygous germline SNPs. In one or more illustrative examples, the germline SNP MAF data 516 can include heterozygous germline SNPs identified using the Genome Aggregation Database, version2.1.1. In addition, the germline SNP MAF data 516 can correspond to germline SNPs that are aligned with the individual bins produced at operation 502. For example, a predetermined set of germline SNPs can be selected and aligned with the reference sequence. The genomic location of the germline SNPs can then be compared to the genomic locations of individual bins. In this way, at least a portion of the individual bins produced by the reference genome binning at operation 502 can include one or more germline SNPs. The number of germline SNPs represented in the germline SNP MAF data 516 can at least about 100 SNPs, at least about 250 SNPs, at least about 500 SNPs, at least about 1000 SNPs, at least about 1500 SNPs, at least about 2000 SNPs, at least about 3000 SNPs, at least about 4000 SNPs, or at least about 5000 SNPs. Additionally, the number of germline SNPs represented in the germline SNP MAF data 616 can be no greater than about 30,000 SNPs, no greater than about 25,000 SNPs, no greater than about 20,000 SNPs, no greater than about 15,000 SNPs, no greater than about 10,000 SNPs, or no greater than about 8000 SNPs. In one or more illustrative examples, the number of germline SNPs represented in the germline SNP MAF data 616 can be from about 250 SNPs to about 30,000 SNPs, from about 500 SNPs to about 10,000 SNPs, from about 1000 SNPs to about 5000 SNPs, or from about 2500 SNPs to about 8000 SNPs. In various examples, the SNPs represented in the germline SNP MAF data 516 can correspond to SNPs that are associated with the presence of at least one type of cancer in individuals. In one or more additional examples, the SNPs represented in the germline SNP MAF data 516 can correspond to SNPs that correspond to driver mutations.

In one or more examples, the mutant allele fraction for the individual germline SNPs can be determined and used to determine segments of the reference sequence. The number of segments and the number of nucleotides included in individual segments produced at operation 514 can be the same as or similar to those produced at operation 512. For example, the segmentation using germline SNP MAF data 516 performed at operation 514 can include determining segments of the reference sequence that are different from the bins. In one or more examples, the segmentation using the germline SNP MAF data 516 can partition the reference sequence into at least 30 segments, at least 35 segments, at least 40 segments, at least 45 segments, at least 50 segments, at least 55 segments, or at least 60 segments. In one or more illustrative examples, the segments produced by the segmentation using the germline SNP MAF data 516 can include a greater number of nucleotides than the bins generated as part of the reference genome binning performed at operation 502. For example, individual segments produced at operation 514 can include at least about 2 million nucleotides, at least about 3 million nucleotides, at least about 4 million nucleotides, at least about 5 million nucleotides, at least about 6 million nucleotides, or at least about 7 million nucleotides. In one or more illustrative examples, individual segments produced at operation 514 can include from about 2 million nucleotides to about 12 million nucleotides, from about 3 million nucleotides to about 10 million nucleotides, or from about 4 million nucleotides to about 8 million nucleotides. In various examples, at least one or more of the segments produced at operation 54 can have a different number of nucleotides than at least one additional one of the segments produced at operation 514. That is, the individual segments generated by the operation 514 using the germline SNP data 516 can have a variable number of nucleotides. Additionally, the number of nucleotides included in given segments determined at operation 514 can be different across different samples. To illustrate, a first number of nucleotides included in individual segments produced at operation 514 for a first sample obtained from a first individual can be different from a second number of nucleotides included in individual segments produced at operation 514 for a second sample obtained from a second individual. In one or more implementations, for a given group of samples, the number and location of bins produced at operation 502 can be the same, while at least one of the number of segments or the size of the segments produced at operation 514 can vary.

In various examples, the germline SNP MAF data 516 can be modified or transformed prior to being used at operation 514. For example, the reciprocal of the MAFs for the germline SNPs can be determined. Additionally, a log base 2 transform can be applied to the reciprocals of the germline SNPs to generate modified germline SNP MAF data 516 that is used at operation 514 to produce segments of the reference sequence. In one or more illustrative examples, the SNP MAF data 516 can be adjusted in order to remove effects of alternative allele copy number alteration. In one or more illustrative examples, SNP MAF data 516 is adjusted to be below the allelic balanced baseline. For example, when an MAF value is below the baseline value, it is kept as its original value. In situations where an MAF is above the baseline value, it is flipped down to be (1−MAF)×(baseline/0.5). The adjusted MAFs are then log 2 transformed and shifted up by 1 so that the original allelic balanced MAF of 0.5 is now transformed to be 0.

A number of the segments that are determined by operations 512 and 514 can be at least 5, at least 7, at least 10, at least 12, at least 15, at least 16, at least 17, at least 18, at least 19, at least 20, at least 21, at least 22, at least 23, at least 24, or at least 25. In one or more illustrative examples, the number of segments produced by operations 512 and 514 can be from 5 to 30, from 10 to 27, or from 18 to 24.

In various examples, the germline SNP MAF data 516 can be provided as input to one or more circular binary segmentation processes to determine segments of the reference sequence. Additionally, the segmentation using the germline SNP MAF data 516 performed at operation 514 can be a refinement of the segmentation using the coverage data 508 performed at operation 512. In one or more scenarios, the segmentation using the coverage data 508 performed at operation 512 can be a first implementation of one or more circular binary segmentation processes and the segmentation using the germline SNP MAF data 516 performed at operation 516 can be a second implementation of the one or more circular binary segmentation processes. In one or more examples, the segments generated by operation 514 can be used as input to the operation 516. In one or more examples, the coverage data 508 can correspond to first weights of the circular binary segmentation algorithm that are used during the first implementation of the circular binary segmentation algorithm and the germline SNP MAF data can correspond to second weights of the circular binary segmentation algorithm that correspond to the second implementation of the circular binary segmentation algorithm.

In one or more implementations, the segmentation performed at operation 514 using the germline SNP MAF data 516 can provide a more consistent and more accurate segmentation of the reference sequence than segmentation using only the coverage data 508 performed at operation 514. To illustrate, in at least some situations, an amount of noise can be present in the data after the segmentation using the coverage data 508 at operation 512 that causes an amount of uncertainty in regard to determining the copy number for one or more of the segments determined at operation 512. The segmentation using the germline SNP MAF data 516 at operation 514 can reduce the amount of noise present and result in a more accurate determination of segments of the reference sequence than when only the segmentation at operation 512 takes place.

Segmentation data 518 can be produced by the additional segmentation operations performed at 510. The process 500 can include, at operation 520, generating one or more tumor indicators 522 based on the segmentation data 518. The tumor indicators 522 can include estimates of at least one of tumor cells copy number or tumor fraction. The tumor cells copy number for individual segments included in the segmentation data 518 can indicate an amount of amplification or deletion of a genomic region that corresponds to one or more of the individual segments. In various examples, the tumor cells copy number can indicate a loss of heterozygosity of a genomic region that corresponds to one or more of the individual segments included in the segmentation data 518.

The tumor indicators 522 generated at operation 520 can be determined using a likelihood function 524. The likelihood function can be performed by individually feeding a grid of numerical values into the likelihood function until convergence around the tumor cells copy number for a given segment and tumor fraction for a given sample. The grid of numerical values can include a number of estimates for tumor cells copy number and/or a number of estimates for tumor fraction. In one or more illustrative examples, the likelihood function 524 can include a maximum likelihood estimation model. In various examples, the likelihood function 524 can include tumor indicator components 526. The tumor indicator components 526 can include parameters of the likelihood function 524 that are used to generate the tumor indicators 522.

In one or more additional implementations, the tumor indicators 522 can be determined using the likelihood function 524 directly using the coverage data 508 and the germline SNP MAF data 516. That is, the tumor indicators 522 can be determined without performing the additional segmentation operations at operation 510. In these scenarios, the likelihood function 524 can include segmentation components 528. The segmentation components 528 can include parameters of the likelihood function 524 that can be used to determine segments of the reference sequence. The segmentation components 528 can include parameters that are different from the parameters of the likelihood function that correspond to the tumor indicator components 526. In one or more examples, the coverage data 508 can be normalized prior to being analyzed by the segmentation components 528 of the likelihood function 524.

In one or more examples, the segmentation components 528 can be used to generate at least 5 segments of the reference sequence, at least 7 segments of the reference sequence, at least 10 segments of the reference sequence, at least 12 segments of the reference sequence, at least 15 segments of the reference sequence, at least 16 segments of the reference sequence, at least 17 segments of the reference sequence, at least 18 segments of the reference sequence, at least 19 segments of the reference sequence, at least 20 segments of the reference sequence, at least 21 segments of the reference sequence, at least 22 segments of the reference sequence, at least 23 segments of the reference sequence, at least 24 segments of the reference sequence, or at least 25 segments of the reference sequence. In one or more illustrative examples, the segmentation components 528 of the likelihood function can be used to generate from 5 to 30 segments of the reference sequence, from 10 to 27 segments of the reference sequence, or from 18 to 24 segments of the reference sequence. In one or more additional illustrative examples, individual segments produced using the segmentation components 528 of the likelihood function can include from about 2 million nucleotides to about 12 million nucleotides, from about 3 million nucleotides to about 10 million nucleotides, or from about 4 million nucleotides to about 8 million nucleotides.

In various examples, an initial segmentation can be determined using maximum likelihood estimators of the parameters of the likelihood function 524 that correspond to the tumor indicator components 526. In one or more examples, the parameters can correspond to estimates of tumor cells copy number and tumor fraction of the sample. The tumor cells copy number (CN) can be determined using the formula:

$$CN=n*TF+2*(1-TF)$$, where TF is the sample tumor fraction and $n$ is the tumor cell copy number.

The parameters of the likelihood function can also correspond to the mutant allele frequency (MAF) of the germline SNPs. The MAF of the germline SNPs can be determined using the formula:

$$MAF=(n-1)*TF/(n*TF+2*(1-TF)) \text{ or } MAF=TF/(nTF+2*(1-TF)).$$

In one or more illustrative examples, the tumor indicators 522 can be determined using the likelihood function with both tumor indicator components 526 and segmentation components 528 by providing an initial segmentation estimate and then finding the maximum likelihood estimates for the tumor cells copy numbers of the initial segments and the sample tumor fraction. The initial segmentation can correspond to the 23 chromosomes of a human reference sequence. In one or more additional examples, the initial segmentation can correspond to an initial implementation of a circular binary segmentation algorithm based on the coverage data 508. In one or more further examples, the initial segmentation can correspond to an initial implementation of a circular binary segmentation algorithm based on the coverage data 508 and in initial implementation of one or more circular binary segmentation (CBS) processes with regard to the germline SNPs.

The segmentation performed by the likelihood function 524 using the coverage data 508 and the germline SNP MAF data 516 can be performed using an iterative process. The iterative process can include performing multiple operations for individual segments. For example, for individual segments a circular partition can be performed. The circular partition can represent a splitting of the segment into multiple sub-segments. To illustrate, the segment can be split into 3 sub-segments. In situations where the segment is divided into three sub-segments, two marginal sub-segments can correspond to a same copy number and a middle sub-segment can have a different copy number. The circular partition can then be tested to determine whether the circular partition generates a better fit for the coverage data 508 from the bins and the germline SNPs that overlap the segment using the segment copy number and the sample tumor fraction. The fit for the circular partition can be determined using one or more statistical or machine learning techniques. To illustrate, an F-statistic can be determined that represents a ratio between variability of means determined based on coverage data of bins for the given segment and heterozygous SNP MAFs. A better fit for the segment data can be determined when the ratio between variability of between the means generated from the bin coverage data and heterozygous SNP MAFs is larger than the variability of the coverage data and SNP MAFs within the segments. In various examples, when the p-value of the F-statistic is below a threshold value, the segments of the circular partition are a better fit and used in the next iteration of the segmentation process. In one or more illustrative examples, the threshold value of the F-statistic can be less than 0.005, 0.008, 0.010, 0.015, or 0.020.

Figure 6:
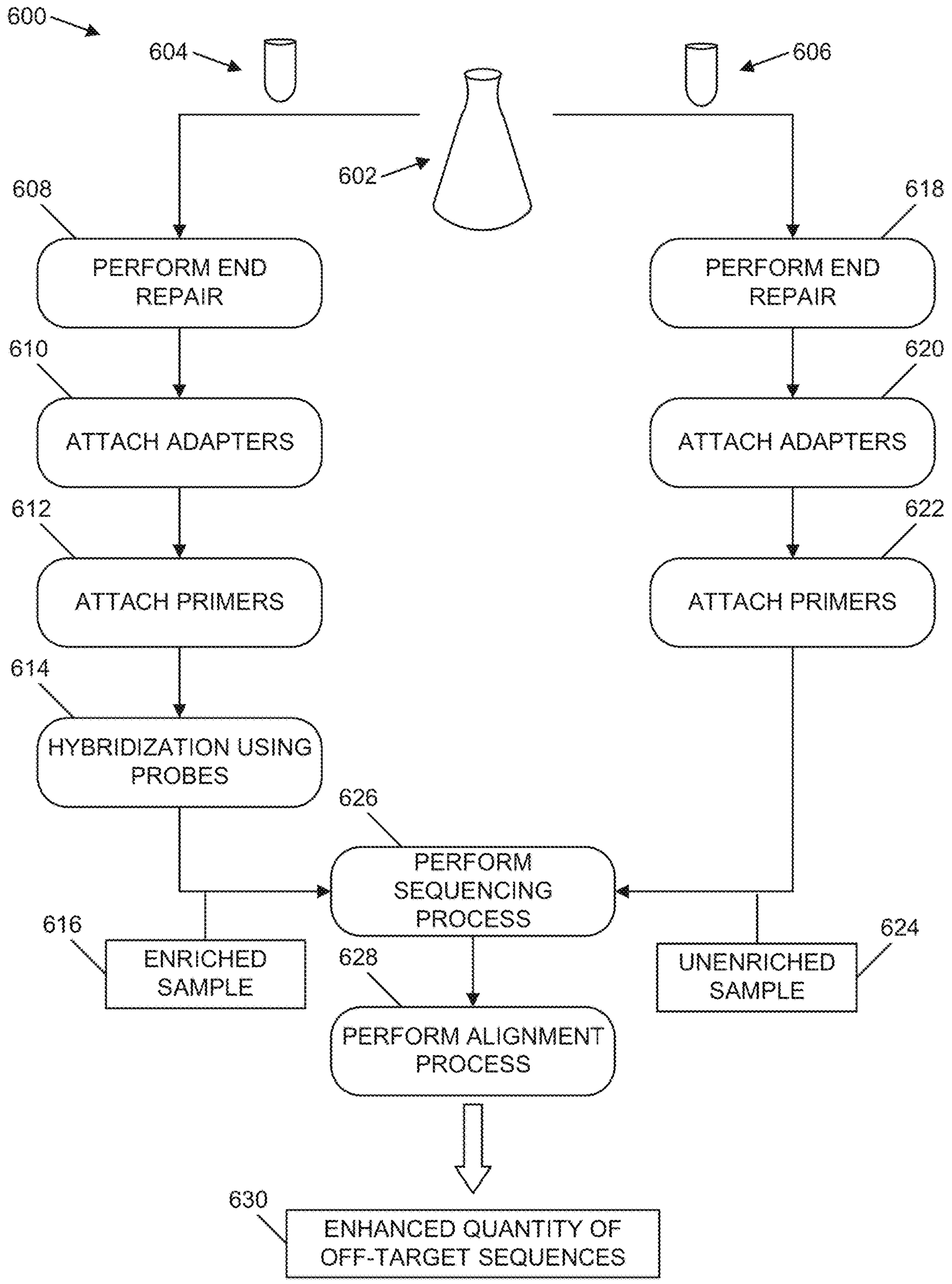
FIG. 6 is a flowchart of an example process to generate an enhanced quantity of off-target polynucleotides that may be used to determine indicators of a tumor being present in a subject, according to one or more implementations.

FIG. 6 is a flowchart of an example process 600 to generate an enhanced quantity of off-target sequence representations that may be used to determine tumor metrics for a subject, according to one or more implementations. The process 600 can be performed with respect to a sample 602.

A first aliquot 604 of the sample 602 and a second aliquot 606 of the sample 602 can be obtained. The first aliquot 604 can undergo a first number of operations, such as performing end repair at 608, attaching adapters comprising molecular barcodes at 610, attaching primers at 612, and enriching for target regions by hybridizing the fragments to probes using probes at 614. Prior to the hybridization using probes at operation 614, one or more amplification operations can take place to amplify at least a portion of the polynucleotides that have been subjected to operations 608, 610, and 612. Operations 608, 610, 612, 614 can be performed with respect to the first aliquot 604 resulting in an enriched sample 616. The enriched sample 616 can include a number of cell-free nucleic acids that have been labeled using bar codes that can be used to identify sequences that correspond to individual nucleic acids included in the first aliquot 604. Additionally, the enriched sample 616 can include double stranded nucleic acids where nucleic acids included in the first aliquot 604 that have at least a threshold amount of complementarity with respect to a probe have combined to form the double stranded nucleic acids.

The second aliquot 606 can undergo a second number of operations that are different from the first number of operations performed with respect to the first aliquot 604. For example, the second aliquot 606 can undergo an end repair operation at 618, an adapters (comprising molecular barcodes) attachment operation at 620, and a primers attachment operation at 622 to generate an unenriched sample 624. The unenriched sample 624 can include single stranded nucleic acids of the second aliquot 606 that have not been subjected to a hybridization process.

The enriched sample 616 and the unenriched sample 624 can be combined during a sequencing process that is performed at 626. In one or more illustrative examples, the nucleic acids included in the enriched sample 616 and the nucleic acids included in the unenriched sample 624 that have not been hybridized may not be amplified during the sequencing process. At least about 90% of the nucleic acids included in the second aliquot 606 may not be amplified during the sequencing process, at least about 95% of the nucleic acids included in the second aliquot 606 may not be amplified during the sequencing process, at least about 97% of the nucleic acids included in the second aliquot 606 may not be amplified during the sequencing process, at least about 98% of the nucleic acids included in the second aliquot 606 may not be amplified during the sequencing process, or at least about 99% of the nucleic acids included in the second aliquot 606 may not be amplified during the sequencing process.

A sequencing product can be produced as a result of the sequencing process. In various examples, the sequencing product can include an amplification product that includes nucleic acids that correspond to hybridized nucleic acids that have been amplified during the sequencing process. The sequencing product can also include nucleic acids that have not been amplified during the sequencing process, such as nucleic acids included in the first aliquot 604 that do not correspond to target regions of a reference sequence that are related to the probes used during hybridization. The sequencing product can also include nucleic acids included in the second aliquot 606.

At operation 628, the process 600 can include performing an alignment process that aligns sequences of the polynucleotide sequence produced by the sequencing process with a reference sequence. The alignment process can identify off-target sequence representations that correspond to sequence representations related to nucleic acids included in the sequencing product that do not correspond to a target region of a reference sequence. The off-target sequence representations can be derived from nucleic acids included in the enriched sample 616 and nucleic acids included in the unenriched sample 624 that do not correspond to a target region of a reference sequence. An enhanced quantity of off-target sequence representations 630 can be generated based on the alignment process because the enhanced quantity of off-target sequence representations 630 comprises off-target sequence representations derived from both the enriched sample 616 and the unenriched sample 624 rather than identifying off-target sequence representations derived from a single source, such as the enriched sample 616.

Figure 7:
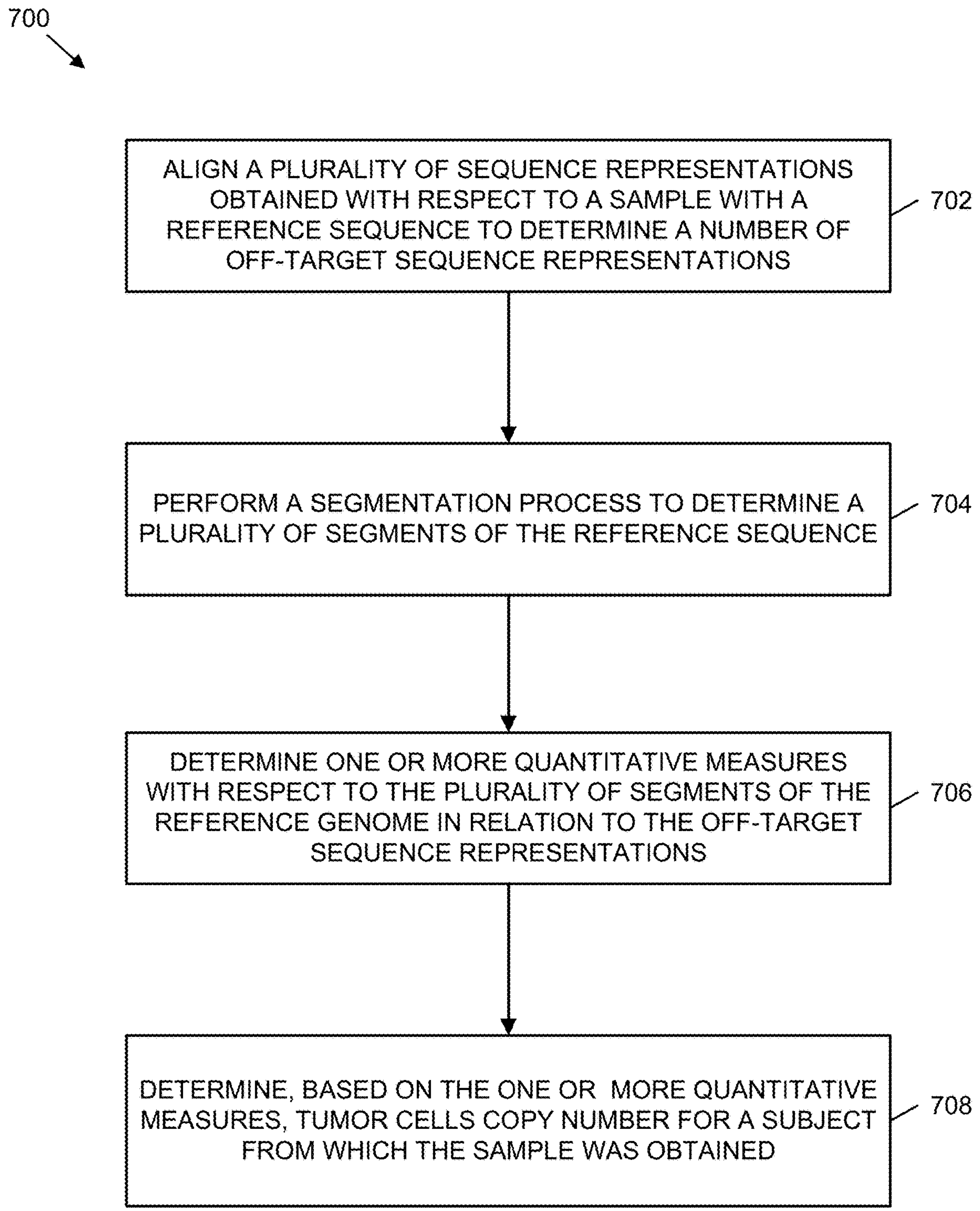
FIG. 7 is a flowchart of an example method to determine tumor metrics with respect to a subject based on information derived from off-target polynucleotides that include at least one segmentation process with respect to a reference human genome, according to one or more implementations.

FIG. 7 is a flowchart of an example method 700 to determine tumor metrics in a subject based on information derived from off-target sequence representations, according to one or more implementations. At operation 702, the method 700 can include aligning a plurality of sequences obtained from a sample with a reference sequence to determine a number of off-target sequence representations. The off-target sequence representations can be aligned with regions of the reference genome that are outside of target regions of the reference genome that correspond to driver mutations. In various examples, the sample can comprise cell-free DNA molecules.

In addition, at operation 704, a segmentation process can be performed to determine a plurality of segments of the reference sequence. The segmentation process can include dividing the reference genome into a number of segments based on one or more criteria. In one or more examples, multiple segmentation operations can be performed. In these scenarios, different criteria can be applied with respect to different segmentation operations. For example, one or more first segmentation operations can be implemented in accordance with one or more first criteria and a second segmentation process can be implemented in accordance with one or more second criteria. To illustrate, a first segmentation process can be implemented by dividing the reference sequence into segments having a specified size, such as at least 50 kb, at least 75 kb, at least 100 kb, at least 125 kb, or at least 150 kb. In various examples, at least a portion of the segments can have a same number of nucleotides. Additionally, a second segmentation process can be performed that determines second segments of the reference genome based on the tumor cells copy number of the respective segments being unchanged. In various examples, the second segments can have a larger size than the first segments and include a number of the first segments.

Further, at operation 706, the method 700 can include determining one or more quantitative measures with respect to the plurality of segments of the reference sequence in relation to the off-target sequence representations, such as coverage metrics and size distribution metrics. The coverage metrics can indicate a count of sequence representations corresponding to one or more segments of the reference sequence. The size distribution metrics can indicate a count of off-target sequence representations having respective sizes in relation to the size distribution. In one or more examples, the size distribution can include a number of partitions that each correspond to a range of sizes of sequence representations. In one or more examples, normalized quantitative measures can also be determined based on the one or more quantitative measures. In various examples, the normalized quantitative measures can be determined based on reference quantitative measures derived from reference samples obtained from individuals in which copy number variation is not present. In one or more further examples, the normalized quantitative measures can be determined based on at least one of mappability scores of the first segments or guanine-cytosine (G-C) content of the first segments. In one or more additional examples, the one or more quantitative measures can correspond to quantitative measures of single nucleotide polymorphisms (SNPs) that correspond to target regions of the reference sequence.

The method 700 can also include determining, based on the one or more quantitative measures, tumor cells copy number for a subject from which the sample was obtained. In one or more examples, the tumor cells copy number can be determined based on at least one of coverage metrics of off-target sequence representations or size distribution metrics of off-target sequence representations. In various examples, the tumor cells copy number can also be determined based on quantitative measures derived from sequence representations related to target regions of the reference sequence. Further, the tumor cells copy number can be determined based on maximum allele fraction of germline SNPs that correspond to target regions of the reference sequence. The tumor cells copy number can also be determined according to a combination of at least two of coverage metrics of off-target sequence representations, size distribution metrics of off-target sequence representations, quantitative measures derived from sequence representations related to target regions of the reference sequence, or maximum allele fraction of germline SNPs that correspond to target regions of the reference sequence.

Figure 8:
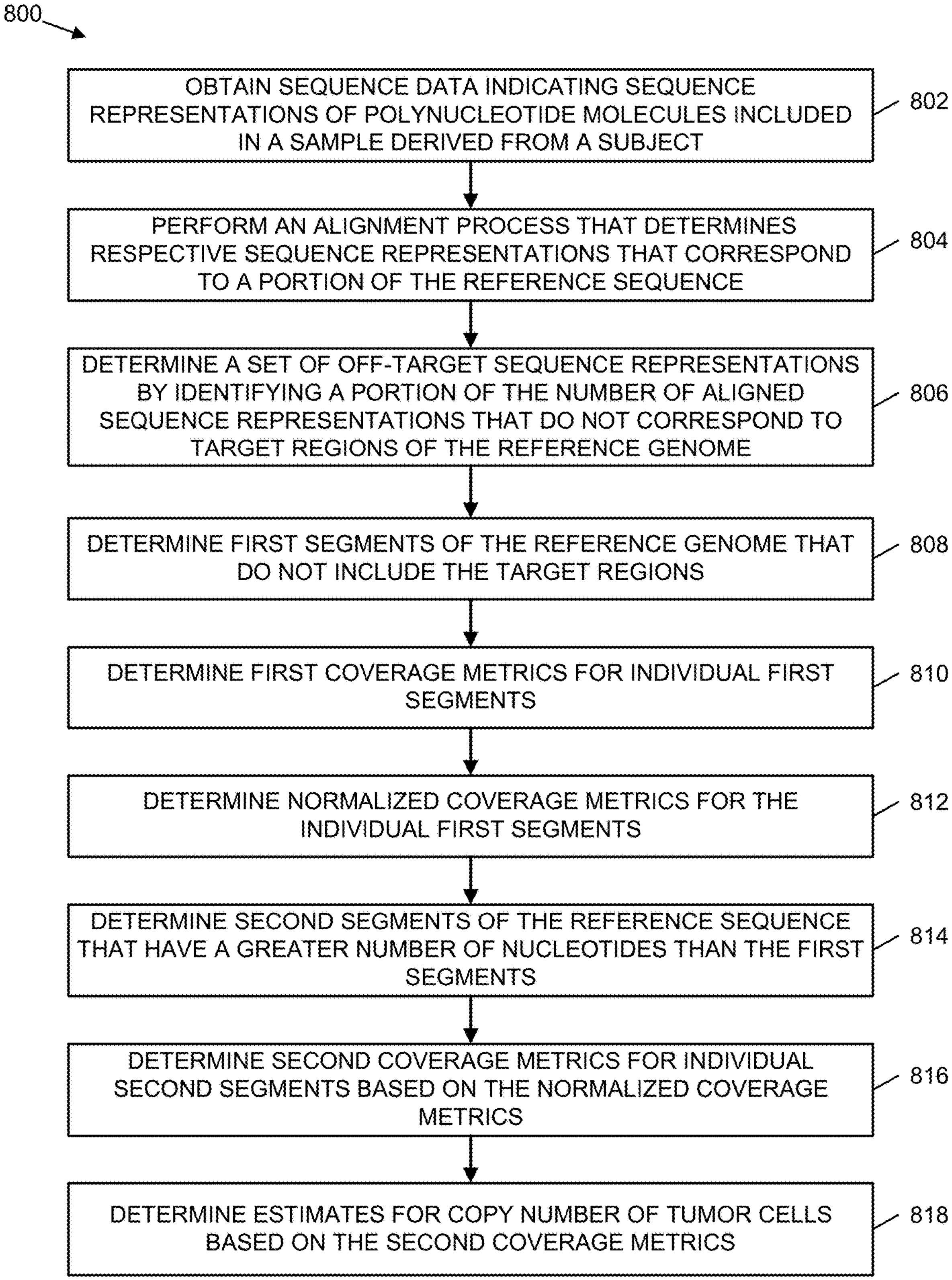
FIG. 8 is a flowchart of an example method to determine tumor metrics with respect to a subject based on coverage information derived from off-target polynucleotides that includes multiple segmentations processes with respect to a reference human genome, according to one or more implementations.

FIG. 8 is a flowchart of an example method 800 to determine tumor metrics with respect to a subject based on coverage information derived from off-target polynucleotides, according to one or more implementations. The method 800 can include, at operation 802, obtaining sequencing data indicating sequence representations of polynucleotide molecules included in a sample derived from a subject. The subject can be a human subject. The sequence representations can correspond to sequencing reads that are generating as part of a sequencing process related to the sample. In various examples, the sample can comprise cell-free DNA molecules.

In addition, at operation 804, the method 800 can include performing an alignment process that determines respective sequence representations that correspond to a portion of a reference sequence. The alignment process can determine sequence representations that correspond to a respective portion of the reference sequence. In one or more examples, the alignment process can be performed without filtering the sequencing reads or grouping the sequencing reads according to an initial polynucleotide included in the sample. In one or more additional examples, the sequencing reads can be filtered by determining multiple sequencing reads that correspond to individual polynucleotide molecules included in the sample. In these scenarios, the alignment process would be performed using a single sequence representation that corresponds to the individual polynucleotide molecules included in the sample. Further, at operation 806, the method 800 can include determining a set of off-target sequence representations by identifying a portion of the number of aligned sequence representations that do not correspond to target regions of the reference sequence.

The method 800 can also include, at operation 808, determining first segments of the reference sequence that do not include the target regions. The first segments can be determined as part of a first segmentation process that divides the reference genome into the number of first segments according to one or more criteria. In various examples, the one or more criteria can include a maximum size for the individual first segments. In one or more additional examples, the one or more criteria can include maximizing a number of the first segments having a respective size, such as 50 kb, 75 kb, 100 kb, 125 kb, or 150 kb.

At operation 810, the process 800 can include determining first coverage metrics for individual first segments. The first coverage metrics can indicate a number of sequence representations that correspond to individual first segments. In one or more illustrative examples, the first coverage metrics can be determined by counting the sequence representations that align with portions of the reference sequence that correspond to the individual first segments.

Additionally, at operation 812, the method 800 can include determining normalized coverage metrics for the individual first segments. The normalized coverage metrics can be determined based on reference coverage metrics. In one or more examples, the reference coverage metrics can be determined based on coverage information derived from reference samples obtained from individuals in which copy number variation is not present. In various examples, the reference coverage metrics can be determined by determining a number of sequence representations derived from the reference samples that align with individual first segments of the reference sequence. The normalized coverage metrics can be determined by determining a ratio of the number of sequence representations derived from the sample that are aligned with individual first segments in relation to the number of sequence representations derived from the reference samples that are aligned with the individual first segments. The normalized coverage metrics can also be determined by determining a ratio of the number of sequence representations derived from the sample that are aligned with individual first segments in relation to an average number of sequence representations for the first segments.

In one or more additional examples, the normalized coverage metrics can be determined based on guanine-cytosine (G-C) content of the first segments. To illustrate, the normalized coverage metrics can be determined by determining a frequency of G-C residues aligned with the individual first segments. The frequency of G-C residues aligned with the individual first segments can then be analyzed with respect to an expected number of G-C residues for the individual first segments to determine normalized G-C coverage metrics for the individual first segments.

In still further examples, the normalized coverage metrics can be determined based on mappability scores for the first segments. For example, the normalized coverage metrics can be determined by determining an amount of homology between portions of individual first segments with respect to additional portions of additional individual first segments. To illustrate, a portion of a first segment can be analyzed with respect to additional portions of the reference sequence to determine an amount of homology between the portion of the first segment and the additional portions of the reference sequence to generate mappability scores for the portion of the first segment. The mappability scores for portions of individual first segments can be analyzed with respect to expected mappability scores for the individual first segments to determine the normalized coverage metrics.

Further, at operation 814, the process 800 can include determining second segments of the reference human genome that have a greater number of nucleotides than the first segments. The second segments can be determined based on a second segmentation process that is different from the first segmentation process used to determine the first segments. In one or more examples, the second segmentation process can determine the second segments based on different criteria from the criteria used to determine the first segments. In various examples, the second segments can include a greater number of nucleotides than the first segments and the second segments can include a number of the first segments. In addition, the second segments can include on-target regions. In one or more illustrative examples, one or more criteria used to determine the second segments can include determining that a tumor cells copy number with respect to a second segment is not changing.

At operation 816, the method 800 can include determining second coverage metrics for individual second segments based on the normalized coverage metrics. The second coverage metrics for individual second segments can include the normalized coverage metrics for the individual bins included in the respective second segments. The method 800 can include, at operation 818, determining estimates for the copy number of tumor cells based on the second coverage metrics. In one or more examples, the estimates for the tumor cells copy number can be parameters for a maximum likelihood estimation model. The copy number of the tumor cells can be used to determine the effectiveness of one or more interventions provided to the subject that provided the sample. The one or more interventions can be provided to the subject to treat a disease or biological condition of the subject. In one or more illustrative examples, the disease or biological condition can include cancer. In addition, the copy number of tumor cells can be used to determine a prognosis for the subject with respect to a disease or condition. In one or more additional examples, the second coverage metrics can also be used to determine a tumor fraction with respect to the subject.

Figure 9:
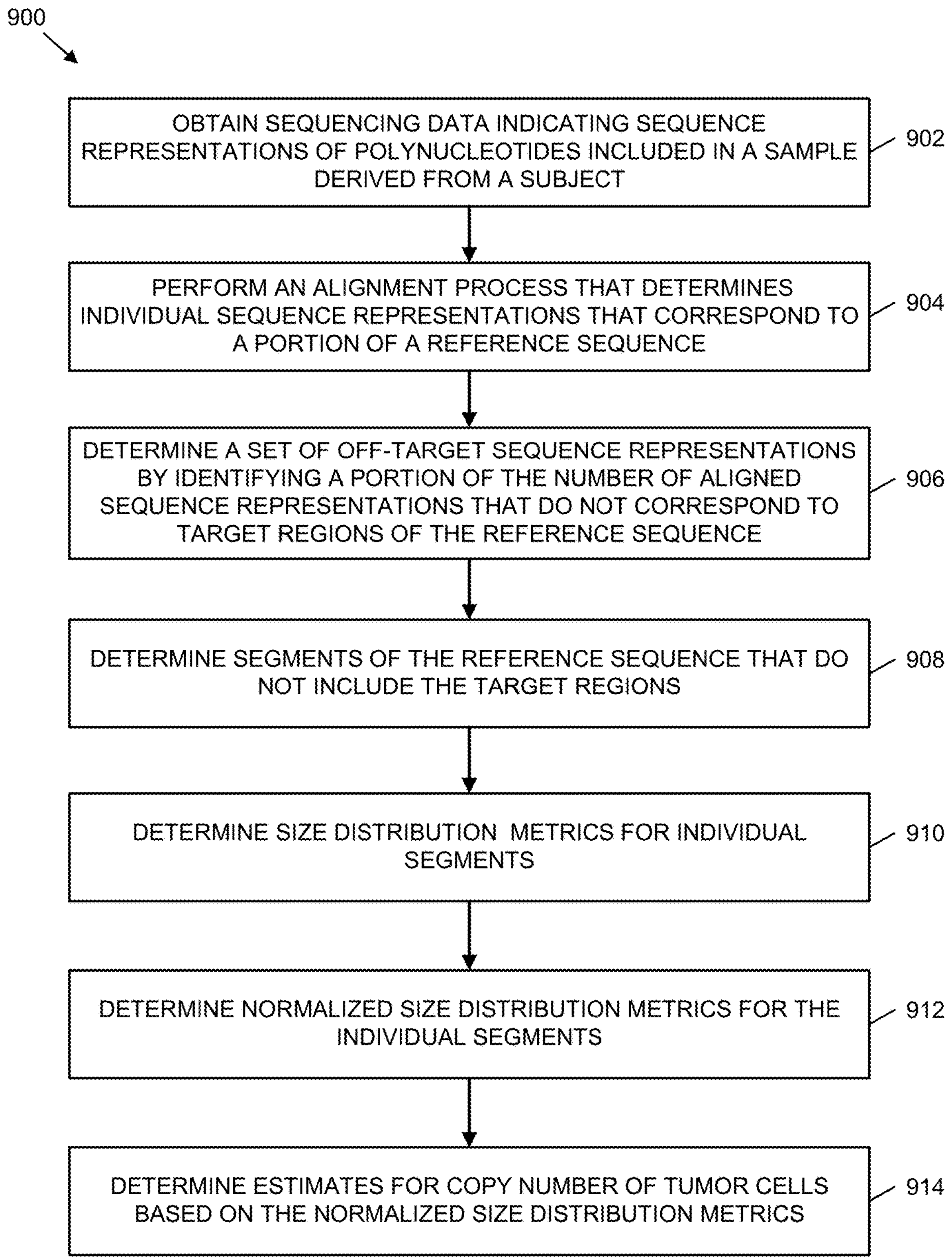
FIG. 9 is a flowchart of an example method to determined tumor metrics with respect to a subject based on size distribution information derived from off-target polynucleotides, according to one or more implementations.

FIG. 9 is a flowchart of an example method 900 to determine tumor metrics with respect to a subject based on size distribution information derived from off-target polynucleotides, according to one or more implementations. The method 900 can include, at operation 902 obtaining sequencing data indicating sequence representations of polynucleotides included in a sample derived from a subject. In one or more examples, the subject can be a human subject. The sequence representations can correspond to sequencing reads included in the sequencing data. In various examples, the sample can comprise cell-free DNA molecules.

At operation 904, the method 900 can include performing an alignment process that determines one or more portions of a reference sequence that correspond to individual sequence representations. The alignment process can determine sequence representations that correspond to a respective portion of the reference sequence. In one or more examples, the alignment process can be performed without filtering the sequencing reads or grouping the sequencing reads according to an initial polynucleotide included in the sample. In one or more additional examples, the sequencing reads can be filtered by determining multiple sequencing reads that correspond to individual polynucleotide molecules included in the sample. In these scenarios, the alignment process would be performed using a single sequence representation that corresponds to the individual polynucleotide molecules included in the sample.

In addition, the method 900 can include, at operation 906, determining a set of off-target molecules by identifying a portion of the number of aligned sequences that do not correspond to target regions of the reference sequence. Further, the method 900 can include, at operation 908, determining segments of the reference sequence that do not include the target regions. The segments can be determined as part of a segmentation process that divides the reference genome into the number of segments according to one or more criteria. In various examples, the one or more criteria can include a maximum size for the individual segments. In one or more additional examples, the one or more criteria can include maximizing a number of the segments having a respective size, such as 50 kb, 75 kb, 100 kb, 125 kb, or 150 kb.

The method 900 can also include, at operation 910, determining sequence size distribution metrics for individual segments. The sequence size distribution metrics can correspond to a number of sequence representations that correspond to various ranges of sizes of sequence representations. For example, size distributions can be determined for individual segments. The size distributions can include a number of partitions with each partition corresponding to a range of sizes of sequence representations. In one or more illustrative examples, a first partition of a size distribution can correspond to sequence representations having from 1 nucleotide to 40 nucleotides, a second partition can correspond to sequence representations having from 41 nucleotides to 80 nucleotides, a third partition can correspond to sequence representations having from 81 nucleotides to 120 nucleotides, and a fourth partition can correspond to sequence representations having greater than 121 nucleotides. Continuing with this example, the sequence size distribution metrics for one or more segments can indicate a first number of sequence representations that correspond to the first partition, a second number of sequence representations that correspond to the second partition, a third number of sequence representations that correspond to the third partition, and a fourth number of sequence representations that correspond to the fourth partition. In various examples, the range of sizes of sequence representations corresponding to each partition can be based on a mean size of sequence representations for the individual segments and standard deviations from the mean.

The method 900 can also include, at operation 912, determining normalized sequence size distribution metrics for the individual segments. The normalized sequence size distribution metrics for the individual segments can be determined based on reference size distribution metrics. In one or more examples, the reference size distribution metrics can be determined based on sequence size distribution information derived from reference samples obtained from individuals in which copy number variation is not present. In various examples, the reference size distribution metrics can be determined by determining a number of sequence representations derived from the reference samples that align with individual segments of the reference sequence and that correspond to an individual partition of a size distribution. The normalized size distribution metrics can be determined by determining a ratio of the number of sequence representations derived from the sample that are aligned with individual segments and that correspond to a respective partition of a size distribution in relation to the number of sequence representations derived from the reference samples that are aligned with the individual segments and that correspond to the respective partition of the size distribution. The normalized size distribution metrics can also be determined by determining a ratio of the number of sequence representations derived from the sample that are aligned with individual segments and that correspond to a respective partition of the size distribution in relation to an average number of sequence representations for the segments that correspond to the respective partition of the size distribution.

Further, at operation 914, the method 900 can include determining estimates for a copy number of tumor cells based on the normalized sequence size distribution metrics. In one or more examples, the estimates for the tumor cells copy number can be parameters for a maximum likelihood estimation model. The copy number of the tumor cells can be used to determine the effectiveness of one or more interventions provided to the subject that provided the sample. The one or more interventions can be provided to the subject to treat a disease or biological condition of the subject. In one or more illustrative examples, the disease or biological condition can include cancer. In addition, the copy number of tumor cells can be used to determine a prognosis for the subject with respect to a disease or condition. In one or more additional examples, the normalized size distribution metrics can also be used to determine a tumor fraction with respect to the subject.

Although not described with respect to FIG. 9, the process 900 can also include a second segmentation process that is used to determine second size distribution metrics based on the normalized size distribution metrics. The second size distribution metrics can be used to determine the estimates for the copy number of tumor cells. In one or more examples, the second segmentation process can determine the second segments based on different criteria from the criteria used to determine the first segments. In various examples, the second segments can include a greater number of nucleotides than the first segments and the second segments can include a number of the first segments. In addition, the second segments can include on-target regions. In one or more illustrative examples, one or more criteria used to determine the second segments can include determining that a tumor cells copy number with respect to a second segment is not changing.

Figure 10:
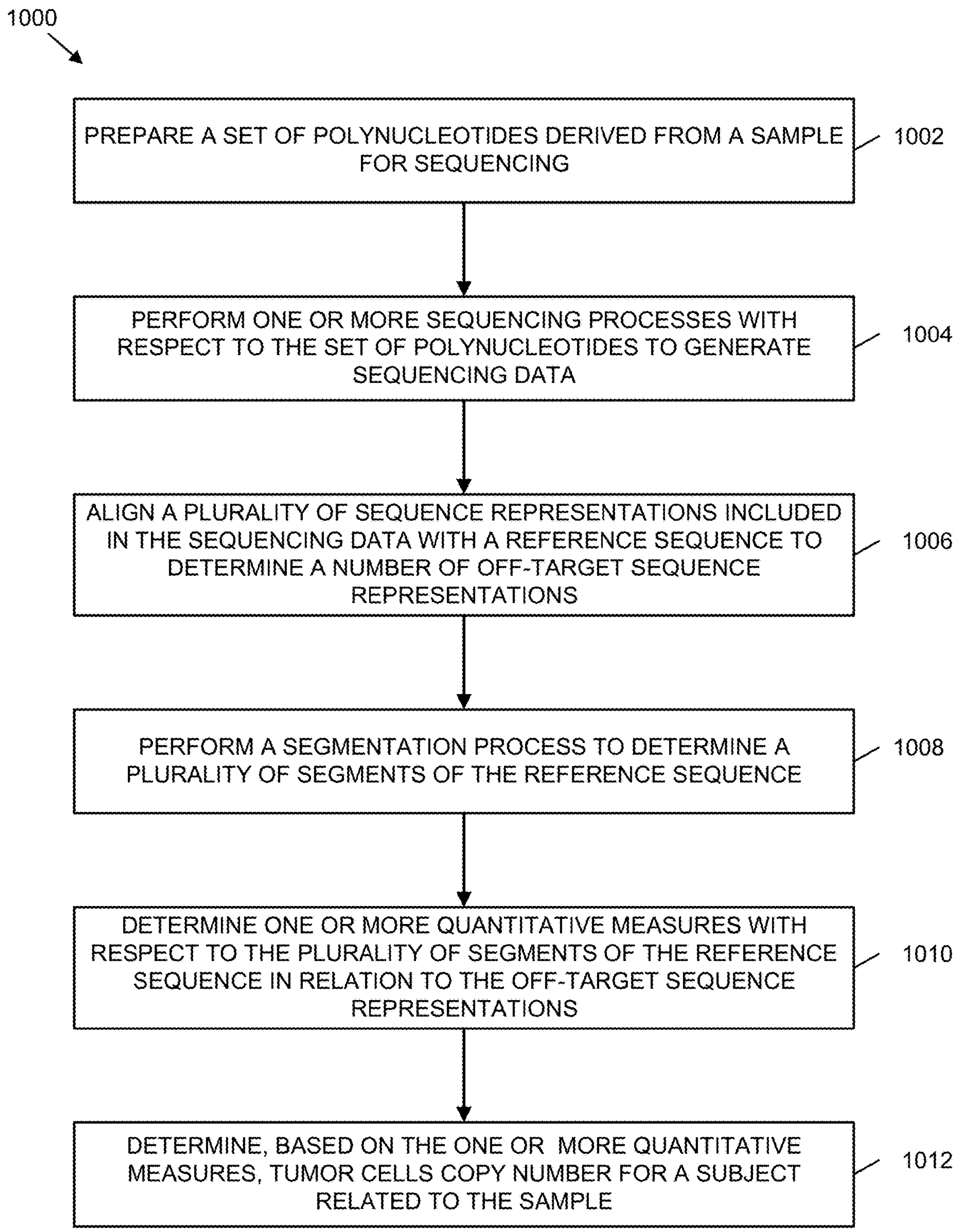
FIG. 10 is a flowchart of an example method to generate sequencing data and determine off-target sequence representations from the sequencing data where the off-target sequence representations can be used to determined tumor metrics with respect to a subject based on information derived from the off-target sequence representations, according to one or more implementations.

FIG. 10 is a flowchart of an example method to generate sequencing data and determine off-target sequence representations from the sequencing data where the off-target sequence representations can be used to determined tumor metrics with respect to a subject based on information derived from the off-target sequence representations, according to one or more implementations. The method 1000 can include, at 1002, preparing a set of polynucleotides derived from a sample for sequencing. For example, blunt-end ligation can be performed on the set of polynucleotides and molecular barcodes can be added to the individual polynucleotides included in the set of polynucleotides. The molecular barcodes can be used to identify the individual polynucleotides. Further, the set of polynucleotides can be enriched by performing one or more hybridization processes between the set of polynucleotides and probes that correspond to target regions of a reference sequence to generate an enriched set of polynucleotides. In one or more examples, the enriched set of polynucleotides can be amplified prior to sequencing. In one or more additional examples, at least a portion of the set of polynucleotides that do not hybridize with the probes can also be amplified prior to sequencing. Polynucleotides that do not hybridize with the probes can be referred to herein as "non-hybridized polynucleotides." In various examples, the sample can comprise cell-free DNA molecules.

In addition, at 1004, the method 1000 can include performing one or more sequencing processes with respect to the set of polynucleotide molecules to generate sequencing data. The sequencing data can include a number of sequencing reads, also referred to herein as sequence representations, that correspond to the hybridized and non-hybridized polynucleotides. The sequencing reads can correspond to data that indicates alphanumeric sequences related to the polynucleotides that have been sequenced. In one or more illustrative examples, the sequencing data can include gigabytes, up to terabytes of data.

The method 1000 can also include, at 1006, aligning a plurality of sequence representations included in the sequence data with a reference sequence to determine a number of off-target sequence representations. The off-target sequence representations can be aligned with regions of the reference genome that are outside of target regions of the reference genome that correspond to driver mutations.

Additionally, at 1008, the method 1000 can include performing a segmentation process to determine a plurality of segments of the reference sequence. The segmentation process can include dividing the reference genome into a number of segments based on one or more criteria. In one or more examples, multiple segmentation operations can be performed. In these scenarios, different criteria can be applied with respect to different segmentation operations. For example, first segmentation operations can be implemented with respect to one or more first criteria and a second segmentation process can be implemented with respect to one or more second criteria. To illustrate, a first segmentation process can be implemented by dividing the reference sequence into bins having a specified size, such as at least 50 kb, at least 75 kb, at least 100 kb, at least 125 kb, or at least 150 kb. In various examples, at least a portion of the segments can have a same number of nucleotides. Additionally, a second segmentation process can be performed that determines second segments of the reference genome based on the tumor cells copy number of the respective segments being unchanged. In one or more examples, the second segments can have a larger size than the first segments. To illustrate, the second segments can include a number of the first segments.

At operation 1010, the method 1000 can include determining one or more quantitative measures with respect to the plurality of segments. The quantitative measures can include coverage metrics and size distribution metrics. The coverage metrics can indicate a count of sequence representations corresponding to one or more segments of the reference sequence. The size distribution metrics can indicate a count of off-target sequence representations having respective sizes in relation to the size distribution. In one or more examples, the size distribution can include a number of partitions that each correspond to a range of sizes of sequence representations. In one or more examples, normalized quantitative measures can also be determined based on the one or more quantitative measures. In various examples, the normalized quantitative metrics can be determined based on reference quantitative measures derived from reference samples obtained from individuals in which copy number variation is not present. The normalized quantitative measures can also be determined according to at least one of G-C content of the first segments or mappability scores of the first segments. In one or more additional examples, the one or more quantitative measures can correspond to quantitative measures of single nucleotide polymorphisms (SNPs) that correspond to target regions of the reference sequence.

Further, at 1012, the method 1000 can include determining, based on the one or more quantitative measures, tumor cells copy number for a subject from which the sample was obtained. In one or more examples, the tumor cells copy number can be determined based on at least one of coverage metrics of off-target sequence representations or size distribution metrics of off-target sequence representations. In various examples, the tumor cells copy number can also be determined based on quantitative measures derived from sequence representations related to target regions of the reference sequence. Further, the tumor cells copy number can be determined based on maximum allele fraction of germline SNPs that correspond to target regions of the reference sequence. The tumor cells copy number can also be determined according to a combination of at least two of coverage metrics of off-target sequence representations, size distribution metrics of off-target sequence representations, quantitative measures derived from sequence representations related to target regions of the reference sequence, or maximum allele fraction of germline SNPs that correspond to target regions of the reference sequence.

Samples

Isolation and extraction of cell free polynucleotides may be performed through collection of samples using a variety of techniques. A sample can be any biological sample isolated from a subject. Samples can include body tissues, whole blood, platelets, serum, plasma, stool, red blood cells, white blood cells or leucocytes, endothelial cells, tissue biopsies (e.g., biopsies from known or suspected solid tumors), cerebrospinal fluid, synovial fluid, lymphatic fluid, ascites fluid, interstitial or extracellular fluid (e.g., fluid from intercellular spaces), gingival fluid, crevicular fluid, bone marrow, pleural effusions, cerebrospinal fluid, saliva, mucous, sputum, semen, sweat, urine. Samples are preferably body fluids, particularly blood and fractions thereof, and urine. Such samples include nucleic acids shed from tumors. The nucleic acids can include DNA and RNA and can be in double and single-stranded forms. A sample can be in the form originally isolated from a subject or can have been subjected to further processing to remove or add components, such as cells, enrich for one component relative to another, or convert one form of nucleic acid to another, such as RNA to DNA or single-stranded nucleic acids to double-stranded. Thus, for example, a body fluid sample for analysis is plasma or serum containing cell-free nucleic acids, e.g., cell-free DNA (cfDNA).

In some implementations, the sample volume of body fluid taken from a subject depends on the desired read depth for sequenced regions. Example volumes are about 0.4-40 ml, about 5-20 ml, about 10-20 ml. For example, the volume can be about 0.5 ml, about 1 ml, about 5 ml, about 10 ml, about 20 ml, about 30 ml, about 40 ml, or more milliliters. A volume of sampled blood can be between about 5 ml to about 20 ml.

The sample can comprise various amounts of nucleic acid. The amount of nucleic acid in a given sample can be equated with multiple genome equivalents. For example, a sample of about 30 ng DNA can contain about 10,000 ($10^4$) haploid human genome equivalents and, in the case of cfDNA, about 200 billion ($2\times10^{11}$) individual polynucleotide molecules. Similarly, a sample of about 100 ng of DNA can contain about 30,000 haploid human genome equivalents and, in the case of cfDNA, about 600 billion individual molecules.

In some implementations, a sample comprises nucleic acids from different sources, e.g., from cells and from cell-free sources (e.g., blood samples, etc.). Typically, a sample includes nucleic acids carrying mutations. For example, a sample optionally comprises DNA carrying germline mutations and/or somatic mutations. Typically, a sample comprises DNA carrying cancer-associated mutations (e.g., cancer-associated somatic mutations). In some implementations of the present disclosure, cell free nucleic acids in a subject may derive from a tumor. For example, cell-free DNA isolated from a subject can comprise ctDNA.

Example amounts of cell-free nucleic acids in a sample before amplification typically range from about 1 femtogram (fg) to about 1 microgram (μg), e.g., about 1 picogram (pg) to about 200 nanogram (ng), about 1 ng to about 100 ng, about 10 ng to about 1000 ng. In some implementations, a sample includes up to about 600 ng, up to about 500 ng, up to about 400 ng, up to about 300 ng, up to about 200 ng, up to about 100 ng, up to about 50 ng, or up to about 20 ng of cell-free nucleic acid molecules. Optionally, the amount is at least about 1 fg, at least about 10 fg, at least about 100 fg, at least about 1 pg, at least about 10 pg, at least about 100 pg, at least about 1 ng, at least about 10 ng, at least about 100 ng, at least about 150 ng, or at least about 200 ng of cell-free nucleic acid molecules. In certain implementations, the amount is up to about 1 fg, about 10 fg, about 100 fg, about 1 pg, about 10 pg, about 100 pg, about 1 ng, about 10 ng, about 100 ng, about 150 ng, or about 200 ng of cell-free nucleic acid molecules. In some implementations, methods include obtaining between about 1 fg to about 200 ng cell-free nucleic acid molecules from samples.

Cell-free nucleic acids typically have a size distribution of between about 100 nucleotides in length and about 500 nucleotides in length, with molecules of about 110 nucleotides in length to about 230 nucleotides in length representing about 90% of molecules in the sample, with a mode of about 168 nucleotides length and a second minor peak in a range between about 240 to about 440 nucleotides in length. In certain implementations, cell-free nucleic acids are from about 160 to about 180 nucleotides in length, or from about 320 to about 360 nucleotides in length, or from about 440 to about 480 nucleotides in length.

In some implementations, cell-free nucleic acids are isolated from bodily fluids through a partitioning step in which cell-free nucleic acids, as found in solution, are separated from intact cells and other non-soluble components of the bodily fluid. In some of these implementations, partitioning includes techniques such as centrifugation or filtration. Alternatively, cells in bodily fluids are lysed, and cell-free and cellular nucleic acids processed together. Generally, after addition of buffers and wash steps, cell-free nucleic acids are precipitated with, for example, an alcohol. In certain implementations, additional clean up steps are used, such as silica-based columns to remove contaminants or salts. Non-specific bulk carrier nucleic acids, for example, are optionally added throughout the reaction to optimize certain aspects of the example procedure, such as yield. After such processing, samples typically include various forms of nucleic acids including double-stranded DNA, single-stranded DNA and/or single-stranded RNA. Optionally, single stranded DNA and/or single stranded RNA are converted to double stranded forms so that they are included in subsequent processing and analysis steps. Additional details regarding cfDNA partitioning and related analysis of epigenetic modifications that are optionally adapted for use in performing the methods disclosed herein are described in, for example, WO 2018/119452, filed Dec. 22, 2017, which is incorporated by reference.

Nucleic Acid Tags

In certain implementations, tags providing molecular identifiers or barcodes are incorporated into or otherwise joined to adapters by chemical synthesis, ligation, or overlap extension PCR, among other methods. In some implementations, the assignment of unique or non-unique identifiers, or molecular barcodes in reactions follows methods and utilizes systems described in, for example, US patent applications 20010053519, 20030152490, 20110160078, and U.S. Pat. Nos. 6,582,908, 7,537,898, and 9,598,731, which are each incorporated by reference.

Tags are linked (e.g., ligated) to sample nucleic acids randomly or non-randomly. In some implementations, tags are introduced at an expected ratio of identifiers (e.g., a combination of unique and/or non-unique barcodes) to microwells. For example, the identifiers may be loaded so that more than about 1, 2, 3, 4, 5, 6, 7, 8, 9, 10, 20, 50, 100, 500, 1000, 5000, 10000, 50,000, 100,000, 500,000, 1,000, 000, 10,000,000, 50,000,000 or 1,000,000,000 identifiers are loaded per genome sample. In some implementations, the identifiers are loaded so that less than about 2, 3, 4, 5, 6, 7, 8, 9, 10, 20, 50, 100, 500, 1000, 5000, 10000, 50,000, 100,000, 500,000, 1,000,000, 10,000,000, 50,000,000 or 1,000,000,000 identifiers are loaded per genome sample. In certain implementations, the average number of identifiers loaded per sample genome is less than, or greater than, about 1, 2, 3, 4, 5, 6, 7, 8, 9, 10, 20, 50, 100, 500, 1000, 5000, 10000, 50,000, 100,000, 500,000, 1,000,000, 10,000,000, 50,000,000 or 1,000,000,000 identifiers per genome sample. The identifiers are generally unique or non-unique.

One example format uses from about 2 to about 1,000,000 different tags, or from about 5 to about 150 different tags, or from about 20 to about 50 different tags, ligated to both ends of a target nucleic acid molecule. For 20-50×20-50 tags, a total of 400-2500 tags are created. Such numbers of tags are typically sufficient for different molecules having the same start and stop points to have a high probability (e.g., at least 94%, 99.5%, 99.99%, 99.999%) of receiving different combinations of tags.

In some implementations, identifiers are predetermined, random, or semi-random sequence oligonucleotides. In other implementations, a plurality of barcodes may be used such that barcodes are not necessarily unique to one another in the plurality. In these implementations, barcodes are generally attached (e.g., by ligation or PCR amplification) to individual molecules such that the combination of the barcode and the sequence it may be attached to creates a unique sequence that may be individually tracked. As described herein, detection of non-uniquely tagged barcodes in combination with sequence data of beginning (start) and end (stop) portions of sequence reads typically allows for the assignment of a unique identity to a particular molecule. The length, or number of base pairs, of an individual sequence read are also optionally used to assign a unique identity to a given molecule. As described herein, fragments from a single strand of nucleic acid having been assigned a unique identity, may thereby permit subsequent identification of fragments from the parent strand, and/or a complementary strand.

Nucleic Acid Amplification

Sample nucleic acids flanked by adapters are typically amplified by PCR and other amplification methods using nucleic acid primers binding to primer binding sites in adapters flanking a DNA molecule to be amplified. In some implementations, amplification methods involve cycles of extension, denaturation and annealing resulting from thermocycling, or can be isothermal as, for example, in transcription mediated amplification. Other example amplification methods that are optionally utilized, include the ligase chain reaction, strand displacement amplification, nucleic acid sequence-based amplification, and self-sustained sequence-based replication, among other approaches.

One or more rounds of amplification cycles are generally applied to introduce sample indexes/tags to a nucleic acid molecule using conventional nucleic acid amplification methods. The amplifications are typically conducted in one or more reaction mixtures. In some implementations, molecular tags and sample indexes/tags are introduced prior to and/or after sequence capturing steps are performed. In some implementations, only the molecular tags are introduced prior to probe capturing and the sample indexes/tags are introduced after sequence capturing steps are performed. In certain implementations, both the molecular tags and the sample indexes/tags are introduced prior to performing probe-based capturing steps. In some implementations, the sample indexes/tags are introduced after sequence capturing steps (i.e., enrichment of nucleic acids) are performed. Typically, sequence capturing protocols involve introducing a single-stranded nucleic acid molecule complementary to a targeted nucleic acid sequence, e.g., a coding sequence of a genomic region and mutation of such region associated with a cancer type. Typically, the amplification reactions generate a plurality of non-uniquely or uniquely tagged nucleic acid amplicons with molecular tags and sample indexes/tags at size ranging from about 200 nucleotides (nt) to about 700 nt, from 250 nt to about 350 nt, or from about 320 nt to about 550 nt. In some implementations, the amplicons have a size of about 300 nt. In some implementations, the amplicons have a size of about 500 nt.

Nucleic Acid Enrichment

In some implementations, sequences are enriched prior to sequencing the nucleic acids. Enrichment is optionally performed for specific target regions or nonspecifically ("target sequences"). In some implementations, targeted regions of interest may be enriched with nucleic acid capture probes ("baits") selected for one or more bait set panels using a differential tiling and capture scheme. A differential tiling and capture scheme generally uses bait sets of different relative concentrations to differentially tile (e.g., at different "resolutions") across genomic sections associated with the baits, subject to a set of constraints (e.g., sequencer constraints such as sequencing load, utility of each bait, etc.), and capture the targeted nucleic acids at a desired level for downstream sequencing. These targeted genomic sections of interest optionally include natural or synthetic nucleotide sequences of the nucleic acid construct. In some implementations, biotin-labeled beads with probes to one or more sections of interest can be used to capture target sequences, and optionally followed by amplification of those sections, to enrich for the regions of interest.

Sequence capture typically involves the use of oligonucleotide probes that hybridize to the target nucleic acid sequence. In certain implementations, a probe set strategy involves tiling the probes across a section of interest. Such probes can be, for example, from about 60 to about 120 nucleotides in length. The set can have a depth of about 2×, 3×, 4×, 5×, 6×, 8×, 9×, 10×, 15×, 20×, 50× or more. The effectiveness of sequence capture generally depends, in part, on the length of the sequence in the target molecule that is complementary (or nearly complementary) to the sequence of the probe.

Nucleic Acid Sequencing

After extraction and isolation of cfDNA from samples, the cfDNA may be sequenced at steps 103 and 104. Sample nucleic acids, optionally flanked by adapters, with or without prior amplification are generally subject to sequencing. Sequencing methods or commercially available formats that are optionally utilized include, for example, Sanger sequencing, high-throughput sequencing, bisulfite sequencing, pyrosequencing, sequencing-by-synthesis, single-molecule sequencing, nanopore-based sequencing, semiconductor sequencing, sequencing-by-ligation, sequencing-by-hybridization, RNA-Seq (Illumina), Digital Gene Expression (Helicos), next generation sequencing (NGS), Single Molecule Sequencing by Synthesis (SMSS) (Helicos), massively-parallel sequencing, Clonal Single Molecule Array (Solexa), shotgun sequencing, Ion Torrent, Oxford Nanopore, Roche Genia, primer walking, sequencing using PacBio, SOLiD, Ion Torrent, or nanopore platforms. Sequencing reactions can be performed in a variety of sample processing units, which may include multiple lanes, multiple channels, multiple wells, or other means of processing multiple sample sets substantially simultaneously. Sample processing units can also include multiple sample chambers to enable the processing of multiple runs simultaneously.

The sequencing reactions can be performed on one more nucleic acid fragment types or sections known to contain markers of cancer or of other diseases. The sequencing reactions can also be performed on any nucleic acid fragment present in the sample. The sequence reactions may provide for sequence coverage of the genome of at least about 5%, 10%, 15%, 20%, 25%, 30%, 40%, 50%, 60%, 70%, 80%, 90%, 95%, 99%, 99.9% or 100% of the genome. In other cases, sequence coverage of the genome may be less than about 5%, 10%, 15%, 20%, 25%, 30%, 40%, 50%, 60%, 70%, 80%, 90%, 95%, 99%, 99.9% or 100% of the genome.

Simultaneous sequencing reactions may be performed using multiplex sequencing techniques. In some implementations, cell-free polynucleotides are sequenced with at least about 1000, 2000, 3000, 4000, 5000, 6000, 7000, 8000, 9000, 10000, 50000, or 100,000 sequencing reactions. In other implementations, cell-free polynucleotides are sequenced with less than about 1000, 2000, 3000, 4000, 5000, 6000, 7000, 8000, 9000, 10000, 50000, or 100,000 sequencing reactions. Sequencing reactions are typically performed sequentially or simultaneously. Subsequent data analysis is generally performed on all or part of the sequencing reactions. In some implementations, data analysis is performed on at least about 1000, 2000, 3000, 4000, 5000, 6000, 7000, 8000, 9000, 10000, 50000, or 100,000 sequencing reactions. In other implementations, data analysis may be performed on less than about 1000, 2000, 3000, 4000, 5000, 6000, 7000, 8000, 9000, 10000, 50000, or 100,000 sequencing reactions. An example read depth is from about 1000 to about 50000 reads per locus (base position).

In some implementations, a nucleic acid population is prepared for sequencing by enzymatically forming blunt-ends on double-stranded nucleic acids with single-stranded overhangs at one or both ends. In these implementations, the population is typically treated with an enzyme having a 5'-3' DNA polymerase activity and a 3'-5' exonuclease activity in the presence of the nucleotides (e.g., A, C, G and T or U). Example enzymes or catalytic fragments thereof that are optionally used include Klenow large fragment and T4 polymerase. At 5' overhangs, the enzyme typically extends the recessed 3' end on the opposing strand until it is flush with the 5' end to produce a blunt end. At 3' overhangs, the enzyme generally digests from the 3' end up to and sometimes beyond the 5' end of the opposing strand. If this digestion proceeds beyond the 5' end of the opposing strand, the gap can be filled in by an enzyme having the same polymerase activity that is used for 5' overhangs. The formation of blunt-ends on double-stranded nucleic acids facilitates, for example, the attachment of adapters and subsequent amplification.

In some implementations, nucleic acid populations are subject to additional processing, such as the conversion of single-stranded nucleic acids to double-stranded and/or conversion of RNA to DNA. These forms of nucleic acid are also optionally linked to adapters and amplified.

With or without prior amplification, nucleic acids subject to the process of forming blunt-ends described above, and optionally other nucleic acids in a sample, can be sequenced to produce sequenced nucleic acids. A sequenced nucleic acid can refer either to the sequence of a nucleic acid (i.e., sequence information) or a nucleic acid whose sequence has been determined. Sequencing can be performed so as to provide sequence data of individual nucleic acid molecules in a sample either directly or indirectly from a consensus sequence of amplification products of an individual nucleic acid molecule in the sample.

In some implementations, double-stranded nucleic acids with single-stranded overhangs in a sample after blunt-end formation are linked at both ends to adapters including barcodes, and the sequencing determines nucleic acid sequences as well as in-line barcodes introduced by the adapters. The blunt-end DNA molecules are optionally ligated to a blunt end of an at least partially double-stranded adapter (e.g., a Y shaped or bell-shaped adapter). Alternatively, blunt ends of sample nucleic acids and adapters can be tailed with complementary nucleotides to facilitate ligation (e.g., sticky end ligation).

The nucleic acid sample is typically contacted with a sufficient number of adapters such that there is a low probability (e.g., <1 or 0.1%) that any two copies of the same nucleic acid receive the same combination of adapter barcodes from the adapters linked at both ends. The use of adapters in this manner permits identification of families of nucleic acid sequences with the same start and stop points on a reference nucleic acid and linked to the same combination of barcodes. Such a family represents sequences of amplification products of a template/parent nucleic acid in the sample before amplification. The sequences of family members can be compiled to derive consensus nucleotide(s) or a complete consensus sequence for a nucleic acid molecule in the original sample, as modified by blunt end formation and adapter attachment. In other words, the nucleotide occupying a specified position of a nucleic acid in the sample is determined to be the consensus of nucleotides occupying that corresponding position in family member sequences. Families can include sequences of one or both strands of a double-stranded nucleic acid. If members of a family include sequences of both strands from a double-stranded nucleic acid, sequences of one strand are converted to their complement for purposes of compiling all sequences to derive consensus nucleotide(s) or sequences. Some families include only a single member sequence. In this case, this sequence can be taken as the sequence of a nucleic acid in the sample before amplification. Alternatively, families with only a single member sequence may be eliminated from subsequent analysis.

Nucleotide variations in sequenced nucleic acids can be determined by comparing sequenced nucleic acids with a reference sequence. The reference sequence is often a known sequence, e.g., a known whole or partial genome sequence from a subject (e.g., a whole genome sequence of a human subject). The reference sequence can be, for example, hG19 or hG38. The sequenced nucleic acids can represent sequences determined directly for a nucleic acid in a sample, or a consensus of sequences of amplification products of such a nucleic acid, as described above. A comparison can be performed at one or more designated positions on a reference sequence. A subset of sequenced nucleic acids can be identified including a position corresponding with a designated position of the reference sequence when the respective sequences are maximally aligned. Within such a subset it can be determined which, if any, sequenced nucleic acids include a nucleotide variation at the designated position, the length of a given cfDNA fragment based upon where its endpoints (i.e., it 5' and 3' terminal nucleotides) map to the reference sequence, the offset of a midpoint of a given cfDNA fragment from a midpoint of a genomic region in the cfDNA fragment, and optionally which if any, include a reference nucleotide (i.e., same as in the reference sequence). If the number of sequenced nucleic acids in the subset including a nucleotide variant exceeding a selected threshold, then a variant nucleotide can be called at the designated position. The threshold can be a simple number, such as at least 1, 2, 3, 4, 5, 6, 7, 9, or 10 sequenced nucleic acids within the subset including the nucleotide variant or it can be a ratio, such as a least 0.5, 1, 2, 3, 4, 5, 10, 15, or 20 of sequenced nucleic acids within the subset that include the nucleotide variant, among other possibilities. The comparison can be repeated for any designated position of interest in the reference sequence. Sometimes a comparison can be performed for designated positions occupying at least about 20, 100, 200, or 300 contiguous positions on a reference sequence, e.g., about 20-500, or about 50-300 contiguous positions.

Additional details regarding nucleic acid sequencing, including the formats and applications described herein are also provided in, for example, Levy et al., Annual Review of Genomics and Human Genetics, 17: 95-115 (2016), Liu et al., J. of Biomedicine and Biotechnology, Volume 2012, Article ID 251364:1-11 (2012), Voelkerding et al., Clinical Chem., 55: 641-658 (2009), MacLean et al., Nature Rev. Microbiol., 7: 287-296 (2009), Astier et al., J Am Chem Soc., 128(5):1705-10 (2006), U.S. Pat. Nos. 6,210,891, 6,258,568, 6,833,246, 7,115,400, 6,969,488, 5,912,148, 6,130,073, 7,169,560, 7,282,337, 7,482,120, 7,501,245, 6,818,395, 6,911,345, 7,501,245, 7,329,492, 7,170,050, 7,302,146, 7,313,308, and 7,476,503, which are each incorporated by reference in their entirety.

Sequencing Panel

To improve the likelihood of detecting genomic regions of interest and optionally, tumor indicating mutations, the sections of DNA sequenced may comprise a panel of genes or genomic sections that comprise known genomic regions. Selection of a limited section for sequencing (e.g., a limited panel) can reduce the total sequencing needed (e.g., a total amount of nucleotides sequenced). A sequencing panel can target a plurality of different genes or regions, for example, to detect a single cancer, a set of cancers, or all cancers. Alternatively, DNA may be sequenced by whole genome sequencing (WGS) or other unbiased sequencing method without the use of a sequencing panel. Examples of suitable panel and targets for use in panels can be found in the epigenetic targets described in U.S. provisional patent application 62/799,637, filed Jan. 31, 2019, which is incorporated by reference in its entirety.

In some aspects, a panel that targets a plurality of different genes or genomic regions (e.g., transcriptional factor binding regions, distal regulatory elements (DREs), repetitive elements, intron-exon junctions, transcriptional start sites (TSSs), and/or the like) is selected such that a determined proportion of subjects having a cancer exhibits a genetic variant or tumor marker in one or more different genes in the panel. The panel may be selected to limit a region for sequencing to a fixed number of base pairs. The panel may be selected to sequence a desired amount of DNA. The panel may be further selected to achieve a desired sequence read depth. The panel may be selected to achieve a desired sequence read depth or sequence read coverage for an amount of sequenced base pairs. The panel may be selected to achieve a theoretical sensitivity, a theoretical specificity, and/or a theoretical accuracy for detecting one or more genetic variants in a sample.

Probes for detecting the panel of regions can include those for detecting genomic regions of interest (hotspot regions) as well as nucleosome-aware probes (e.g., KRAS codons 12 and 13) and may be designed to optimize capture based on analysis of cfDNA coverage and fragment size variation impacted by nucleosome binding patterns and GC sequence composition. Regions used herein can also include non-hotspot regions optimized based on nucleosome positions and GC models. The panel can comprise a plurality of subpanels, including subpanels for identifying tissue of origin (e.g., use of published literature to define 50-100 baits representing genes with most diverse transcription profile across tissues (not necessarily promoters)), whole genome scaffold (e.g., for identifying ultra-conservative genomic content and tiling sparsely across chromosomes with handful of probes for copy number base lining purposes), transcription start site (TSS)/CpG islands (e.g., for capturing differential methylated regions (e.g., Differentially Methylated Regions (DMRs)) in for example in promoters of tumor suppressor genes (e.g., SEPT9/VIM in colorectal cancer)). In some implementations, markers for a tissue of origin are tissue-specific epigenetic markers.

Some examples of listings of genomic locations of interest may be found in Table 1 and Table 2. In some implementations, genomic locations used in the methods of the present disclosure comprise at least a portion of at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, or 97 of the genes of Table 1. In some implementations, genomic locations used in the methods of the present disclosure comprise at least 5, at least 10, at least 15, at least 20, at least 25, at least 30, at least 35, at least 40, at least 45, at least 50, at least 55, at least 60, at least 65, or 70 of the SNVs of Table 1. In some implementations, genomic locations used in the methods of the present disclosure comprise at least 1, at least 2, at least 3, at least 4, at least 5, at least 6, at least 7, at least 8, at least 9, at least 10, at least 11, at least 12, at least 13, at least 14, at least 15, at least 16, at least 17, or 18 of the CNVs of Table 1. In some implementations, genomic locations used in the methods of the present disclosure comprise at least 1, at least 2, at least 3, at least 4, at least 5, or 6 of the fusions of Table 1. In some implementations, genomic locations used in the methods of the present disclosure comprise at least a portion of at least 1, at least 2, or 3 of the indels of Table 1. In some implementations, genomic locations used in the methods of the present disclosure comprise at least a portion of at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, or 115 of the genes of Table 2. In some implementations, genomic locations used in the methods of the present disclosure comprise at least 5, at least 10, at least 15, at least 20, at least 25, at least 30, at least 35, at least 40, at least 45, at least 50, at least 55, at least 60, at least 65, at least 70, or 73 of the SNVs of Table 2. In some implementations, genomic locations used in the methods of the present disclosure comprise at least 1, at least 2, at least 3, at least 4, at least 5, at least 6, at least 7, at least 8, at least 9, at least 10, at least 11, at least 12, at least 13, at least 14, at least 15, at least 16, at least 17, or 18 of the CNVs of Table 2. In some implementations, genomic locations used in the methods of the present disclosure comprise at least 1, at least 2, at least 3, at least 4, at least 5, or 6 of the fusions of Table 2. In some implementations, genomic locations used in the methods of the present disclosure comprise at least a portion of at least 1, at least 2, at least 3, at least 4, at least 5, at least 6, at least 7, at least 8, at least 9, at least 10, at least 11, at least 12, at least 13, at least 14, at least 15, at least 16, at least 17, or 18 of the indels of Table 2. Each of these genomic locations of interest may be identified as a backbone region or hot-spot region for a given bait set panel. In one or more examples, the methods of the present disclosure may be implemented using all of the mutations included in Table 1 and/or Table 2.

tion. Moreover, smokers can develop other lung conditions that make cancer detection more difficult, such as the development of irregular nodules in the lungs. In some implementations, the methods described herein detect the response of patients to cancer therapy (particularly in high risk patients) earlier than is possible for existing methods of cancer detection.

A genomic location may be selected for inclusion in a sequencing panel based on a number of subjects with a cancer that have a tumor marker in that gene or region. A

TABLE 1

| Point Mutations (SNVs) | | | | | | Amplifications (CNVs) | | Fusions | Indels |
|---|---|---|---|---|---|---|---|---|---|
| AKT1 | ALK | APC | AR | ARAF | ARID1A | AR | BRAF | ALK | EGFR |
| ATM | BRAF | BRCA1 | BRCA2 | CCND1 | CCND2 | CCND1 | CCND2 | FGFR2 | (exons |
| CCNE1 | CDH1 | CDK4 | CDK6 | CDKN2A | CDKN2B | CCNE1 | CDK4 | FGFR3 | 19 & 20) |
| CTNNB1 | EGFR | ERBB2 | ESR1 | EZH2 | FBXW7 | CDK6 | EGFR | NTRK1 | ERBB2 |
| FGFR1 | FGFR2 | FGFR3 | GATA3 | GNA11 | GNAQ | ERBB2 | FGFR1 | RET | (exons |
| GNAS | HNF1A | HRAS | IDH1 | IDH2 | JAK2 | FGFR2 | KIT | ROS1 | 19 & 20) |
| JAK3 | KIT | KRAS | MAP2K1 | MAP2K2 | MET | KRAS | MET | | MET |
| MLH1 | MPL | MYC | NF1 | NFE2L2 | NOTCH1 | MYC | PDGFRA | | (exon 14 |
| NPM1 | NRAS | NTRK1 | PDGFRA | PIK3CA | PTEN | PIK3CA | RAF1 | | skipping) |
| PTPN11 | RAF1 | RB1 | RET | RHEB | RHOA | | | | |
| RIT1 | ROS1 | SMAD4 | SMO | SRC | STK11 | | | | |
| TERT | TP53 | TSC1 | VHL | | | | | | |

-

TABLE 2

| Point Mutations (SNVs) | | | | | | Amplifications (CNVs) | | Fusions | Indels |
|---|---|---|---|---|---|---|---|---|---|
| AKT1 | ALK | APC | AR | ARAF | ARID1A | AR | BRAF | ALK | EGFR |
| ATM | BRAF | BRCA1 | BRCA2 | CCND1 | CCND2 | CCND1 | CCND2 | FGFR2 | (exons |
| CCNE1 | CDH1 | CDK4 | CDK6 | CDKN2A | DDR2 | CCNE1 | CDK4 | FGFR3 | 19 & 20) |
| CTNNB1 | EGFR | ERBB2 | ESR1 | EZH2 | FBXW7 | CDK6 | EGFR | NTRK1 | ERBB2 |
| FGFR1 | FGFR2 | FGFR3 | GATA3 | GNA11 | GNAQ | ERBB2 | FGFR1 | RET | (exons |
| GNAS | HNF1A | HRAS | IDH1 | IDH2 | JAK2 | FGFR2 | KIT | ROS1 | 19 & 20) |
| JAK3 | KIT | KRAS | MAP2K1 | MAP2K2 | MET | KRAS | MET | | MET |
| MLH1 | MPL | MYC | NF1 | NFE2L2 | NOTCH1 | MYC | PDGFRA | | (exon 14 |
| NPM1 | NRAS | NTRK1 | PDGFRA | PIK3CA | PTEN | PIK3CA | RAF1 | | skipping) |
| PTPN11 | RAF1 | RB1 | RET | RHEB | RHOA | | | | ATM |
| RIT1 | ROS1 | SMAD4 | SMO | MAPK1 | STK11 | | | | |
| TERT | TP53 | TSC1 | VHL | MAPK3 | MTOR | | | | |
| NTRK3 | | | | | | | | | APC |
| | | | | | | | | | ARID1A |
| | | | | | | | | | BRCA1 |
| | | | | | | | | | BRCA2 |
| | | | | | | | | | CDH1 |
| | | | | | | | | | CDKN2A |
| | | | | | | | | | GATA3 |
| | | | | | | | | | KIT |
| | | | | | | | | | MLH1 |
| | | | | | | | | | MTOR |
| | | | | | | | | | NF1 |
| | | | | | | | | | PDGFRA |
| | | | | | | | | | PTEN |
| | | | | | | | | | RB1 |
| | | | | | | | | | SMAD4 |
| | | | | | | | | | STK11 |
| | | | | | | | | | TP53 |
| | | | | | | | | | TSC1 |
| | | | | | | | | | VHL |

In some implementations, the one or more regions in the panel comprise one or more loci from one or a plurality of genes for detecting residual cancer after surgery. This detection can be earlier than is possible for existing methods of cancer detection. In some implementations, the one or more genomic locations in the panel comprise one or more loci from one or a plurality of genes for detecting cancer in a high-risk patient population. For example, smokers have much higher rates of lung cancer than the general populagenomic location may be selected for inclusion in a sequencing panel based on prevalence of subjects with a cancer and a tumor marker present in that gene. Presence of a tumor marker in a region may be indicative of a subject having cancer.

In some instances, the panel may be selected using information from one or more databases. The information regarding a cancer may be derived from cancer tumor biopsies or cfDNA assays. A database may comprise infor mation describing a population of sequenced tumor samples. A database may comprise information about mRNA expression in tumor samples. A database may comprise information about regulatory elements or genomic regions in tumor samples. The information relating to the sequenced tumor samples may include the frequency of various genetic variants and describe the genes or regions in which the genetic variants occur. The genetic variants may be tumor markers. A non-limiting example of such a database is COSMIC. COSMIC is a catalogue of somatic mutations found in various cancers. For a particular cancer, COSMIC ranks genes based on frequency of mutation. A gene may be selected for inclusion in a panel by having a high frequency of mutation within a given gene. For instance, COSMIC indicates that 33% of a population of sequenced breast cancer samples have a mutation in TP53 and 22% of a population of sampled breast cancers have a mutation in KRAS. Other ranked genes, including APC, have mutations found only in about 4% of a population of sequenced breast cancer samples. TP53 and KRAS may be included in a sequencing panel based on having relatively high frequency among sampled breast cancers (compared to APC, for example, which occurs at a frequency of about 4%). COSMIC is provided as a non-limiting example, however, any database or set of information may be used that associates a cancer with tumor marker located in a gene or genetic region. In another example, as provided by COSMIC, of 1156 biliary tract cancer samples, 380 samples (33%) carried mutations in TP53. Several other genes, such as APC, have mutations in 4-8% of all samples. Thus, TP53 may be selected for inclusion in the panel based on a relatively high frequency in a population of biliary tract cancer samples.

A gene or genomic section may be selected for a panel where the frequency of a tumor marker is significantly greater in sampled tumor tissue or circulating tumor DNA than found in a given background population. A combination of genomic locations may be selected for inclusion of a panel such that at least a majority of subjects having a cancer may have a tumor marker or genomic region present in at least one of the genomic location or genes in the panel. The combination of genomic location may be selected based on data indicating that, for a particular cancer or set of cancers, a majority of subjects have one or more tumor markers in one or more of the selected regions. For example, to detect cancer 1, a panel comprising regions A, B, C, and/or D may be selected based on data indicating that 90% of subjects with cancer 1 have a tumor marker in regions A, B, C, and/or D of the panel. Alternately, tumor markers may be shown to occur independently in two or more regions in subjects having a cancer such that, combined, a tumor marker in the two or more regions is present in a majority of a population of subjects having a cancer. For example, to detect cancer 2, a panel comprising regions X, Y, and Z may be selected based on data indicating that 90% of subjects have a tumor marker in one or more regions, and in 30% of such subjects a tumor marker is detected only in region X, while tumor markers are detected only in regions Y and/or Z for the remainder of the subjects for whom a tumor marker was detected. Tumor markers present in one or more genomic locations previously shown to be associated with one or more cancers may be indicative of or predictive of a subject having cancer if a tumor marker is detected in one or more of those regions 50% or more of the time. Computational approaches such as models employing conditional probabilities of detecting cancer given a cancer frequency for a set of tumor markers within one or more regions may be used to predict which regions, alone or in combination, may be predictive of cancer. Other approaches for panel selection involve the use of databases describing information from studies employing comprehensive genomic profiling of tumors with large panels and/or whole genome sequencing (WGS, RNA-seq, Chip-seq, bisulfate sequencing, ATAC-seq, and others). Information gleaned from literature may also describe pathways commonly affected and mutated in certain cancers. Panel selection may be further informed by the use of ontologies describing genetic information.

Genes included in the panel for sequencing can include the fully transcribed region, the promoter region, enhancer regions, regulatory elements, and/or downstream sequence. To further increase the likelihood of detecting tumor indicating mutations only exons may be included in the panel. The panel can comprise all exons of a selected gene, or only one or more of the exons of a selected gene. The panel may comprise of exons from each of a plurality of different genes. The panel may comprise at least one exon from each of the plurality of different genes.

In some aspects, a panel of exons from each of a plurality of different genes is selected such that a determined proportion of subjects having a cancer exhibit a genetic variant in at least one exon in the panel of exons.

At least one full exon from each different gene in a panel of genes may be sequenced. The sequenced panel may comprise exons from a plurality of genes. The panel may comprise exons from 2 to 100 different genes, from 2 to 70 genes, from 2 to 50 genes, from 2 to 30 genes, from 2 to 15 genes, or from 2 to 10 genes.

A selected panel may comprise a varying number of exons. The panel may comprise from 2 to 3000 exons. The panel may comprise from 2 to 1000 exons. The panel may comprise from 2 to 500 exons. The panel may comprise from 2 to 100 exons. The panel may comprise from 2 to 50 exons. The panel may comprise no more than 300 exons. The panel may comprise no more than 200 exons. The panel may comprise no more than 100 exons. The panel may comprise no more than 50 exons. The panel may comprise no more than 40 exons. The panel may comprise no more than 30 exons. The panel may comprise no more than 25 exons. The panel may comprise no more than 20 exons. The panel may comprise no more than 15 exons. The panel may comprise no more than 10 exons. The panel may comprise no more than 9 exons. The panel may comprise no more than 8 exons. The panel may comprise no more than 7 exons.

The panel may comprise one or more exons from a plurality of different genes. The panel may comprise one or more exons from each of a proportion of the plurality of different genes. The panel may comprise at least two exons from each of at least 25%, 50%, 75% or 90% of the different genes. The panel may comprise at least three exons from each of at least 25%, 50%, 75% or 90% of the different genes. The panel may comprise at least four exons from each of at least 25%, 50%, 75% or 90% of the different genes.

The sizes of the sequencing panel may vary. A sequencing panel may be made larger or smaller (in terms of nucleotide size) depending on several factors including, for example, the total amount of nucleotides sequenced or a number of unique molecules sequenced for a particular region in the panel. The sequencing panel can be sized 5 kb to 50 kb. The sequencing panel can be 10 kb to 30 kb in size. The sequencing panel can be 12 kb to 20 kb in size. The sequencing panel can be 12 kb to 60 kb in size. The sequencing panel can be at least 10 kb, 12 kb, 15 kb, 20 kb, 25 kb, 30 kb, 35 kb, 40 kb, 45 kb, 50 kb, 60 kb, 70 kb, 80 kb, 90 kb, 100 kb, 110 kb, 120 kb, 130 kb, 140 kb, or 150 kb in size. The sequencing panel may be less than 100 kb, 90 kb, 80 kb, 70 kb, 60 kb, or 50 kb in size.

The panel selected for sequencing can comprise at least 1, 5, 10, 15, 20, 25, 30, 40, 50, 60, 80, or 100 genomic locations (e.g., that each include genomic regions of interest). In some cases, the genomic locations in the panel are selected that the size of the locations are relatively small. In some cases, the regions in the panel have a size of about 10 kb or less, about 8 kb or less, about 6 kb or less, about 5 kb or less, about 4 kb or less, about 3 kb or less, about 2.5 kb or less, about 2 kb or less, about 1.5 kb or less, or about 1 kb or less or less. In some cases, the genomic locations in the panel have a size from about 0.5 kb to about 10 kb, from about 0.5 kb to about 6 kb, from about 1 kb to about 11 kb, from about 1 kb to about 15 kb, from about 1 kb to about 20 kb, from about 0.1 kb to about 10 kb, or from about 0.2 kb to about 1 kb. For example, the regions in the panel can have a size from about 0.1 kb to about 5 kb.

The panel selected herein can allow for deep sequencing that is sufficient to detect low-frequency genetic variants (e.g., in cell-free nucleic acid molecules obtained from a sample). An amount of genetic variants in a sample may be referred to in terms of the minor allele frequency for a given genetic variant. The mutant allele frequency may refer to the frequency at which mutant alleles occur in a given population of nucleic acids, such as a sample. Genetic variants at a low minor allele frequency may have a relatively low frequency of presence in a sample. In some cases, the panel allows for detection of genetic variants at a minor allele frequency of at least 0.0001%, 0.001%, 0.005%, 0.01%, 0.05%, 0.1%, or 0.5%. The panel can allow for detection of genetic variants at a minor allele frequency of 0.001% or greater. The panel can allow for detection of genetic variants at a minor allele frequency of 0.01% or greater. The panel can allow for detection of genetic variant present in a sample at a frequency of as low as 0.0001%, 0.001%, 0.005%, 0.01%, 0.025%, 0.05%, 0.075%, 0.1%, 0.25%, 0.5%, 0.75%, or 1.0%. The panel can allow for detection of tumor markers present in a sample at a frequency of at least 0.0001%, 0.001%, 0.005%, 0.01%, 0.025%, 0.05%, 0.075%, 0.1%, 0.25%, 0.5%, 0.75%, or 1.0%. The panel can allow for detection of tumor markers at a frequency in a sample as low as 1.0%. The panel can allow for detection of tumor markers at a frequency in a sample as low as 0.75%. The panel can allow for detection of tumor markers at a frequency in a sample as low as 0.5%. The panel can allow for detection of tumor markers at a frequency in a sample as low as 0.25%. The panel can allow for detection of tumor markers at a frequency in a sample as low as 0.1%. The panel can allow for detection of tumor markers at a frequency in a sample as low as 0.075%. The panel can allow for detection of tumor markers at a frequency in a sample as low as 0.05%. The panel can allow for detection of tumor markers at a frequency in a sample as low as 0.025%. The panel can allow for detection of tumor markers at a frequency in a sample as low as 0.01%. The panel can allow for detection of tumor markers at a frequency in a sample as low as 0.005%. The panel can allow for detection of tumor markers at a frequency in a sample as low as 0.001%. The panel can allow for detection of tumor markers at a frequency in a sample as low as 0.0001%. The panel can allow for detection of tumor markers in sequenced cfDNA at a frequency in a sample as low as 1.0% to 0.0001%. The panel can allow for detection of tumor markers in sequenced cfDNA at a frequency in a sample as low as 0.01% to 0.0001%.

A genetic variant can be exhibited in a percentage of a population of subjects who have a disease (e.g., cancer). In some cases, at least 1%, 2%, 3%, 5%, 10%, 20%, 30%, 40%, 50%, 60%, 70%, 80%, 90%, 95%, or 99% of a population having the cancer exhibit one or more genetic variants in at least one of the regions in the panel. For example, at least 80% of a population having the cancer may exhibit one or more genetic variants in at least one of the genomic positions in the panel.

The panel can comprise one or more locations comprising genomic regions of interest from each of one or more genes. In some cases, the panel can comprise one or more locations comprising genomic regions of interest from each of at least 1, 2, 3, 4, 5, 6, 7, 8, 9, 10, 15, 20, 25, 30, 40, 50, or 80 genes. In some cases, the panel can comprise one or more locations comprising genomic regions of interest from each of at most 1, 2, 3, 4, 5, 6, 7, 8, 9, 10, 15, 20, 25, 30, 40, 50, or 80 genes. In some cases, the panel can comprise one or more locations comprising genomic regions of interest from each of from about 1 to about 80, from 1 to about 50, from about 3 to about 40, from 5 to about 30, from 10 to about 20 different genes.

The locations comprising genomic regions in the panel can be selected so that one or more epigenetically modified regions are detected. The one or more epigenetically modified regions can be acetylated, methylated, ubiquitylated, phosphorylated, sumoylated, ribosylated, and/or citrullinated. For example, the regions in the panel can be selected so that one or more methylated regions are detected.

The regions in the panel can be selected so that they comprise sequences differentially transcribed across one or more tissues. In some cases, the locations comprising genomic regions can comprise sequences transcribed in certain tissues at a higher level compared to other tissues. For example, the locations comprising genomic regions can comprise sequences transcribed in certain tissues but not in other tissues.

The genomic locations in the panel can comprise coding and/or non-coding sequences. For example, the genomic locations in the panel can comprise one or more sequences in exons, introns, promoters, 3' untranslated regions, 5' untranslated regions, regulatory elements, transcription start sites, and/or splice sites. In some cases, the regions in the panel can comprise other non-coding sequences, including pseudogenes, repeat sequences, transposons, viral elements, and telomeres. In some cases, the genomic locations in the panel can comprise sequences in non-coding RNA, e.g., ribosomal RNA, transfer RNA, Piwi-interacting RNA, and microRNA.

The genomic locations in the panel can be selected to detect (diagnose) a cancer with a desired level of sensitivity (e.g., through the detection of one or more genetic variants). For example, the regions in the panel can be selected to detect the cancer (e.g., through the detection of one or more genetic variants) with a sensitivity of at least 50%, 55%, 60%, 65%, 70%, 75%, 80%, 85%, 90%, 95%, 96%, 97%, 98%, 99%, 99.5%, or 99.9%. The genomic locations in the panel can be selected to detect the cancer with a sensitivity of 100%.

The genomic locations in the panel can be selected to detect (diagnose) a cancer with a desired level of specificity (e.g., through the detection of one or more genetic variants). For example, the genomic locations in the panel can be selected to detect cancer (e.g., through the detection of one or more genetic variants) with a specificity of at least 50%, 55%, 60%, 65%, 70%, 75%, 80%, 85%, 90%, 95%, 96%, 97%, 98%, 99%, 99.5%, or 99.9%. The genomic locations in the panel can be selected to detect the one or more genetic variant with a specificity of 100%.

The genomic locations in the panel can be selected to detect (diagnose) a cancer with a desired positive predictive value. Positive predictive value can be increased by increasing sensitivity (e.g., chance of an actual positive being detected) and/or specificity (e.g., chance of not mistaking an actual negative for a positive). As a non-limiting example, genomic locations in the panel can be selected to detect the one or more genetic variant with a positive predictive value of at least 50%, 55%, 60%, 65%, 70%, 75%, 80%, 85%, 90%, 95%, 96%, 97%, 98%, 99%, 99.5%, or 99.9%. The regions in the panel can be selected to detect the one or more genetic variant with a positive predictive value of 100%.

The genomic locations in the panel can be selected to detect (diagnose) a cancer with a desired accuracy. As used herein, the term "accuracy" may refer to the ability of a test to discriminate between a disease condition (e.g., cancer) and healthy condition. Accuracy can be quantified using measures such as sensitivity and specificity, predictive values, likelihood ratios, the area under the ROC curve, Youden's index and/or diagnostic odds ratio.

Accuracy may be presented as a percentage, which refers to a ratio between the number of tests giving a correct result and the total number of tests performed. The regions in the panel can be selected to detect cancer with an accuracy of at least 50%, 55%, 60%, 65%, 70%, 75%, 80%, 85%, 90%, 95%, 96%, 97%, 98%, 99%, 99.5%, or 99.9%. The genomic locations in the panel can be selected to detect cancer with an accuracy of 100%.

A panel may be selected to be highly sensitive and detect low frequency genetic variants. For instance, a panel may be selected such that a genetic variant or tumor marker present in a sample at a frequency as low as 0.01%, 0.05%, or 0.001% may be detected at a sensitivity of at least 50%, 55%, 60%, 65%, 70%, 75%, 80%, 85%, 90%, 95%, 96%, 97%, 98%, 99%, 99.5%, or 99.9%. Genomic locations in a panel may be selected to detect a tumor marker present at a frequency of 1% or less in a sample with a sensitivity of 70% or greater. A panel may be selected to detect a tumor marker at a frequency in a sample as low as 0.1% with a sensitivity of at least 50%, 55%, 60%, 65%, 70%, 75%, 80%, 85%, 90%, 95%, 96%, 97%, 98%, 99%, 99.5%, or 99.9%. A panel may be selected to detect a tumor marker at a frequency in a sample as low as 0.01% with a sensitivity of at least 50%, 55%, 60%, 65%, 70%, 75%, 80%, 85%, 90%, 95%, 96%, 97%, 98%, 99%, 99.5%, or 99.9%. A panel may be selected to detect a tumor marker at a frequency in a sample as low as 0.001% with a sensitivity of at least 50%, 55%, 60%, 65%, 70%, 75%, 80%, 85%, 90%, 95%, 96%, 97%, 98%, 99%, 99.5%, or 99.9%.

A panel may be selected to be highly specific and detect low frequency genetic variants. For instance, a panel may be selected such that a genetic variant or tumor marker present in a sample at a frequency as low as 0.01%, 0.05%, or 0.001% may be detected at a specificity of at least 50%, 55%, 60%, 65%, 70%, 75%, 80%, 85%, 90%, 95%, 96%, 97%, 98%, 99%, 99.5%, or 99.9%. Genomic locations in a panel may be selected to detect a tumor marker present at a frequency of 1% or less in a sample with a specificity of 70% or greater. A panel may be selected to detect a tumor marker at a frequency in a sample as low as 0.1% with a specificity of at least 70%, 75%, 80%, 85%, 90%, 95%, 96%, 97%, 98%, 99%, 99.5%, or 99.9%. A panel may be selected to detect a tumor marker at a frequency in a sample as low as 0.01% with a specificity of at least 70%, 75%, 80%, 85%, 90%, 95%, 96%, 97%, 98%, 99%, 99.5%, or 99.9%. A panel may be selected to detect a tumor marker at a frequency in a sample as low as 0.001% with a specificity of at least 70%, 75%, 80%, 85%, 90%, 95%, 96%, 97%, 98%, 99%, 99.5%, or 99.9%.

A panel may be selected to be highly accurate and detect low frequency genetic variants. A panel may be selected such that a genetic variant or tumor marker present in a sample at a frequency as low as 0.01%, 0.05%, or 0.001% may be detected at an accuracy of at least 70%, 75%, 80%, 85%, 90%, 95%, 96%, 97%, 98%, 99%, 99.5%, or 99.9%. Genomic locations in a panel may be selected to detect a tumor marker present at a frequency of 1% or less in a sample with an accuracy of 70% or greater. A panel may be selected to detect a tumor marker at a frequency in a sample as low as 0.1% with an accuracy of at least 70%, 75%, 80%, 85%, 90%, 95%, 96%, 97%, 98%, 99%, 99.5%, or 99.9%. A panel may be selected to detect a tumor marker at a frequency in a sample as low as 0.01% with an accuracy of at least 70%, 75%, 80%, 85%, 90%, 95%, 96%, 97%, 98%, 99%, 99.5%, or 99.9%. A panel may be selected to detect a tumor marker at a frequency in a sample as low as 0.001% with an accuracy of at least 70%, 75%, 80%, 85%, 90%, 95%, 96%, 97%, 98%, 99%, 99.5%, or 99.9%.

A panel may be selected to be highly predictive and detect low frequency genetic variants. A panel may be selected such that a genetic variant or tumor marker present in a sample at a frequency as low as 0.01%, 0.05%, or 0.001% may have a positive predictive value of at least 70%, 75%, 80%, 85%, 90%, 95%, 96%, 97%, 98%, 99%, 99.5%, or 99.9%.

The concentration of probes or baits used in the panel may be increased (2 to 6 ng/μL) to capture more nucleic acid molecule within a sample. The concentration of probes or baits used in the panel may be at least 2 ng/μL, 3 ng/μL, 4 ng/μL, 5 ng/μL, 6 ng/μL, or greater. The concentration of probes may be about 2 ng/μL to about 3 ng/μL, about 2 ng/μL to about 4 ng/μL, about 2 ng/μL to about 5 ng/μL, about 2 ng/μL to about 6 ng/μL. The concentration of probes or baits used in the panel may be 2 ng/μL or more to 6 ng/μL or less. In some instances, this may allow for more molecules within a biological to be analyzed thereby enabling lower frequency alleles to be detected.

In an implementation, after sequencing, sequence reads may be assigned a quality score. A quality score may be a representation of sequence reads that indicates whether those sequence reads may be useful in subsequent analysis based on a threshold. In some cases, some sequence reads are not of sufficient quality or length to perform a subsequent mapping step. Sequence reads with a quality score at least 90%, 95%, 99%, 99.9%, 99.99% or 99.999% may be filtered out of a data set of sequence reads. In other cases, sequence reads assigned a quality scored at least 90%, 95%, 99%, 99.9%, 99.99% or 99.999% may be filtered out of the data set. Sequence reads that meet a specified quality score threshold may be mapped to a reference genome. After mapping alignment, sequence reads may be assigned a mapping score. A mapping score may be a representation of sequence reads mapped back to the reference sequence indicating whether each position is or is not uniquely mappable. Sequence reads with a mapping score at least 90%, 95%, 99%, 99.9%, 99.99% or 99.999% may be filtered out of the data set. In other cases, sequencing reads assigned a mapping scored less than 90%, 95%, 99%, 99.9%, 99.99% or 99.999% may be filtered out of the data set.

Cancer and Other Diseases

In certain embodiments, the methods and aspects disclosed herein are used to diagnose a given disease, disorder or condition in patients. In certain embodiments, the methods and aspects disclosed herein are used in longitudinal monitoring of patients and tracking treatment response of a subject having a disease. Typically, the disease under consideration is a type of cancer. Non-limiting examples of such cancers include biliary tract cancer, bladder cancer, transitional cell carcinoma, urothelial carcinoma, brain cancer, gliomas, astrocytomas, breast carcinoma, metaplastic carcinoma, cervical cancer, cervical squamous cell carcinoma, rectal cancer, colorectal carcinoma, colon cancer, hereditary nonpolyposis colorectal cancer, colorectal adenocarcinomas, gastrointestinal stromal tumors (GISTs), endometrial carcinoma, endometrial stromal sarcomas, esophageal cancer, esophageal squamous cell carcinoma, esophageal adenocarcinoma, ocular melanoma, uveal melanoma, gallbladder carcinomas, gallbladder adenocarcinoma, renal cell carcinoma, clear cell renal cell carcinoma, transitional cell carcinoma, urothelial carcinomas, Wilms tumor, leukemia, acute lymphocytic leukemia (ALL), acute myeloid leukemia (AML), chronic lymphocytic (CLL), chronic myeloid (CML), chronic myelomonocytic (CMML), liver cancer, liver carcinoma, hepatoma, hepatocellular carcinoma, cholangiocarcinoma, hepatoblastoma, Lung cancer, non-small cell lung cancer (NSCLC), mesothelioma, B-cell lymphomas, non-Hodgkin lymphoma, diffuse large B-cell lymphoma, Mantle cell lymphoma, T cell lymphomas, non-Hodgkin lymphoma, precursor T-lymphoblastic lymphoma/leukemia, peripheral T cell lymphomas, multiple myeloma, nasopharyngeal carcinoma (NPC), neuroblastoma, oropharyngeal cancer, oral cavity squamous cell carcinomas, osteosarcoma, ovarian carcinoma, pancreatic cancer, pancreatic ductal adenocarcinoma, pseudopapillary neoplasms, acinar cell carcinomas. Prostate cancer, prostate adenocarcinoma, skin cancer, melanoma, malignant melanoma, cutaneous melanoma, small intestine carcinomas, stomach cancer, gastric carcinoma, gastrointestinal stromal tumor (GIST), uterine cancer, or uterine sarcoma.

Non-limiting examples of other genetic-based diseases, disorders, or conditions that are optionally evaluated using the methods and systems disclosed herein include achondroplasia, alpha-1 antitrypsin deficiency, antiphospholipid syndrome, autism, autosomal dominant polycystic kidney disease, Charcot-Marie-Tooth (CMT), cri du chat, Crohn's disease, cystic fibrosis, Dercum disease, down syndrome, Duane syndrome, Duchenne muscular dystrophy, Factor V Leiden thrombophilia, familial hypercholesterolemia, familial mediterranean fever, fragile X syndrome, Gaucher disease, hemochromatosis, hemophilia, holoprosencephaly, Huntington's disease, Klinefelter syndrome, Marfan syndrome, myotonic dystrophy, neurofibromatosis, Noonan syndrome, osteogenesis imperfecta, Parkinson's disease, phenylketonuria, Poland anomaly, porphyria, progeria, retinitis pigmentosa, severe combined immunodeficiency (scid), sickle cell disease, spinal muscular atrophy, Tay-Sachs, thalassemia, trimethylaminuria, Turner syndrome, velocardiofacial syndrome, WAGR syndrome, Wilson disease, or the like.

Precision Treatments

The precision diagnostics provided by the improved computer system 110 may result in precision treatment plans, which may be identified by the computer system 110 (and/or curated by health professionals). For example, one type of precision diagnostic and treatment may relate to genes in the homologous recombination repair (HRR) pathway.

Homologous recombination is a type of genetic recombination in which nucleotide sequences are exchanged between two similar or identical molecules of DNA. It is most widely used by cells to accurately repair harmful breaks that occur on both strands of DNA, known as double-strand breaks (DSB). HRR provides a mechanism for the error-free removal of damage present in DNA that has replicated (S and G2 phases), to eliminate chromosomal breaks before the cell division occurs. The primary model for how homologous recombination repairs double-strand breaks in DNA is homologous recombination repair pathway which mediates the double-strand break repair (DSBR) pathway and the synthesis-dependent strand annealing (SDSA) pathway. Germline and somatic deficiencies in homologous recombination genes have been strongly linked to breast, ovarian and prostate cancers.

The number and types of variant nucleotides in a sample can provide an indication of the amenability of the subject providing the sample to treatment, i.e., therapeutic intervention. For example, various poly ADP ribose polymerase (PARP) inhibitors have been shown to stop the growth of tumors from breast, ovarian and prostate cancers caused by hereditary mutations in the BRCA1 or BRCA2 genes. Some of these therapeutic agents may inhibit base excision repair (BER), which may compensate for the deficiency of HRR.

On the other hand, certain BRCA and HRR wildtype patients may not achieve clinical benefit from treatment with a PARP inhibitor. Furthermore, not all ovarian cancer patients with a BRCA mutation will respond to a PARP inhibitor. Moreover, different types of mutations may indicate different therapies. For example, somatic heterozygous deletions in HRR genes may indicate a different therapy than somatic homozygous deletions. Thus, the state of genetic material may influence therapy. In one example, a PARP inhibitor may be administered to an individual harboring a somatic homozygous deletion in a HRR gene, but not to an individual harboring a wildtype allele or somatic heterozygous deletions in the HRR gene.

In some implementations, a subject having HRD as determined by any of the methods disclosed may be administered a targeted therapy. The targeted therapy may comprise a PARP inhibitor. Examples of PARP inhibitors that may be administered include one or more of: VELIPARIB, OLAPARIB, TALAZOPARIB, RUCAPARIB, NIRAPARIB, PAMIPARIB, CEP 9722 (Cephalon), E7016 (Eisai), E7449 (Eisai, a PARP 1/2 and tankyrase 1/2 inhibitor), or 3-Aminobenzamide. In some implementations, the targeted therapy may comprise at least one base excision repair (BER) inhibitor. For example, OLAPARIB may inhibit BER. In certain implementations, the targeted therapy may comprise combination of a PARP inhibitor and radiotherapy. In an implementation, the combination of a PARP inhibitor and radiotherapy would permit the PARP inhibitor to lead to formation of double strand breaks from the single-strand breaks generated by the radiotherapy in tumor tissue (e.g., tissue with BRCA1/BRCA2 mutations). This combination can provide more powerful therapy per radiation dose.

Customized Therapies and Related Administrations

In some implementations, the methods disclosed herein relate to identifying and administering therapies to patients having a given disease, disorder or condition. Essentially any cancer therapy (e.g., surgical therapy, radiation therapy, chemotherapy, and/or the like) is included as part of these methods. In certain implementations, the therapy administered to a subject may comprise at least one chemotherapy drug. In some implementations, the chemotherapy drug may comprise alkylating agents (for example, but not limited to, Chlorambucil, Cyclophosphamide, Cisplatin and Carboplatin), nitrosoureas (for example, but not limited to, Carmustine and Lomustine), anti-metabolites (for example, but not limited to, Fluorauracil, Methotrexate and Fludarabine), plant alkaloids and natural products (for example, but not limited to, Vincristine, Paclitaxel and Topotecan), anti-tumor antibiotics (for example, but not limited to, Bleomycin, Doxorubicin and Mitoxantrone), hormonal agents (for example, but not limited to, Prednisone, Dexamethasone, Tamoxifen and Leuprolide) and biological response modifiers (for example, but not limited to, Herceptin and Avastin, Erbitux and Rituxan). In some implementations, the chemotherapy administered to a subject may comprise FOLFOX or FOLFIRI. Typically, therapies include at least one immunotherapy (or an immunotherapeutic agent). Immunotherapy refers generally to methods of enhancing an immune response against a given cancer type. In certain implementations, immunotherapy refers to methods of enhancing a T cell response against a tumor or cancer.

In some implementations, the immunotherapy or immunotherapeutic agents targets an immune checkpoint molecule. Certain tumors are able to evade the immune system by co-opting an immune checkpoint pathway. Thus, targeting immune checkpoints has emerged as an effective approach for countering a tumor's ability to evade the immune system and activating anti-tumor immunity against certain cancers. Pardoll, Nature Reviews Cancer, 2012, 12:252-264.

In certain implementations, the immune checkpoint molecule is an inhibitory molecule that reduces a signal involved in the T cell response to antigen. For example, CTLA4 is expressed on T cells and plays a role in downregulating T cell activation by binding to CD80 (aka B7.1) or CD86 (aka B7.2) on antigen presenting cells. PD-1 is another inhibitory checkpoint molecule that is expressed on T cells. PD-1 limits the activity of T cells in peripheral tissues during an inflammatory response. In addition, the ligand for PD-1 (PD-L1 or PD-L2) is commonly upregulated on the surface of many different tumors, resulting in the downregulation of anti-tumor immune responses in the tumor microenvironment. In certain implementations, the inhibitory immune checkpoint molecule is CTLA4 or PD-1. In other implementations, the inhibitory immune checkpoint molecule is a ligand for PD-1, such as PD-L1 or PD-L2. In other implementations, the inhibitory immune checkpoint molecule is a ligand for CTLA4, such as CD80 or CD86. In other implementations, the inhibitory immune checkpoint molecule is lymphocyte activation gene 3 (LAG3), killer cell immunoglobulin like receptor (KIR), T cell membrane protein 3 (TIM3), galectin 9 (GAL9), or adenosine A2a receptor (A2aR).

Antagonists that target these immune checkpoint molecules can be used to enhance antigen-specific T cell responses against certain cancers. Accordingly, in certain implementations, the immunotherapy or immunotherapeutic agent is an antagonist of an inhibitory immune checkpoint molecule. In certain implementations, the inhibitory immune checkpoint molecule is PD-1. In certain implementations, the inhibitory immune checkpoint molecule is PD-L1. In certain implementations, the antagonist of the inhibitory immune checkpoint molecule is an antibody (e.g., a monoclonal antibody). In certain implementations, the antibody or monoclonal antibody is an anti-CTLA4, anti-PD-1, anti-PD-L1, or anti-PD-L2 antibody. In certain implementations, the antibody is a monoclonal anti-PD-1 antibody. In some implementations, the antibody is a monoclonal anti-PD-L1 antibody. In certain implementations, the monoclonal antibody is a combination of an anti-CTLA4 antibody and an anti-PD-1 antibody, an anti-CTLA4 antibody and an anti-PD-L1 antibody, or an anti-PD-L1 antibody and an anti-PD-1 antibody. In certain implementations, the anti-PD-1 antibody is one or more of pembrolizumab (Keytruda®) or nivolumab (Opdivo®). In certain implementations, the anti-CTLA4 antibody is ipilimumab (Yervoy®). In certain implementations, the anti-PD-L1 antibody is one or more of atezolizumab (Tecentriq®), avelumab (Bavencio®), or durvalumab (Imfinzi®).

In certain implementations, the immunotherapy or immunotherapeutic agent is an antagonist (e.g. antibody) against CD80, CD86, LAG3, KIR, TIM3, GAL9, or A2aR. In other implementations, the antagonist is a soluble version of the inhibitory immune checkpoint molecule, such as a soluble fusion protein comprising the extracellular domain of the inhibitory immune checkpoint molecule and an Fc domain of an antibody. In certain implementations, the soluble fusion protein comprises the extracellular domain of CTLA4, PD-1, PD-L1, or PD-L2. In some implementations, the soluble fusion protein comprises the extracellular domain of CD80, CD86, LAG3, KIR, TIM3, GAL9, or A2aR. In one implementation, the soluble fusion protein comprises the extracellular domain of PD-L2 or LAG3.

In certain implementations, the immune checkpoint molecule is a co-stimulatory molecule that amplifies a signal involved in a T cell response to an antigen. For example, CD28 is a co-stimulatory receptor expressed on T cells. When a T cell binds to antigen through its T cell receptor, CD28 binds to CD80 (aka B7.1) or CD86 (aka B7.2) on antigen-presenting cells to amplify T cell receptor signaling and promote T cell activation. Because CD28 binds to the same ligands (CD80 and CD86) as CTLA4, CTLA4 is able to counteract or regulate the co-stimulatory signaling mediated by CD28. In certain implementations, the immune checkpoint molecule is a co-stimulatory molecule selected from CD28, inducible T cell co-stimulator (ICOS), CD137, OX40, or CD27. In other implementations, the immune checkpoint molecule is a ligand of a co-stimulatory molecule, including, for example, CD80, CD86, B7RP1, B7-H3, B7-H4, CD137L, OX40L, or CD70.

Agonists that target these co-stimulatory checkpoint molecules can be used to enhance antigen-specific T cell responses against certain cancers. Accordingly, in certain implementations, the immunotherapy or immunotherapeutic agent is an agonist of a co-stimulatory checkpoint molecule. In certain implementations, the agonist of the co-stimulatory checkpoint molecule is an agonist antibody and preferably is a monoclonal antibody. In certain implementations, the agonist antibody or monoclonal antibody is an anti-CD28 antibody. In other implementations, the agonist antibody or monoclonal antibody is an anti-ICOS, anti-CD137, anti-OX40, or anti-CD27 antibody. In other implementations, the agonist antibody or monoclonal antibody is an anti-CD80, anti-CD86, anti-B7RP1, anti-B7-H3, anti-B7-H4, anti-CD137L, anti-OX40L, or anti-CD70 antibody.

Therapeutic options for treating specific genetic-based diseases, disorders, or conditions, other than cancer, are generally well-known to those of ordinary skill in the art and will be apparent given the particular disease, disorder, or condition under consideration.

In certain implementations, the customized therapies described herein are typically administered parenterally (e.g., intravenously or subcutaneously). Pharmaceutical compositions containing the immunotherapeutic agent are typically administered intravenously. Certain therapeutic agents are administered orally. However, customized therapies (e.g., immunotherapeutic agents, etc.) may also be administered by any method known in the art, including, for example, buccal, sublingual, rectal, vaginal, intraurethral, topical, intraocular, intranasal, and/or intraauricular, which administration may include tablets, capsules, granules, aqueous suspensions, gels, sprays, suppositories, salves, ointments, or the like.

Figure 11:
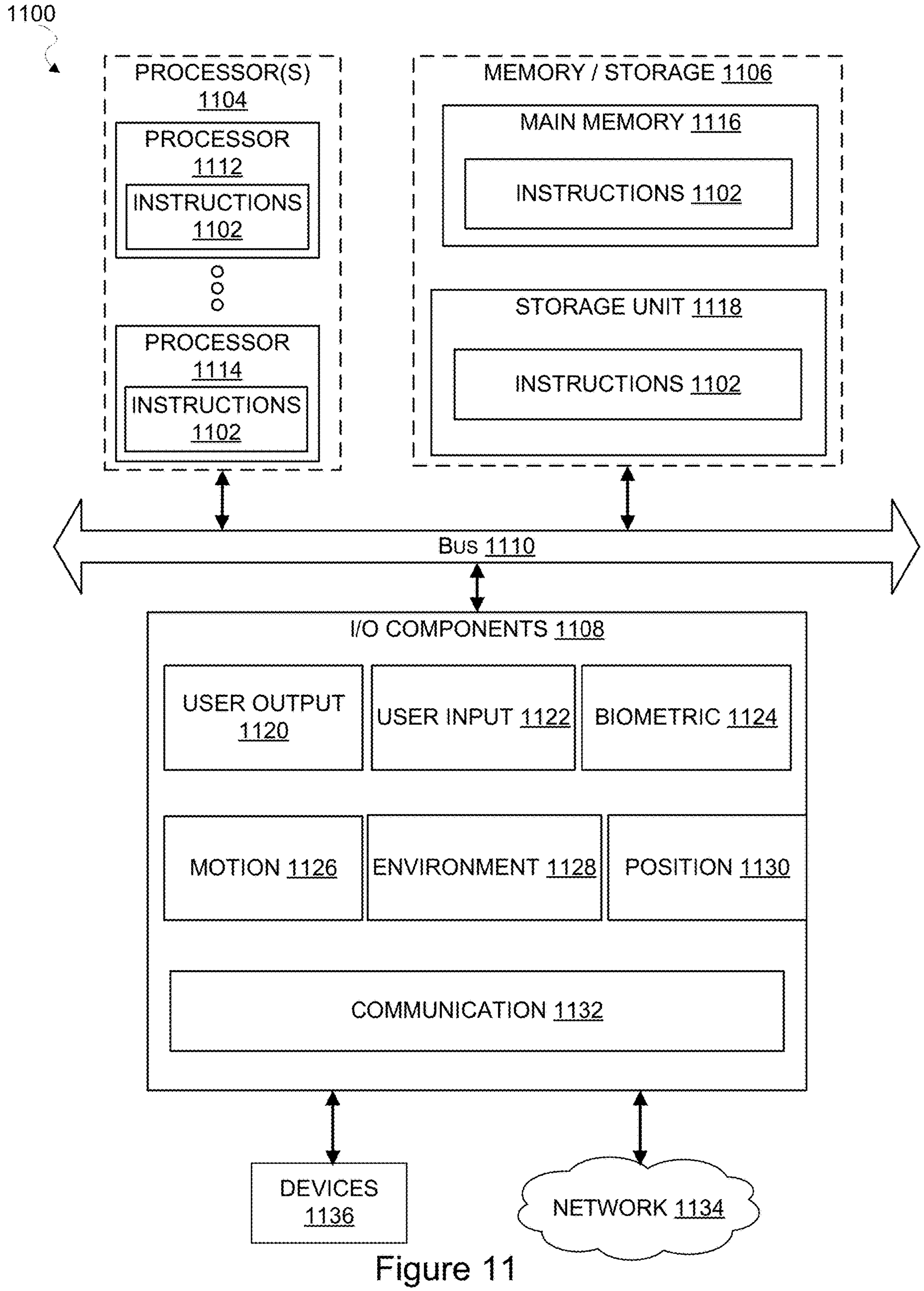
FIG. 11 is a block diagram illustrating components of a machine, in the form of a computer system, that may read and execute instructions from one or more machine-readable media to perform any one or more methodologies described herein, in accordance with one or more example implementations.

FIG. 11 is a block diagram illustrating components of a machine 1100, according to some example implementations, able to read instructions from a machine-readable medium (e.g., a machine-readable storage medium) and perform any one or more of the methodologies discussed herein. Specifically, FIG. 11 shows a diagrammatic representation of the machine 1100 in the example form of a computer system, within which instructions 1102 (e.g., software, a program, an application, an applet, an app, or other executable code) for causing the machine 1100 to perform any one or more of the methodologies discussed herein may be executed. As such, the instructions 1102 may be used to implement modules or components described herein. The instructions 1102 transform the general, non-programmed machine 1100 into a particular machine 1100 programmed to carry out the described and illustrated functions in the manner described. In alternative implementations, the machine 1100 operates as a standalone device or may be coupled (e.g., networked) to other machines. In a networked deployment, the machine 1100 may operate in the capacity of a server machine or a client machine in a server-client network environment, or as a peer machine in a peer-to-peer (or distributed) network environment. The machine 1100 may comprise, but not be limited to, a server computer, a client computer, a personal computer (PC), a tablet computer, a laptop computer, a netbook, a set-top box (STB), a personal digital assistant (PDA), an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 1102, sequentially or otherwise, that specify actions to be taken by machine 1100. Further, while only a single machine 1100 is illustrated, the term "machine" shall also be taken to include a collection of machines that individually or jointly execute the instructions 1102 to perform any one or more of the methodologies discussed herein.

The machine 1100 may include processors 1104, memory/storage 1106, and I/O components 1108 components 1108, which may be configured to communicate with each other such as via a bus 1110. In an example implementation, the processors 1104 (e.g., a central processing unit (CPU), a reduced instruction set computing (RISC) processor, a complex instruction set computing (CISC) processor, a graphics processing unit (GPU), a digital signal processor (DSP), an application-specific integrated circuit (ASIC), a radio-frequency integrated circuit (RFIC), another processor, or any suitable combination thereof) may include, for example, a processor 1112 and a processor 1114 that may execute the instructions 1102. The term "processor" is intended to include multi-core processors 1104 that may comprise two or more independent processors (sometimes referred to as "cores") that may execute instructions 1102 contemporaneously. Although FIG. 11 shows multiple processors 1104, the machine 1100 may include a single processor 1112 processor 1112 with a single core, a single processor 1112 processor 1112 with multiple cores (e.g., a multi-core processor), multiple processors 1112, 1114 with a single core, multiple processors 1112, 1114 with multiple cores, or any combination thereof.

The memory/storage 1106 may include memory, such as a main memory 1116, or other memory storage, and a storage unit 1118, both accessible to the processors 1104 such as via the bus 1110. The storage unit 1118 and main memory 1116 store the instructions 1102 embodying any one or more of the methodologies or functions described herein. The instructions 1102 may also reside, completely or partially, within the main memory 1116, within the storage unit 1118, within at least one of the processors 1104 (e.g., within the processor's cache memory), or any suitable combination thereof, during execution thereof by the machine 1100. Accordingly, the main memory 1116, the storage unit 1118, and the memory of processors 1104 are examples of machine-readable media.

The I/O components 1108 components 1108 may include a wide variety of components to receive input, provide output, produce output, transmit information, exchange information, capture measurements, and so on. The specific I/O components 1108 components 1108 that are included in a particular machine 1100 will depend on the type of machine. For example, portable machines such as mobile phones will likely include a touch input device or other such input mechanisms, while a headless server machine will likely not include such a touch input device. It will be appreciated that the I/O components 1108 components 1108 may include many other components that are not shown in FIG. 10. The I/O components 1108 components 1108 are grouped according to functionality merely for simplifying the following discussion and the grouping is in no way limiting. In various example implementations, the I/O components 1108 components 1108 may include user output components 1120 and user input components 1122. The user output components 1120 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The user input components 1122 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or other pointing instrument), tactile input components (e.g., a physical button, a touch screen that provides location or force of touches or touch gestures, or other tactile input components), audio input components (e.g., a microphone), and the like.

In further example implementations, the I/O components 1108 components 1108 may include biometric components 1124, motion components 1126, environmental components 1128, or position components 1130 among a wide array of other components. For example, the biometric components 1124 may include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram based identification), and the like. The motion components 1126 may include acceleration sensor components (e.g., accelerometer), gravitation sensor components, rotation sensor components (e.g., gyroscope), and so forth. The environmental components 1128 may include, for example, illumination sensor components (e.g., photometer), temperature sensor components (e.g., one or more thermometer that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 1130 may include location sensor components (e.g., a GPS receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 1108 components 1108 may include communication components 1132 operable to couple the machine 1100 to a network 1134 or devices 1136. For example, the communication components 1132 may include a network interface component or other suitable device to interface with the network 1134. In further examples, communication components 1132 may include wired communication components, wireless communication components, cellular communication components, near field communication (NFC) components, Bluetooth® components (e.g., Bluetooth® Low Energy), Wi-Fi® components, and other communication components to provide communication via other modalities. The devices 1136 may be another machine 1100 or any of a wide variety of peripheral devices (e.g., a peripheral device coupled via a USB).

Moreover, the communication components 1132 may detect identifiers or include components operable to detect identifiers. For example, the communication components 1132 may include radio frequency identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 1132, such as location via Internet Protocol (IP) geo-location, location via Wi-Fi® signal triangulation, location via detecting an NFC beacon signal that may indicate a particular location, and so forth.

As used herein, "component" refers to a device, physical entity, or logic having boundaries defined by function or subroutine calls, branch points, APIs, or other technologies that provide for the partitioning or modularization of particular processing or control functions. Components may be combined via their interfaces with other components to carry out a machine process. A component may be a packaged functional hardware unit designed for use with other components and a part of a program that usually performs a particular function of related functions. Components may constitute either software components (e.g., code embodied on a machine-readable medium) or hardware components. A "hardware component" is a tangible unit capable of performing certain operations and may be configured or arranged in a certain physical manner. In various example implementations, one or more computer systems (e.g., a standalone computer system, a client computer system, or a server computer system) or one or more hardware components of a computer system (e.g., a processor or a group of processors) may be configured by software (e.g., an application or application portion) as a hardware component that operates to perform certain operations as described herein.

A hardware component may also be implemented mechanically, electronically, or any suitable combination thereof. For example, a hardware component may include dedicated circuitry or logic that is permanently configured to perform certain operations. A hardware component may be a special-purpose processor, such as a field-programmable gate array (FPGA) or an ASIC. A hardware component may also include programmable logic or circuitry that is temporarily configured by software to perform certain operations. For example, a hardware component may include software executed by a general-purpose processor 1104 or other programmable processor. Once configured by such software, hardware components become specific machines (or specific components of a machine 1100) uniquely tailored to perform the configured functions and are no longer general-purpose processors 1104. It will be appreciated that the decision to implement a hardware component mechanically, in dedicated and permanently configured circuitry, or in temporarily configured circuitry (e.g., configured by software) may be driven by cost and time considerations. Accordingly, the phrase "hardware component" (or "hardware-implemented component") should be understood to encompass a tangible entity, be that an entity that is physically constructed, permanently configured (e.g., hardwired), or temporarily configured (e.g., programmed) to operate in a certain manner or to perform certain operations described herein. Considering implementations in which hardware components are temporarily configured (e.g., programmed), each of the hardware components need not be configured or instantiated at any one instance in time. For example, where a hardware component comprises a general-purpose processor 1104 configured by software to become a special-purpose processor, the general-purpose processor 1104 may be configured as respectively different special-purpose processors (e.g., comprising different hardware components) at different times. Software accordingly configures a particular processor 1112 processor 1112, 1114 or processors 1104, for example, to constitute a particular hardware component at one instance of time and to constitute a different hardware component at a different instance of time.

Hardware components can provide information to, and receive information from, other hardware components. Accordingly, the described hardware components may be regarded as being communicatively coupled. Where multiple hardware components exist contemporaneously, communications may be achieved through signal transmission (e.g., over appropriate circuits and buses) between or among two or more of the hardware components. In implementations in which multiple hardware components are configured or instantiated at different times, communications between such hardware components may be achieved, for example, through the storage and retrieval of information in memory structures to which the multiple hardware components have access. For example, one hardware component may perform an operation and store the output of that operation in a memory device to which it is communicatively coupled. A further hardware component may then, at a later time, access the memory device to retrieve and process the stored output.

Hardware components may also initiate communications with input or output devices, and can operate on a resource (e.g., a collection of information). The various operations of example methods described herein may be performed, at least partially, by one or more processors 1104 that are temporarily configured (e.g., by software) or permanently configured to perform the relevant operations. Whether temporarily or permanently configured, such processors 1104 may constitute processor-implemented components that operate to perform one or more operations or functions described herein. As used herein, "processor-implemented component" refers to a hardware component implemented using one or more processors 1104. Similarly, the methods described herein may be at least partially processor-implemented, with a particular processor 1112 processor 1112, 1114 or processors 1104 being an example of hardware. For example, at least some of the operations of a method may be performed by one or more processors 1104 or processor-implemented components. Moreover, the one or more processors 1104 may also operate to support performance of the relevant operations in a "cloud computing" environment or as a "software as a service" (SaaS). For example, at least some of the operations may be performed by a group of computers (as examples of machines 1000 including processors 1104), with these operations being accessible via a network 1134 (e.g., the Internet) and via one or more appropriate interfaces (e.g., an API). The performance of certain of the operations may be distributed among the processors, not only residing within a single machine 1100, but deployed across a number of machines. In some example implementations, the processors 1104 or processor-implemented components may be located in a single geographic location (e.g., within a home environment, an office environment, or a server farm). In other example implementations, the processors 1104 or processor-implemented components may be distributed across a number of geographic locations.

Figure 12:
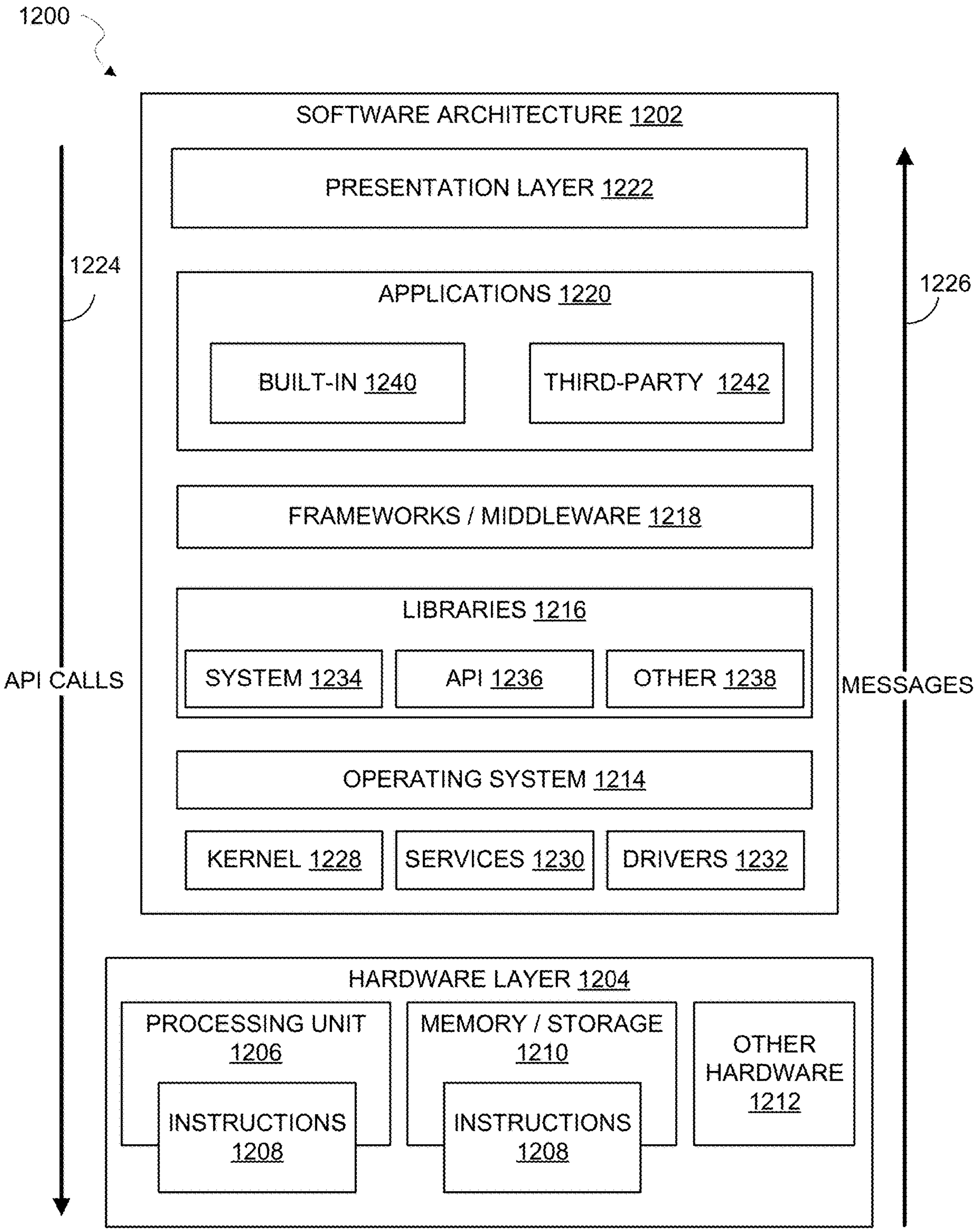
FIG. 12 is a block diagram illustrating a representative software architecture that may be used in conjunction with one or more hardware architectures described herein, in accordance with one or more example implementations.

FIG. 12 is a block diagram illustrating system 1200 that includes an example software architecture 1202, which may be used in conjunction with various hardware architectures herein described. FIG. 12 is a non-limiting example of a software architecture and it will be appreciated that many other architectures may be implemented to facilitate the functionality described herein. The software architecture 1202 may execute on hardware such as machine 1100 of FIG. 11 that includes, among other things, processors 1104, memory/storage 1106, and input/output (I/O) components 1108. A representative hardware layer 1204 is illustrated and can represent, for example, the machine 1100 of FIG. 11. The representative hardware layer 1204 includes a processing unit 1206 having associated executable instructions 1208. Executable instructions 1208 represent the executable instructions of the software architecture 1202, including implementation of the methods, components, and so forth described herein. The hardware layer 1204 also includes at least one of memory or storage modules memory/storage 1210, which also have executable instructions 1208. The hardware layer 1204 may also comprise other hardware 1212.

In the example architecture of FIG. 12, the software architecture 1202 may be conceptualized as a stack of layers where each layer provides particular functionality. For example, the software architecture 1202 may include layers such as an operating system 1214, libraries 1216, frameworks/middleware 1218, applications 1220, and a presentation layer 1222. Operationally, the applications 1220 or other components within the layers may invoke API calls 1224 through the software stack and receive messages 1226 in response to the API calls 1224. The layers illustrated are representative in nature and not all software architectures have all layers. For example, some mobile or special purpose operating systems may not provide a frameworks/middleware 1218, while others may provide such a layer. Other software architectures may include additional or different layers.

The operating system 1214 may manage hardware resources and provide common services. The operating system 1214 may include, for example, a kernel 1228, services 1230, and drivers 1232. The kernel 1228 may act as an abstraction layer between the hardware and the other software layers. For example, the kernel 1228 may be responsible for memory management, processor management (e.g., scheduling), component management, networking, security settings, and so on. The services 1230 may provide other common services for the other software layers. The drivers 1232 are responsible for controlling or interfacing with the underlying hardware. For instance, the drivers 1232 include display drivers, camera drivers, Bluetooth® drivers, flash memory drivers, serial communication drivers (e.g., Universal Serial Bus (USB) drivers), Wi-Fi® drivers, audio drivers, power management drivers, and so forth depending on the hardware configuration.

The libraries 1216 provide a common infrastructure that is used by at least one of the applications 1220, other components, or layers. The libraries 1216 provide functionality that allows other software components to perform tasks in an easier fashion than to interface directly with the underlying operating system 1214 functionality (e.g., kernel 1228, services 1230, drivers 1232). The libraries 1216 may include system libraries 1234 (e.g., C standard library) that may provide functions such as memory allocation functions, string manipulation functions, mathematical functions, and the like. In addition, the libraries 1216 may include API libraries 1236 such as media libraries (e.g., libraries to support presentation and manipulation of various media format such as MPEG4, H.264, MP3, AAC, AMR, JPG, PNG), graphics libraries (e.g., an OpenGL framework that may be used to render two-dimensional and three-dimensional in a graphic content on a display), database libraries (e.g., SQLite that may provide various relational database functions), web libraries (e.g., WebKit that may provide web browsing functionality), and the like. The libraries 1216 may also include a wide variety of other libraries 1238 to provide many other APIs to the applications 1220 and other software components/modules.

The frameworks/middleware 1218 (also sometimes referred to as middleware) provide a higher-level common infrastructure that may be used by the applications 1220 or other software components/modules. For example, the frameworks/middleware 1218 may provide various graphical user interface functions, high-level resource management, high-level location services, and so forth. The frameworks/middleware 1218 may provide a broad spectrum of other APIs that may be utilized by the applications 1220 or other software components/modules, some of which may be specific to a particular operating system 1214 or platform.

The applications 1220 include built-in applications 1240 and third-party applications 1242. Examples of representative built-in applications 1240 may include, but are not limited to, a contacts application, a browser application, a book reader application, a location application, a media application, a messaging application, or a game application. Third-party applications 1242 may include an application developed using the ANDROID™ or IOS™ software development kit (SDK) by an entity other than the vendor of the particular platform, and may be mobile software running on a mobile operating system such as IOS™, ANDROID™, WINDOWS® Phone, or other mobile operating systems. The third-party applications 1242 may invoke the API calls 1224 provided by the mobile operating system (such as operating system 1214) to facilitate functionality described herein.

The applications 1220 may use built-in operating system functions (e.g., kernel 1228, services 1230, drivers 1232), libraries 1216, and frameworks/middleware 1218 to create UIs to interact with users of the system. Alternatively, or additionally, in some systems, interactions with a user may occur through a presentation layer, such as presentation layer 1222. In these systems, the application/component "logic" can be separated from the aspects of the application/component that interact with a user.

At least some of the processes described herein can be embodied in computer-readable instructions for execution by one or more processors such that the operations of the processes may be performed in part or in whole by the functional components of one or more computer systems. Accordingly, computer-implemented processes described herein are by way of example with reference thereto, in some situations. However, in other implementations, at least some of the operations of the computer-implemented processes described herein can be deployed on various other hardware configurations. The computer-implemented processes described herein are therefore not intended to be limited to the systems and configurations described with respect to FIGS. 11 and 12 and can be implemented in whole, or in part, by one or more additional system and/or components.

Although the flowcharts described herein can show operations as a sequential process, many of the operations can be performed in parallel or concurrently. In addition, the order of the operations can be re-arranged. A process is terminated when its operations are completed. A process can correspond to a method, a procedure, an algorithm, etc. The operations of methods may be performed in whole or in part, can be performed in conjunction with some or all of the operations in other methods, and can be performed by any number of different systems, such as the systems described herein, or any portion thereof, such as a processor included in any of the systems.

EXAMPLES

Example 1

Systematic coverage biases were mitigated utilizing a probabilistic model to simultaneously normalize molecular coverage of both targeted and off-target genomic regions. The model was informed by sequencing data from a large database of more than 100 k clinical cell-free DNA (cfDNA) patient samples (Guardant Health, CA).

Segmented regions of consistent copy number were identified utilizing Circular Binary Segmentation. A probabilistic model that incorporated the coverage of on/off target regions and allele frequency of germline SNPs within each segment was fit using an EM algorithm. The composite probabilistic model allows for the prediction of gene level somatic CNAs, genes loss of function or genome wide instability/LoH.

Datasets with deletions and amplifications of regions of size 40 Mb, using coverage and mutant allele fraction (MAF) variability observed in existing data were simulated. The existing data was obtained from results of liquid biopsies. The simulation study compared the sensitivity in detection of small levels of amplifications and deletions (1-4 copies) in order to compare "on+off target" model to "on-target" only model performance. FIG. 13A shows differences in limits of detection (LoD) for loss of heterozygosity in situations where the copy number is "3" when an amplification occurs or "1" when a deletion has occurred using on-target data only in relation to using a combination of on-target and off-target data for 40 Mb size regions. The sensitivity can be improved in these situations by at least about 20% when both on-target and off-target data is used in relation to the use of on-target data only.

Figure 13B:
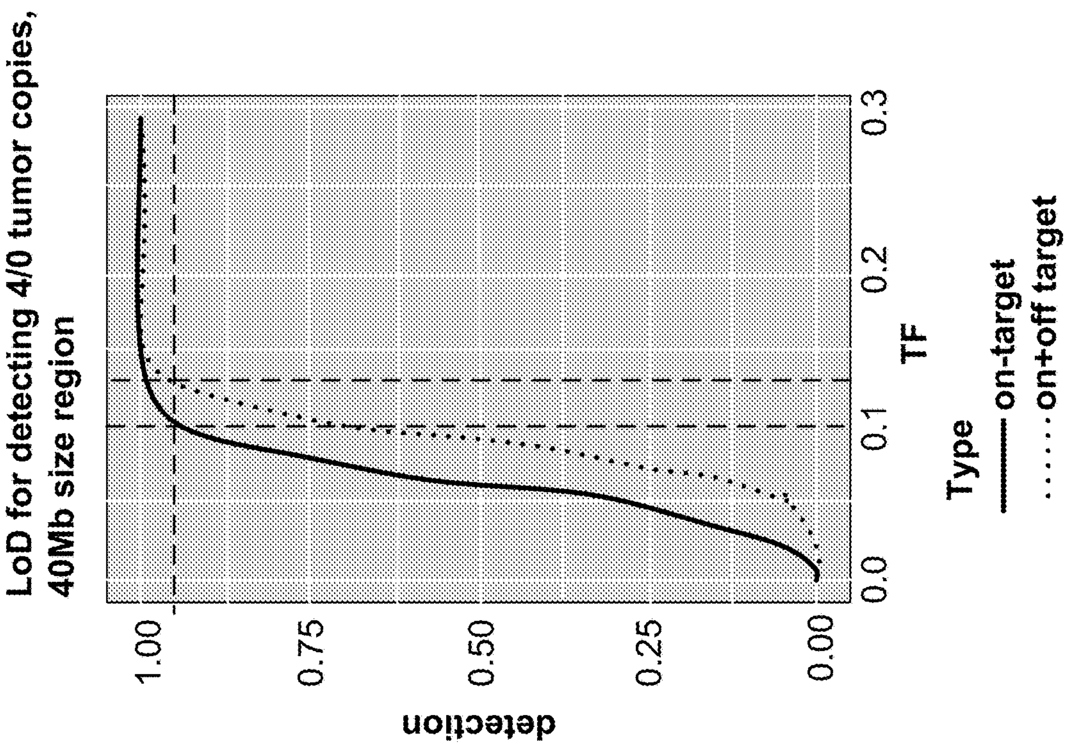
FIG. 13B shows differences in LoD for loss of heterozygosity in situations where the copy number is "4" when an amplification occurs or "0" copies for homozygous deletion using on-target data only in relation to using a combination of on-target and off-target data for 40 Mb size regions.
Figure 13A:
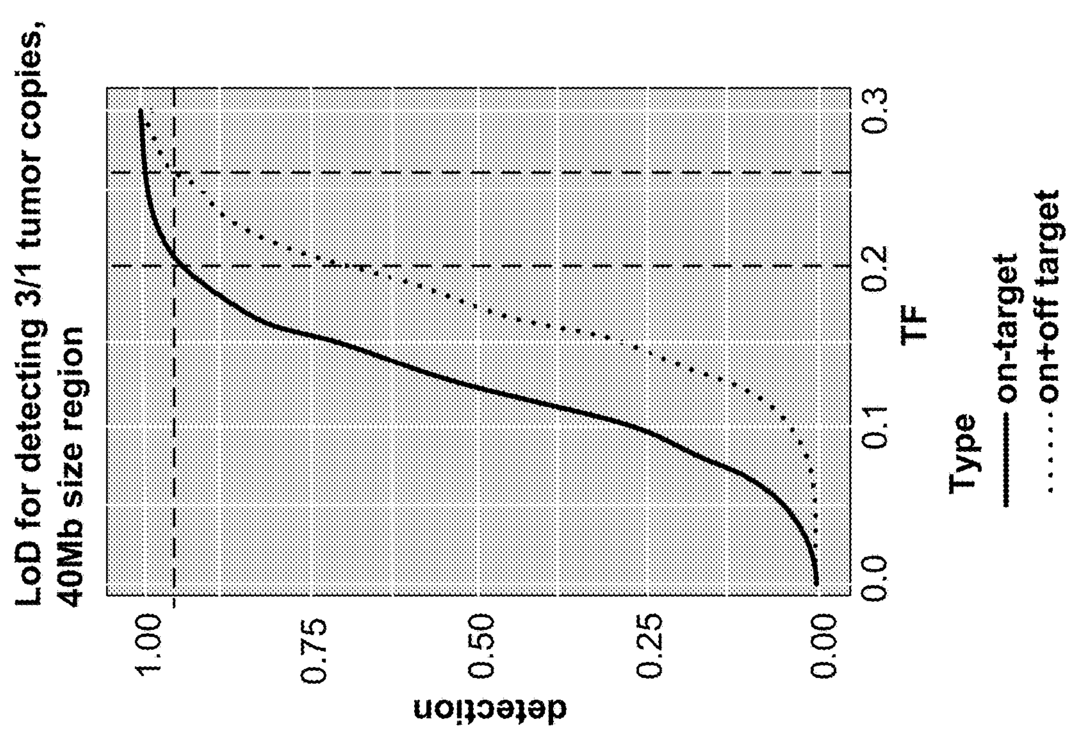
FIG. 13A shows differences in limits of detection (LoD) for loss of heterozygosity in situations where the copy number is “3” when an amplification occurs or “1” when a deletion has occurred using on-target data only in relation to using a combination of on-target and off-target data for 40 Mb size regions. The sensitivity can be improved in these situations by at least about 20% when both on-target and off-target data is used in relation to the use of on-target data only.

FIG. 13B shows differences in LoD for loss of heterozygosity in situations where the copy number is "4" when an amplification occurs or "0" copies for homozygous deletion using on-target data only in relation to using a combination of on-target and off-target data for 40 Mb size regions. The sensitivity can be improved in these situations by at least about 10% when both on-target and off-target data is used in relation to the use of on-target data only. LoD in detection of LOH/3 copies or homdel/4 copies for 40 Mb size regions. Note: sensitivity in detection of copy number alteration is a function not only of tumor cells copy number but also of the size of the altered genomic region and becomes less dependent on the targeting panel.

Example 2

Figure 14:
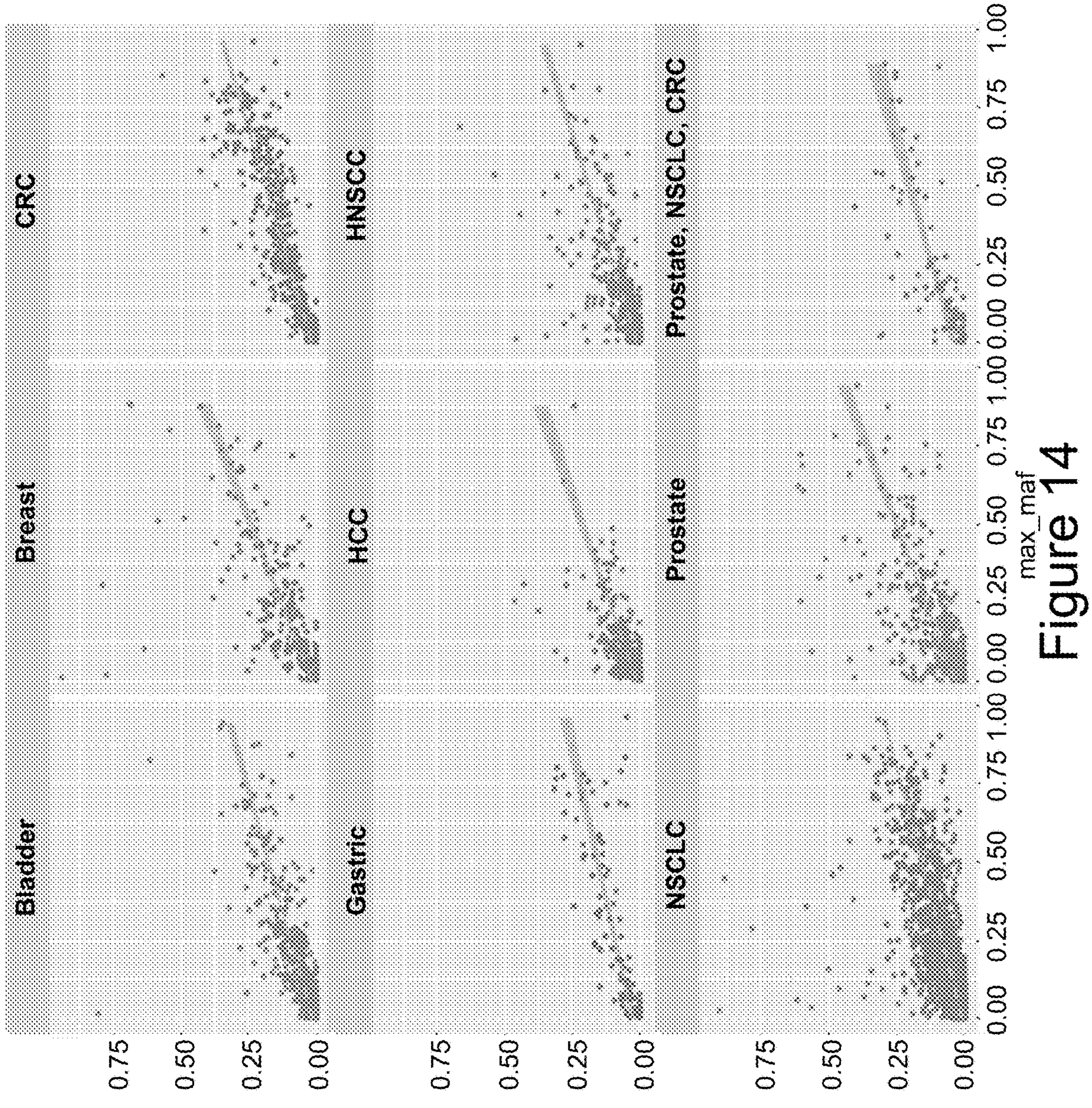
FIG. 14 shows plots of maximum mutant allele fraction (MAF) in relation to tumor fraction for different types of cancer.

FIG. 14 shows plots of maximum mutant allele fraction (MAF) in relation to predicted tumor fraction for different types of cancer. The predicted tumor fraction is based on techniques described herein that use a maximum likelihood estimation (MLE) model with tissue copy numbers for genomic segments being parameters for the MLE model. High concordance was observed in cancer types for which drivers are frequently included in the panel. CRC samples ($R^2$=0.75), gastric cancer ($R^2$=0.63) and bladder cancer ($R^2$=0.6), suggest the use of this metric to better estimate tumor shedding levels in cfDNA in cases when driver mutations are not represented on a targeting panel. Analyses included >6,000 cancer samples of various cancer types, for which the somatic call with the highest allele fraction is a known driver mutation for the given cancer type.

Example 3

Figure 15:
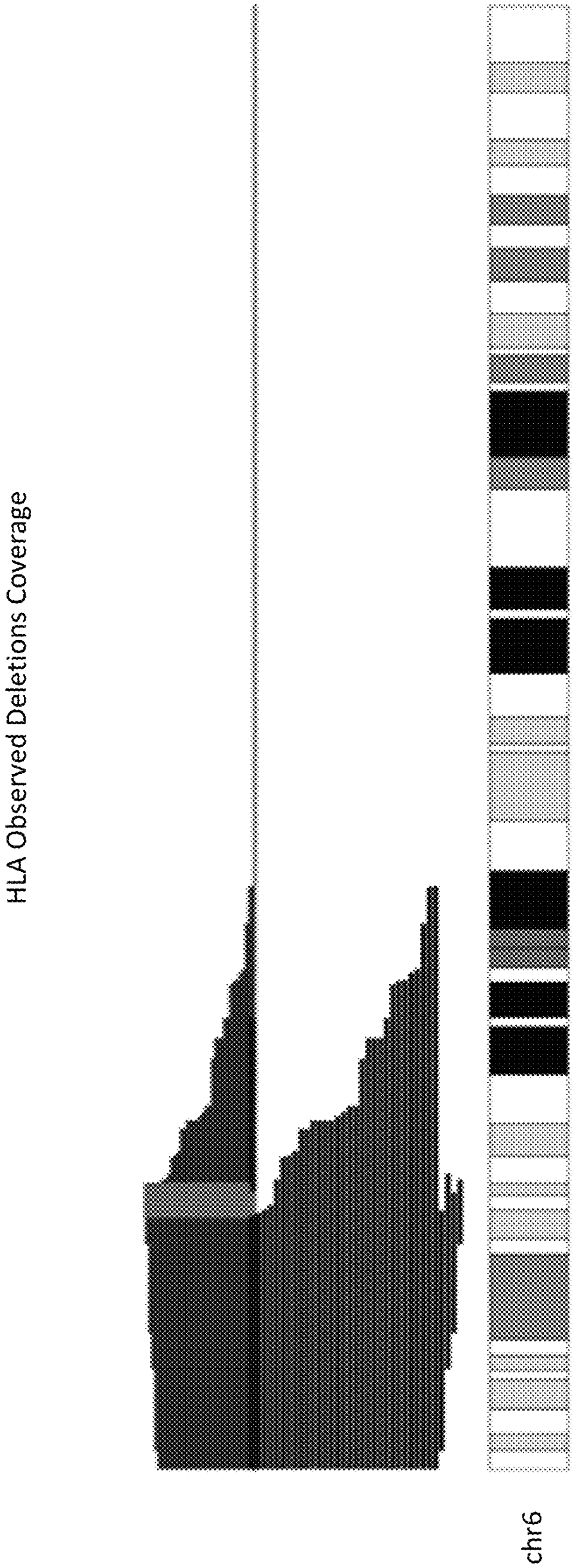
FIG. 15 shows observed deletions of in the genomic region of chromosome 6 related to human leukocyte antigen (HLA) using techniques described herein.

FIG. 15 shows observed deletions of in the genomic region of chromosome 6 related to human leukocyte antigen (HLA) using existing techniques. The observed deletion in HLA region varies between 5 Mb to 60 Mb.

We observed that characterizing HLA LOH refines neoantigen prediction and may have implications for our understanding of resistance mechanisms and immunotherapeutic approaches targeting neoantigens. Prediction of loss of heterozygosity in human leukocyte antigen were made by applying the modeling approaches described herein to samples from 15,618 cancer patients of different cancer types processed on GuardantOMNI® RUO.

Figure 16:
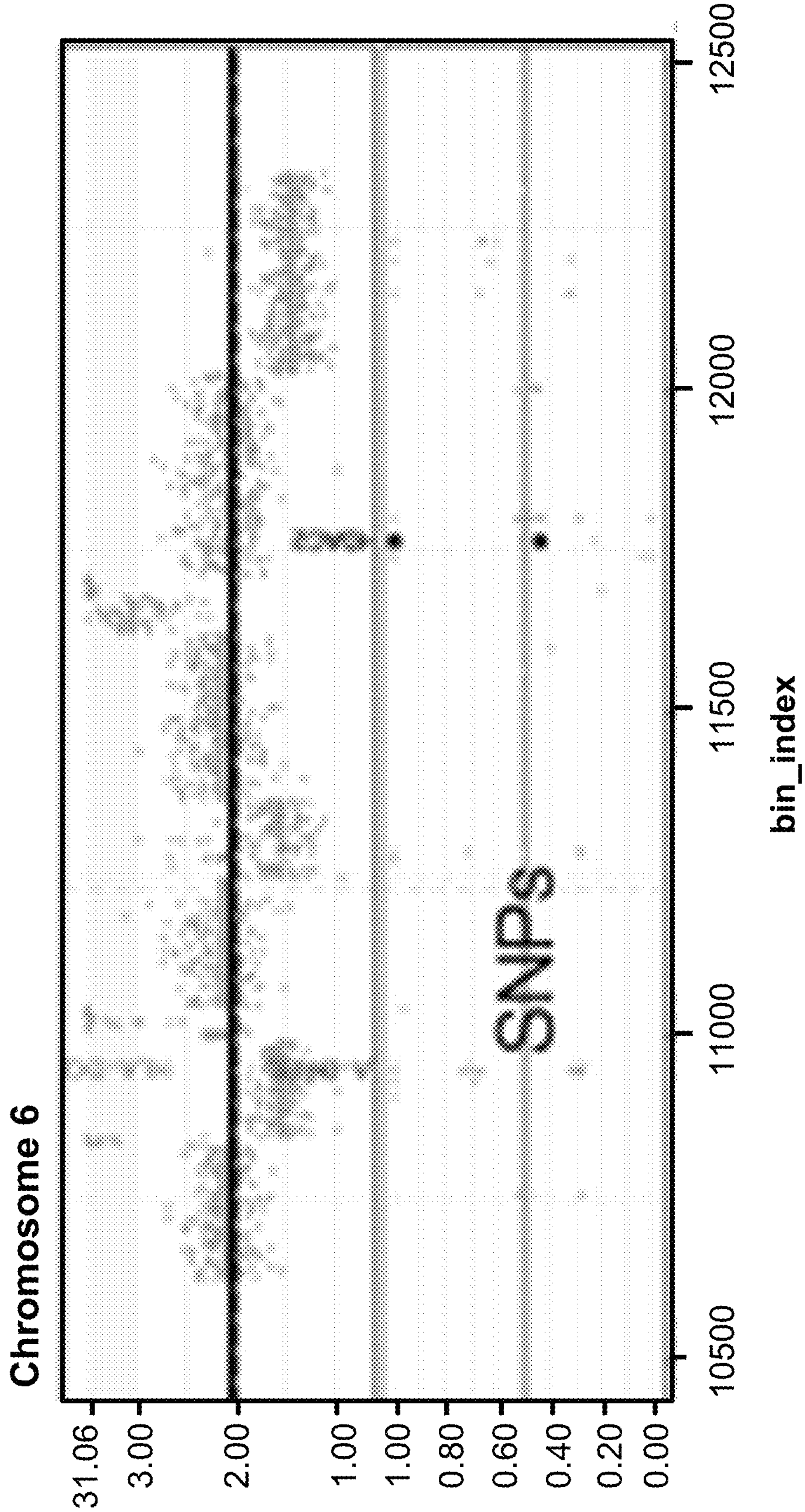
FIG. 16 shows an example of observed coverage of chromosome 6 for a patient predicted to have a loss of heterozygosity (LoH) in HLA region.

FIG. 16 shows an example of observed coverage of chromosome 6 for a patient predicted to have a loss of heterozygosity (LoH) in HLA region.

Figure 17:
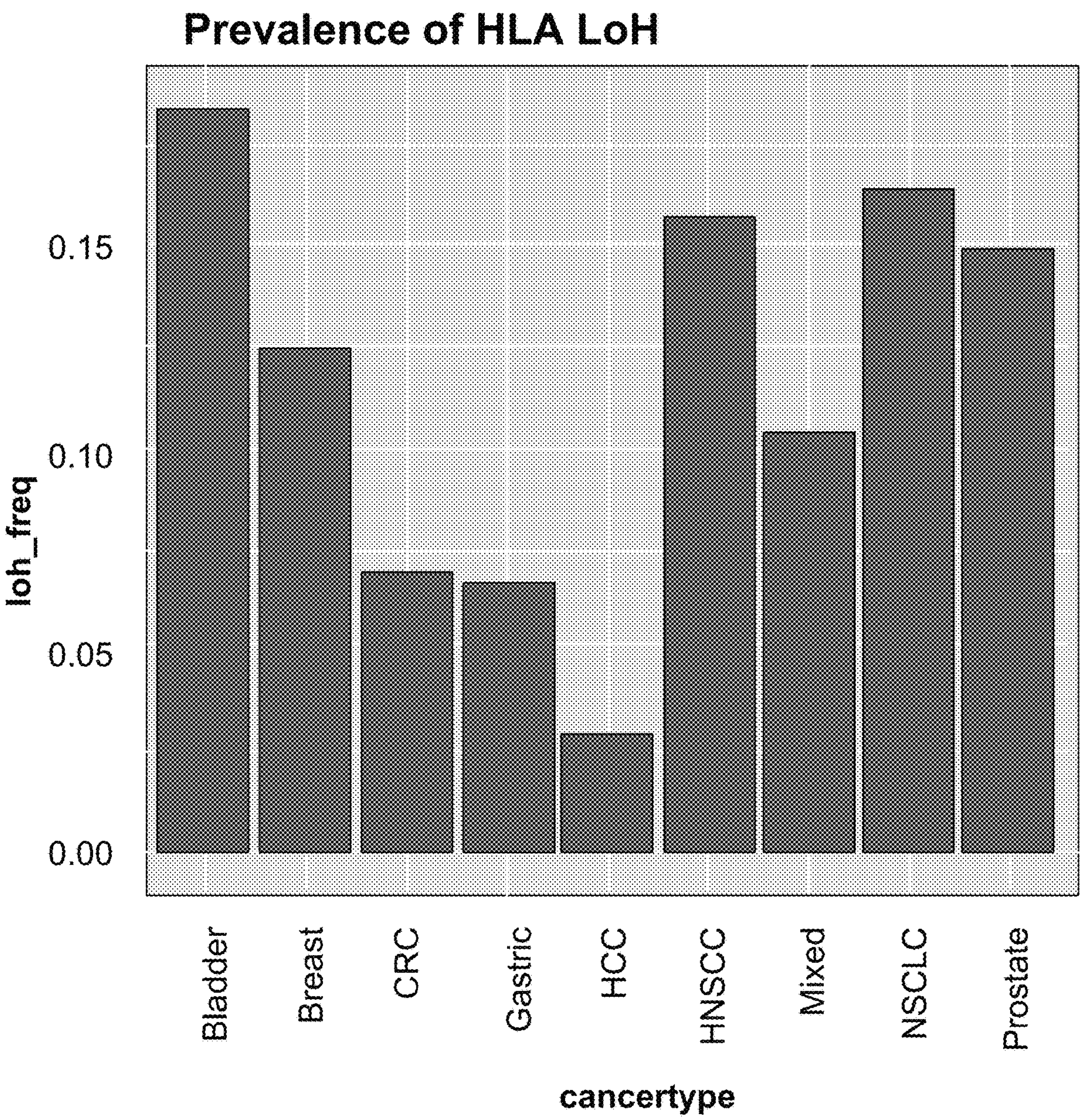
FIG. 17 shows the prevalence of HLA LoH in different cancer types.

FIG. 17 shows the prevalence of HLA LoH in different cancer types. A high prevalence (more than 15%) of LoH in HLA in bladder cancer, prostate cancer, NSCLC and HNSC was observed and is consistent with previous studies that HLA LOH is a common feature of several cancer types that diminishes immunotherapy efficacy.

Example 4

Figure 18:
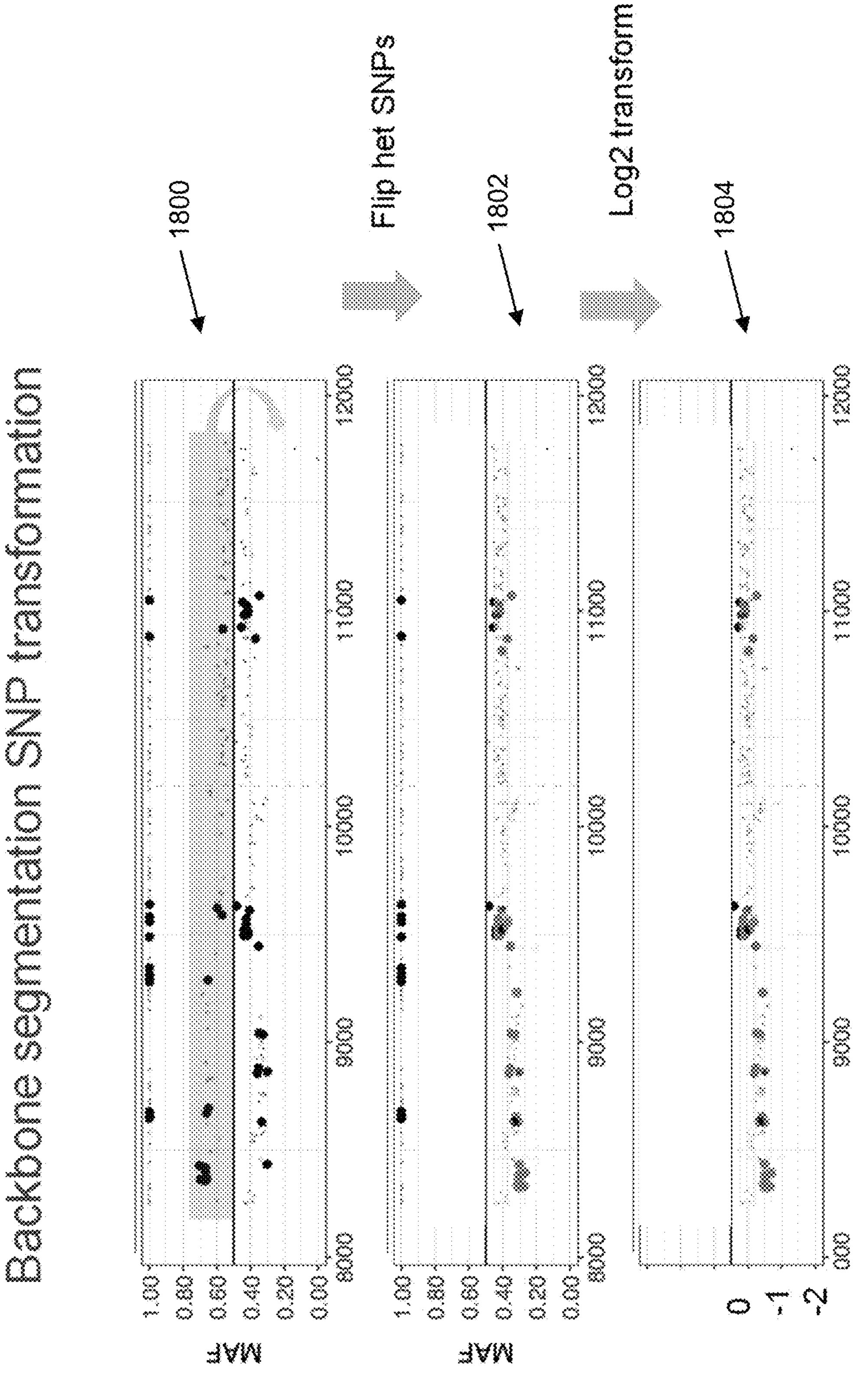
FIG. 18 shows an example of mutant allele fraction for heterozygous single nucleotide polymorphisms (SNPs) at a number of different genomic locations that are modified by determining the reciprocal of the MAFs and then applying a Log base 2 transform.

FIG. 18 shows an example of mutant allele fraction for heterozygous single nucleotide polymorphisms (SNPs) at a number of different genomic locations that are modified by determining the reciprocal of the MAFs and then applying a Log base 2 transform. In particular, 1800 shows mutant allele fraction for a number of SNPs at respective genomic locations of a reference sequence. At least a portion of the SNPs shown in FIG. 18 can correspond to target regions of the reference sequence. Heterozygous SNPs are first adjusted to be below the allelic balanced baseline. That is, when an MAF value is below the baseline value, it is kept as its original value; when an MAF is above the baseline value, it is flipped down to be (1−MAF)×(baseline/0.5). The results of this process are shown in 1802. The adjusted MAFs are then log 2 transformed and shifted up by 1 so that the original allelic balanced MAF of 0.5 is now transformed to be 0. The results of the log base 2 transformation are shown in 1804.

Figure 19:
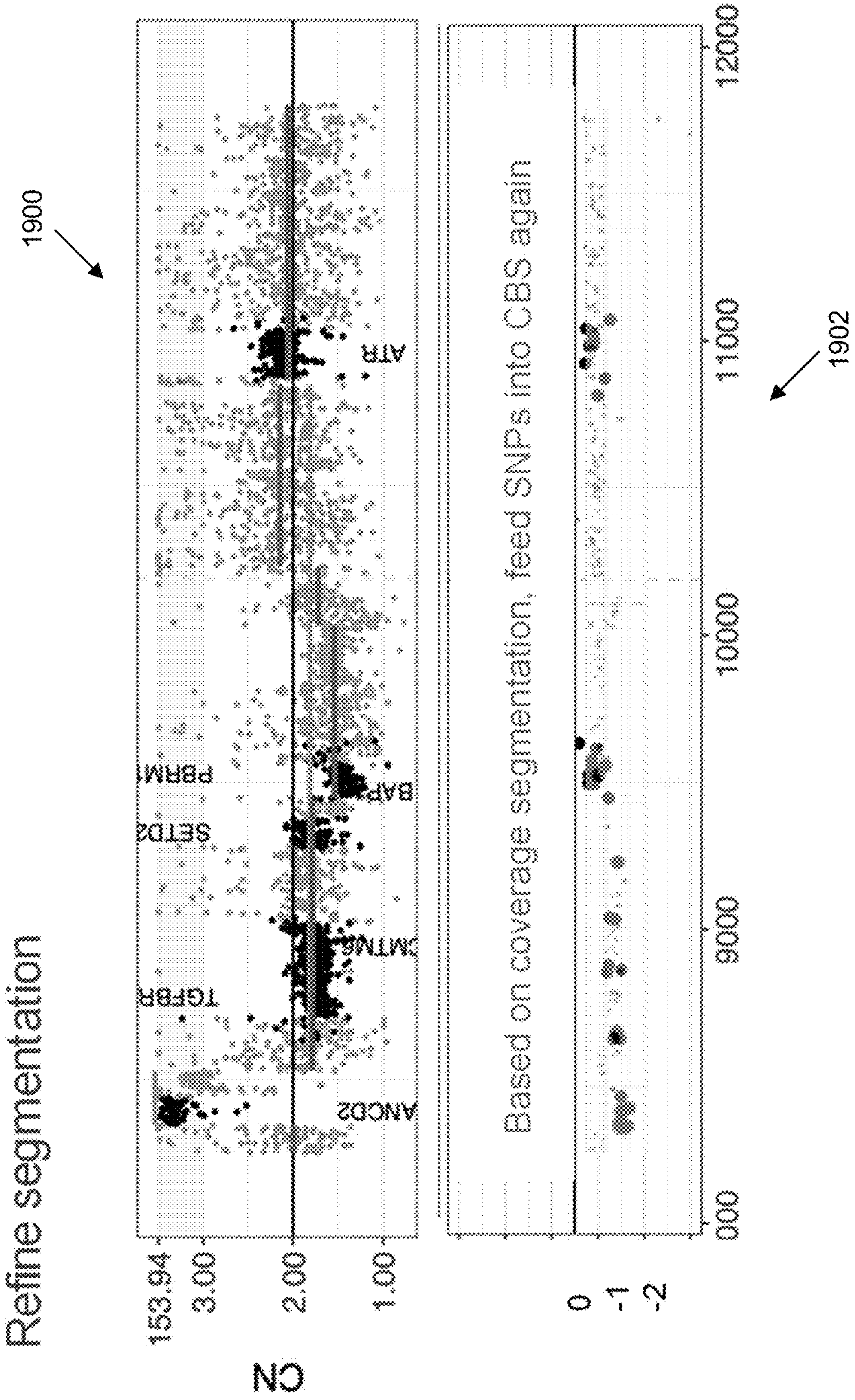
FIG. 19 shows an example refinement of a segmentation process based on copy number using the transformed SNP MAF data shown in FIG. 18.

FIG. 19 shows an example refinement of a segmentation process based on copy number (shown as segments of a first color, such as cyan) using the transformed SNP MAF data shown in FIG. 18. The refinement of the segmentation process (shown as segments of a second color, such as blue) can result in increased accuracy of the estimation of copy numbers for segments of a reference sequence. For example, 1900 shows the results of a first implementation of a circular binary segmentation (CBS) process using coverage data only. In some situations, the results of the CBS process can produce data noise that can lead to an amount of inaccuracy when determining the copy number and/or tumor fraction based on the segments determined using the CBS process based on coverage data only. 1902 shows the results of the log base 2 transformation shown in 1804 of FIG. 18 that can be applied to the results of the implementation of the CBS process shown in 1900. By performing an additional implementation of the CBS process using the results from the coverage data only CBS process and also the data shown in 1902 as input, the accuracy of the segmentation using the CBS process can be improved.

FIG. 20 includes a table showing actual copy number of various genes and differences between the copy number of the genes estimated using segmentation according to an implementation of a CBS process based on coverage data only and the copy number of the genes estimated using the refinement process shown in FIGS. 18 and 19.

What is claimed is:

1. A method comprising:

obtaining, by a computing system including one or more computing devices each having one or more processors and memory, sequence data indicating sequence representations related to polynucleotide molecules included in a sample obtained or having been obtained from a subject receiving immunotherapy:

generating, by the computing system, a set of aligned sequence representations by performing an alignment process that determines one or more of the sequence representations that have at least a threshold amount of homology with respect to a portion of a reference human genome;

determining, by the computing system, a set of off-target sequence representations by identifying a first portion of the number of aligned sequence representations that do not correspond to target regions of the reference human genome;

determining, by the computing system, a set of on-target sequence representations by identifying a second portion of the number of aligned sequence representations that correspond to the target regions of the reference human genome;

determining, by the computing system, first segments of the reference human genome, wherein the first segments do not include the target regions;

determining, by the computing system, first quantitative measures for individual first segments based on a respective subset of the set of off-target sequence representations corresponding to the individual first segments;

determining, by the computing system, first normalized quantitative measures for individual first segments with respect to an additional quantitative measure of the individual first segments;

determining, by the computing system, second normalized quantitative measures for individual first segments by adjusting individual first normalized quantitative measures with respect to a reference quantitative measure for the individual first segments;

determining, by the computing system, second segments of the reference human genome, individual second segments including a greater number of nucleotides than the individual first segments and including a plurality of the individual first segments;

determining, by the computing system, second quantitative measures for individual second segments based on the first normalized quantitative measures and the second normalized quantitative measures of the respective plurality of individual first segments included in the individual second segment;

determining, by the computing system, an estimate of a copy number of tumor cells with respect to individual second segments based on individual second quantitative measures that correspond to the individual second segments;

determining loss of heterozygosity (LOH) in the subject based on the estimate, wherein the LOH characterizes homologous recombination deficiency (HRD) in the subject; and administering a poly (ADP-ribose) polymerases (P ARP) and/or base excision repair (BER) inhibitor to the subject determined to have HRD.

2. The method of claim 1, wherein the first quantitative measures are determined based on a respective number of the polynucleotide molecules included in the sample that correspond to the individual first segments.

3. The method of claim 1, wherein the additional quantitative measure corresponds to a median number of sequence representations for the first segments.

4. The method of claim 1, comprising:

prior to determining the second segments:

determining, by the computing system, guanine-cytosine (GC) content indicating a number of guanine nucleotides and cytosine nucleotides included in a portion of the set of off-target sequence representations corresponding to an individual first segment;

determining, by the computing system, a frequency of sequence representations corresponding to a partition of GC content from a plurality of partitions of GC content in the individual first segment, each partition of GC content of the plurality of partitions of GC content corresponding to a different range of values for GC content;

determining, by the computing system, an expected quantitative measure for the individual first segment based on the frequency of sequence representations corresponding to the plurality of partitions of GC content in the individual first segment; and determining, by the computing system, a GC normalized quantitative measure for the individual first segment based on the expected quantitative measure for the individual first segment.

5. The method of claim 1, comprising:

prior to determining the second segments:

determining, by the computing system, a mappability score for each sequence representation in an individual first segment, the mappability score indicating an amount of homology between a plurality of portions of the human reference genome, each portion of the human reference genome of the plurality of portions of the human reference genome having at least a threshold amount of homology with an additional portion of the human reference genome of the plurality of portions of the human reference genome;

determining, by the computing system, a frequency of sequence representations corresponding to a partition of mappability scores from a plurality of partitions of mappability scores in the individual first segment, each partition of mappability scores of the plurality of partitions of mappability scores corresponding to a different range of values for mappability scores;

determining, by the computing system, an expected quantitative measure for the individual first segment based on the frequency of sequence representations corresponding to the plurality of partitions of mappability scores in the individual first segment; and determining, by the computing system, a mappability score-normalized quantitative measure for the individual first segment based on the expected quantitative measure for the individual first segment.

6. The method of claim 1, comprising:

determining, by the computing system, that a sequence representation that corresponds to an individual first segment has at least a threshold amount of homology with a target region; and determining, by the computing system, that a first quantitative measure of the individual first segment is excluded from determining the individual second quantitative measures.

7. The method of claim 1, comprising:

obtaining, by the computing system, training sequence data indicating additional sequence representations of additional polynucleotide molecules obtained from training samples, wherein the training samples are obtained from individuals in which no copy number alterations are detected;

generating, by the computing system, a number of reference aligned sequence representations by performing an additional alignment process that determines one or more of the additional sequence representations that have at least the threshold amount of homology with respect to a portion of the reference human genome;

determining, by the computing system, an additional set of off-target sequence representations by identifying a portion of the number of additional aligned sequence representations that do not correspond to the target regions of the reference human genome; and determining, by the computing system, individual reference quantitative measures for the individual first segments based on a number of the additional set of off-target sequence representations included in the individual first segments.

8. The method of claim 1, comprising:

determining, by the computing system, a respective number of the on-target sequence representations included in the set of on-target sequence representations that correspond to individual target regions; and determining, by the computing system, individual further quantitative measures for individual target regions based on the respective number of the on-target sequence representations that correspond to the individual target regions;

wherein the estimate of the copy number of tumor cells related to the sample is based on the individual further quantitative measures; and wherein the second segments of the reference human genome are determined based on the individual additional quantitative measures that correspond to the individual target regions.

9. The method of claim 1, wherein:

the first quantitative measures include first size distribution metrics for the individual first segment, at least one of the first normalized quantitative measures or the second normalized quantitative measures correspond to normalized size distribution metrics, the reference quantitative measure is a reference size distribution metric, and the second quantitative measures include second size distribution metrics for the individual second segments; and the method comprises:

determining, by the computing system, a number of nucleotides included in individual sequence representations that correspond to individual first segments to generate individual size distribution metrics for sequence representations of the individual first segments, wherein a size distribution includes a plurality of partitions that each correspond to a respective range of sizes of sequence representations and an individual size distribution metric for an individual first segment indicates a number of the set of off-target sequence representations included in the first segment that correspond to each partition of the plurality of partitions;

determining, by the computing system, the normalized size distribution metrics for the individual first segments according to the individual first size distribution metrics with respect to a reference size distribution metric;

determining, by the computing system, the second size distribution metrics for the individual second segments based on the normalized size distribution metrics of the respective plurality of individual first segments included in the individual second segment; and determining, by the computing system, an additional estimate of the copy number of tumor cells with respect to individual second segments based on the individual second size distribution metrics that correspond to the individual second segments.

10. The method of claim 1, wherein:

the first quantitative measures include first coverage metrics for individual first segments, the first normalized quantitative measures correspond to first normalized coverage metrics, the second normalized quantitative measures correspond to second normalized coverage metrics, the reference quantitative measure is a reference coverage metric, and the second quantitative measures include second coverage metrics for the individual second segments;

the method comprises:

determining, by the computing system, a number of the sequence representations that correspond to individual first segments to generate the individual first coverage metrics for the individual first segments;

determining, by the computing system, the first normalized coverage metrics for the individual first segments according to the individual first coverage metrics;

determining, by the computing system, the second normalized coverage metrics for the individual first segments according to the individual first coverage metrics with respect to the reference coverage metric; and determining, by the computing system, the second coverage metrics for the individual second segments based on the first normalized coverage metrics and the second normalized coverage metrics; and wherein the estimate of the copy number of tumor cells with respect to individual second segments is based on the individual second coverage metrics that correspond to the individual second segments.

11. The method of claim 1, wherein:

the quantitative measures include first size distribution metrics and first coverage metrics for individual first segments;

the first normalized quantitative measures and the second normalized quantitative measures correspond to at least one of normalized size distribution metrics or normalized coverage metrics;

the reference quantitative measure includes a reference size distribution metric and a reference coverage metric; and the second quantitative measures include second size distribution metrics and second coverage metrics for the individual second segments.

12. The method of claim 11, comprising:

determining, by the computing system, a size of individual sequence representations by determining a number of nucleotides included in the individual sequence representations that correspond to individual first segments;

generating, by the computing system, the first size distribution metrics for the individual first segments based on the respective sizes of the individual sequence representations, wherein a size distribution includes a plurality of partitions that each correspond to a respective range of sizes of sequence representations and an individual size distribution metric for an individual first segment indicates a number of the set of off-target sequence representations included in the first segment that correspond to each partition of the plurality of partitions;

determining, by the computing system, the normalized size distribution metrics for the individual first segments according to the individual first size distribution metrics with respect to the reference size distribution metric; and determining, by the computing system, the second size distribution metrics for the individual second segments based on the normalized size distribution metrics of the respective plurality of individual first segments included in the individual second segments.

13. The method of claim 12, comprising:

determining, by the computing system, a number of the sequence representations that correspond to individual first segments to generate the individual first coverage metrics for the individual first segments;

determining, by the computing system, the first normalized coverage metrics for the individual first segments according to the individual first coverage metrics;

determining, by the computing system, the second normalized size distribution metrics for the individual first segments according to the individual first coverage metrics with respect to the reference coverage metric; and determining, by the computing system, the second coverage metrics for the individual second segments based on the first normalized coverage metrics and the second normalized coverage metrics.

14. The method of claim 13, wherein the estimate of the copy number of tumor cells with respect to individual second segments is an aggregate estimate of the copy number of tumor cells with respect to individual second segments that is generated, by the computing system, by determining a first estimate of the copy number of tumor cells with respect to individual second segments based on the second size distribution metrics and a second estimate of the copy number of tumor cells with respect to individual second segments based on the second coverage metrics.

15. The method of claim 14, comprising:

determining, by the computing system, a ratio of a number of wild-type alleles related to the sample with respect to a number of mutated alleles related to the sample; and determining, by the computing system, a heterozygous single nucleotide polymorphism (SNP) metric based on the ratio.

16. The method of claim 15, comprising:

determining, by the computing system, an additional estimate of the tumor fraction for the sample based on the SNP metric; and determining, by the computing system, an additional estimate of the copy number of tumor cells related to the sample based on the SNP metric.

17. The method of claim 1, comprising:

determining, by the computing system, parameters of a model that correspond to a likelihood function that generates the estimate of the copy number of tumor cells related to the sample;

wherein the parameters of the model correspond to at least a portion of the individual estimates of the copy number of tumor cells with respect to the individual second segments and correspond to the estimate for the tumor fraction of the sample.

18. The method of claim 17, wherein the parameters of the model correspond to one or more SNP metrics, individual SNP metrics of the one or more SNP metrics being related to a respective ratio of a number of mutant alleles with respect to a number of wild-type alleles.

19. The method of claim 1, wherein:

at least a portion of the individual first segments include from about 30,000 nucleotides to about 150,000 nucleotides of the reference human genome;

at least a portion of the individual second segments include from at least about 1 million nucleotides to about 10 million nucleotides of the reference human genome; and the second segments are determined by one or more circular binary segmentation processes.

20. The method of claim 1, wherein the sample includes cell-free DNA obtained from the subject.

21. The method of claim 1, comprising:

determining, by the computing system, an estimate for a tumor fraction of the sample based on the individual second quantitative metrics.

22. The method of claim 1, comprising:

determining, by the computing system, a number of the sequence representations that correspond to individual first segments and that correspond to one or more single nucleotide polymorphisms (SNPs);

determining, by the computing system, a mutant allele fraction for an individual SNP based on the number of sequence representations that correspond to the individual SNP.

23. The method of claim 22, wherein the second segments of the reference human genome are determined based on mutant allele fractions for the individual first segments.

24. The method of claim 22, comprising:

performing, by the computing system, a first implementation of a circular binary segmentation process based on the second normalized quantitative measures to determine a first estimate of the second segments of the reference human genome; and performing, by the computing system, a second implementation of the circular binary segmentation process based on the mutant allele fractions of the individual first segments to determine a second estimate of the second segments of the reference human genome.

25. The method of claim 1, comprising administration of one or more PARP inhibitors selected from the group consisting of: VELIPARIB, OLAPARIB, TALAZOPARIB, RUCAPARIB, NIRAPARIB, PAMIPARIB, CEP 9722 (Cephalon), E7016 (Eisai), E7449 (Eisai, a PARP 1/2 and tankyrase 1/2 inhibitor), and 3-Aminobenzamide.

* * * * *